US006781028B1

(12) United States Patent
Costa et al.

(10) Patent No.: US 6,781,028 B1
(45) Date of Patent: Aug. 24, 2004

(54) ANIMAL MODELS AND METHODS FOR ANALYSIS OF LIPID METABOLISM AND SCREENING OF PHARMACEUTICAL AND PESTICIDAL AGENTS THAT MODULATE LIPID METABOLISM

(75) Inventors: Michael R. Costa, San Francisco, CA (US); Stephen K. Doberstein, San Francisco, CA (US); Sarah L. Elson, San Francisco, CA (US); Kimberly Carr Ferguson, Burlingame, CA (US); Sheila Akiko Homburger, Oakland, CA (US)

(73) Assignee: Exelixis, Inc., South San Francisco, CA (US)

( * ) Notice: Subject to any disclaimer, the term of this patent is extended or adjusted under 35 U.S.C. 154(b) by 35 days.

(21) Appl. No.: 09/332,522

(22) Filed: Jun. 14, 1999

(51) Int. Cl.[7] ........................ G01N 33/00; A01K 67/00; C07H 21/02; C12N 5/00; C12N 15/63
(52) U.S. Cl. ........................ 800/3; 800/13; 435/320.1; 435/325; 536/23.1
(58) Field of Search .............................. 536/23.1, 23.5, 536/24.1; 435/320.1, 325; 800/8

(56) References Cited

U.S. PATENT DOCUMENTS

| | | | | |
|---|---|---|---|---|
| 4,935,363 A | | 6/1990 | Brown et al. ............ | 435/172.3 |
| 5,215,910 A | | 6/1993 | Brown et al. ............ | 435/240.2 |
| 5,256,545 A | | 10/1993 | Brown et al. ............. | 435/69.1 |
| 5,378,603 A | | 1/1995 | Brown et al. ................... | 435/6 |
| 5,498,696 A | | 3/1996 | Briggs et al. ............... | 530/350 |
| 5,527,690 A | | 6/1996 | Goldstein et al. .......... | 435/69.1 |
| 5,650,550 A | * | 7/1997 | Korach .......................... | 800/2 |
| 5,780,262 A | | 7/1998 | Brent et al. ................ | 435/69.1 |
| 5,891,631 A | | 4/1999 | Goldstein et al. .............. | 435/6 |
| 5,919,462 A | * | 7/1999 | Narwa ..................... | 424/208.1 |

FOREIGN PATENT DOCUMENTS

WO      WO9102058    *   2/1991

OTHER PUBLICATIONS

NCBI database accession No. CAAA87777, 2003.*
NCBI database accession No. C11831, 1998.*
Kohara et al (Seq Name gb_est47:D35004; Accesssion No. D35004; published Aug. 8, 1994).*
Villee et al, General Zoology), chapter 24, pp. 509–515, 1984, Saunders Colleger Publishing, NY.*
www.ncbi.nlm.nih.gov (National Center for Biotechnology Information) GenBank Accession No. AA391707 5prime LD Drosophilia melanogaster embryo BlueScript Drosophilia melanogaster cDNA clone LD11632 5prime, mRNA sequence.
www.ncbi.nlm.nih.gov (National Center for Biotechnology Information) GenBank Accession No. AA439767 5prime LD Drosophilia melanogaster embryo BlueScript Drosophilia melanogaster cDNA clone LD14421 5prime, mRNA sequence.

www.ncbi.nlm.nih.gov (National Center for Biotechnology Information) GenBank Accession No. AC007121 Drosophilia melanogaster, chromosome 2R, region 42A8–42A16, P1 clones DS06954 and DS05325, complete sequence.
www.ncbi.nlm.nih.gov (National Center for Biotechnology Information) GenBank Accession No. U38238 Drosophilia melanogaster transcription factor HLH106 mRNA, complete cds.
www.ncbi.nlm.nih.gov (National Center for Biotechnology Information) GenBank Accession No. B41527 HS–1053–B2–G10–MR.abi CIT Human Genomic Sperm Library C Homo sapiens genomic clone Plate=CT 775 Col=20 Row=N, genomic survey sequence.
www.ncbi.nlm.nih.gov (National Center for Biotechnology Information) GenBank Accession No. A54962 sterol regulatory element binding protein 2 precursor—human.
www.ncbi.nlm.nih.gov (National Center for Biotechnology Information) GenBank Accession No. B54962 sterol regulatory element binding protein 2 precursor—Chinese hamster.
www.ncbi.nlm.nih.gov (National Center for Biotechnology Information) GenBank Accession No. A54164 sterol regulatory element–binding protein 1—Chinese hamster.
www.ncbi.nlm.nih.gov (National Center for Biotechnology Information) GenBank Accession No. D83782 Human mRNA for KIAA0199 gene, partial cds.
www.ncbi.nlm.nih.gov (National Center for Biotechnology Information) GenBank Accession No. BAA12111 the KIAA0199 gene is expressed ubiquitously.; the KIAA0199 protein shows similarity to sea urchin hydroxymethylglutaryl–CoA reductase, and retains 8 hydrophobic domains. [Homo sapiens].
www.ncbi.nlm.nih.gov (National Center for Biotechnology Information) GenBank Accession No. C11831 Yuji Kohara unpublished cDNA Caenorhabditis elegans cDNA clone yk125f3 5', mRNA sequence.
www.ncbi.nlm.nih.gov (National Center for Biotechnology Information) GenBank Accession No. AAB13887 Sequence 38 from patent US 5527690.
www.ncbi.nlm.nih.gov (National Center for Biotechnology Information) GenBank Accession No. aab13894 Sequence 54 from patent US 5527690.

(List continued on next page.)

Primary Examiner—Ram R. Shukla
(74) Attorney, Agent, or Firm—Jan P. Brunelle

(57) ABSTRACT

Drosophila melanogaster and C. elegans that have been genetically modified to express or mis-express proteins involved in the sterol regulatory element binding protein (SREBP) pathway are described. These genetically modified animal models have identifiable phenotypes that make them useful in assays for studying lipid metabolism, other genes implicated in lipid metabolism, and compounds capable of modulating lipid metabolism pathways. Methods for studying lipid metabolism in living nematodes using fluorescently-labelled fatty acid conjugates, such BODITY™ fatty acid conjugates, are also described. Novel SREBP pathway nucleic acid and protein sequences are also described.

16 Claims, 25 Drawing Sheets

OTHER PUBLICATIONS www.ncbi.nlm.nih.gov (National Center for Biotechnology Information) GenBank Accession No. AAB19103 SREBP cleavage activating protein [*Cricetulus griseus*].
www.ncbi.nlm.nih.gov (National Center for Biotechnology Information) GenBank Accession No. CAA69563 orf c04034 [*Sulfolobus solfataricus*].
www.ncbi.nlm.nih.gov (National Center for Biotechnology Information) GenBank Accession No. AAB85845 conserved protein [*Methanobacterium thermoautotrophicum*].
www.ncbi.nlm.nih.gov (National Center for Biotechnology Information) GenBank Accession No. AAC53526 S2P [*Cricetulus griseus*].
www.ncbi.nlm.nih.gov (National Center for Biotechnology Information) GenBank Accession No. AAC51937 S2P [*Homo sapiens*].
www.ncbi.nlm.nih.gov (National Center for Biotechnology Information) GenBank Accession No. CAA18255 putative protein [*Arabidopsis thaliana*].
www.ncbi.nlm.nih.gov (National Center for Biotechnology Information) GenBank Accession No. CAA87777 similarity to the transmembranous domain of 3–hydroxy–3–methylglutaryl–coenzyme A reductase; cDNA EST EMBL:D35100 comes from this gene; cDNA EST EMBL:D32450 comes from this gene; cDNA EST EMBL:D33885 comes from this gene; cDNA EST EMBL:D36828 comes from this gene; cDNA EST EMBL:D67504 comes from this gene; cDNA EST EMBL:D64495 comes from this gene; cDNA EST EMBL:D68193 comes from this gene; cDNA EST EMBL:D64931 comes from this gene; cDNA EST EMBL:C11459 comes from this gene; cDNA EST EMBL:C13582 comes from this gene; cDNA EST yk315f2.3 comes from this gene; cDNA EST yk315f2.5 comes from this gene; cDNA EST yk244b1.3 comes from this gene; cDNA EST yk244b1.5 comes from this gene; cDNA EST yk194g11.3 comes from this gene; cDNA EST yk194g11.5 comes from this gene; cDNA EST yk226d12.5 comes from this gene; cDNA EST yk353e6.5 comes from this gene; cDNA EST yk390b6.3 comes from this gene; cDNAn EST yk390b6.5 comes from this gene [*Caenorhabditis elegans*].
www.ncbi.nlm.nih.gov (National Center for Biotechnology Information) GenBank Accession No. CAA221042 predicted using Genefinder; similar to Helix–loop–helix DNA–binding domain; cDNA EST EMBL:D34815 comes from this gene; cDNA EST EMBL:D35004 comes from this gene; cDNA EST EMBL:D68853 comes form this gene; cDNA EST EMBL:D67853 comes from this gene; cDNA EST yk349h3.5 comes from this gene; cDNA EST EMBL:D32385 comes from this gene; cDNA EST EMBL:D64735 comes from this gene; cDNA EST EMBL:D64806 comes from this gene; cDNA EST EMBL:C10363 comes from this gene; cDNA EST EMBL:C11998 comes from this gene [*Caenorhabditis elegans*].
www.ncbi.nlm.nih.gov (National Center for Biotechnology Information) GenBank Accession No. AAC91576 Sequence 18 from patent US 5780262.
www.ncbi.nlm.nih.gov (National Center for Biotechnology Information) GenBank Accession No. AAC50051 SREBP–1 [*Homo sapiens*].
www.ncbi.nlm.nih.gov (National Center for Biotechnology Information) GenBank Accession No. AAD08631 SP2 metalloprotease [*Homo sapiens*].
www.ncbi.nlm.nih.gov (National Center for Biotechnology Information) GenBank Accession No. 642180 *Carnorhabditis elegans* cosmid D2013.
www.ncbi.nlm.nih.gov (National Center for Biotechnology Information) GenBank Accession No. BAA74795 sterol regulatory element–binding protein–1 (SREBP–1)[*Mus musculus*].
www.ncbi.nlm.nih.gov (National Center for Biotechnology Information) GenBank Accession No. AAA50746 sterol regulatory element binding protein–2 [*Homo sapiens*].
www.ncbi.nlm.nih.gov (National Center for Biotechnology Information) GenBank Accession No. AAA20085 sterol regulatory element binding protein–1 [*Cricetulus griseus*].
www.ncbi.nlm.nih.gov (National Center for Biotechnology Information) GenBank Accession No. A48085 transcription factor ADD1—rat.
www.ncbi.nlm.nih.gov (National Center for Biotechnology Information) GenBank Accession No. AAA74141sterol regulatory element binding protein–2 [*Cricetulus griseus*].
Brown and Goldstein, 1997, Cell 89:331–340.
Faergeman et al., 1997, J. Biol. Chem. 272(13):8531–8538.
Furlong et al., 1995, J. Lipid Res. 36(1):1–12.
Hua et al., 1996 Cell 87:415–426.
Margolis and Duyk, 1998, Nat. Biotechnol. 16:311.
Martin and Kusel, 1992, Parasitology 104(3):549–555.
Pagano et al., 1991, J. Cell. Biol. 113(6):1267–1279.
Pagano and Chen, 1998, Ann NY Acad. Sci. 845:152–160.
Rawson et al., 1997, Mol. Cell 1:47–57.
Redman and Kusel, 1996, Parasitology 113(2):137–143.
Sakai et al., 1998, J. Biol. Chem. 273:5785–5793.
Scangos, 1997, Nat. Biotechnol. 15:1220–1221.
Spiegelman et al., 1996, Cell 87:377–389.
Theopold et al., 1996. Proc. Natl. Acad Sci. USA 93(3):1195–1199.
J Rudinger, Peptide Hormones, "Characteristics of the amino acids as components of a peptide hormone sequence," Jun. 1976, pp. 1–7.*
Chitwood, 1999, Biochemistry and Function of Nematode Steroids, Critical Reviews in Biochemistry and Molecular Biology 34(4):273–284.
The *C. elegans* Sequencing Consortium, 1998, Genome Sequence of the Nematode *C. elegans*: A Platform for Investigating Biology, Science 282:2012–2018.
Kimura et al., 1997, daf–2, an Insulin Receptor–Like Gene That Regulates Longevity and Diapause in *Caenorhabditis elegans*, Science 277:942–946.
Rosenfeld, et al., 1998, HLH106, a Drosophilia Sterol Regulatory Element–binding Protein in a Natural Cholesterol Auxotroph, J. Biological Chemistry 273:16112–16121.
Shimomura et al., 1998, Nuclear Sterol Regulatory Element– binding Protein Activates Genes Responsible for the Entire Program of Unsaturated Fatty Acid Biosynthesis in Transgenic Mouse Liver, J. Biological Chemistry 273:35299–35306.
Shimano et al., 1997, Elevated Levels of SREBP–2 and Cholesterol Synthesis in Livers of Mice Homozygous for a Targeted Disruption of the SREBP–1 Gene, J. Clinical Investigation 100:2115–2124.
Xu et al., Sterol regulatory element binding protein–1 expression is suppressed by dietary polyunsaturated fatty acids. The Journal of Biological Chemistry. Aug. 1999. vol. 274, No. 33, pp. 23577–23583.

* cited by examiner

```
GGTTTAATTACCCAAGTTTGAGAATGAACGAAGAATTCGAGGGAGACGTC      50
CCAAATTAATGGGTTCAAACTCTTACTTGCTTCTTAAGCTCCCTCTGCAG

CCTATGTCGGATCCGTTTCTCTCATTGGTCACAAAATTGGATGATATTGC     100
GGATACAGCCTAGGCAAAGAGAGTAACCAGTGTTTTAACCTACTATAACG

GCCATTTCCAAATAACGACCCGCTCGATTTTGACATGGAGCACAACTGGC     150
CGGTAAAGGTTTATTGCTGGGCGAGCTAAAACTGTACCTCGTGTTGACCG

AAGAGCCCGGACCATCACAACAACCGGATCCATCAATTCCCGGAAATCAA     200
TTCTCGGGCCTGGTAGTGTTGTTGGCCTAGGTAGTTAAGGGCCTTTAGTT

CACAGTCCGCCACAGGAATATTATGATATTGATGGTCAACGAGACGTAAG     250
GTGTCAGGCGGTGTCCTTATAATACTATAACTACCAGTTGCTCTGCATTC

CACCTTACACTCCCTGCTCAACCACAACAACGACGACTTCTTCTCAATGC     300
GTGGAATGTGAGGGACGAGTTGGTGTTGTTGCTGCTGAAGAAGAGTTACG

GATTTTCCCCGCCAAACTTTGATCTCGGCGGAGGCCGTGGACCTTCTCTA     350
CTAAAAGGGGCGGTTTGAAACTAGAGCCGCCTCCGGCACCTGGAAGAGAT

GCCGCCACCCAACAATTATCTGGAGAAGGTCCTGCAAGTATGCTTAACCC     400
CGGCGGTGGGTTGTTAATAGACCTCTTCCAGGACGTTCATACGAATTGGG

CTTACAAACATCTCCACCAAGTGGAGGTTACCCCCGGCAGATGCCTACA     450
GAATGTTTGTAGAGGTGGTTCACCTCCAATGGGGGGCCGTCTACGGATGT

GACCTCTATCACTTGCTCAACAACTCGCCGCGCCAGCGATGACTCCACAT     500
CTGGAGATAGTGAACGAGTTGTTGAGCGGCGCGGTCGCTACTGAGGTGTA

CAGGCAGCGTCGCTTTTTGTTAATACTAATGGAATTGATCAAAAGAATTT     550
GTCCGTCGCAGCGAAAACAATTATGATTACCTTAACTAGTTTTCTTAAA

CACTCATGCAATGCTATCTTCACCACACCATACCTCAATGACTTCTCAAC     600
GTGAGTACGTTACGATAGAAGTGGTGTGGTATGGAGTTACTGAAGAGTTG

CATATACAGAAGCCATGGGACATATCAACGGGTACATGTCTCCATACGAC     650
GTATATGTCTTCGGTACCCTGTATAGTTGCCCATGTACAGAGGTATGCTG

CAAGCTCAAGGCCCATCAGGACCATCATATTACTCACAACACCATCAATC     700
GTTCGAGTTCCGGGTAGTCCTGGTAGTATAATGAGTGTTGTGGTAGTTAG

TCCACCACCTCATCACCACCATCACCACCCGATGCCAAAAATCCATGAGA     750
AGGTGGTGGAGTAGTGGTGGTAGTGGTGGGCTACGGTTTTTAGGTACTCT

ACCCTGAACAAGTGGCATCTCCATCGATTGAAGATGCTCCAGAGACGAAA     800
TGGGACTTGTTCACCGTAGAGGTAGCTAACTTCTACGAGGTCTCTGCTTT
```

FIG. 3A

| | |
|---|---|
| CCAACTCATTTGGTTGAACCACAAAGTCCAAAAAGCCCGCAGAATATGAA<br>GGTTGAGTAAACCAACTTGGTGTTTCAGGTTTTTCGGGCGTCTTATACTT | 850 |
| AGAGGAGCTTCTTCGGTTACTAGTTAACATGTCTCCGAGTGAAGTTGAAC<br>TCTCCTCGAAGAAGCCAATGATCAATTGTACAGAGGCTCACTTCAACTTG | 900 |
| GGTTAAAGAATAAAAAATCAGGAGCATGTTCAGCGACGAATGGGCCATCG<br>CCAATTTCTTATTTTTAGTCCTCGTACAAGTCGCTGCTTACCCGGTAGC | 950 |
| AGGAGTAAGGAGAAGGCGGCGAAGATTGTGATTCAGGAGACAGCGGAAGG<br>TCCTCATTCCTCTTCCGCCGCTTCTAACACTAAGTCCTCTGTCGCCTTCC | 1000 |
| GGATGAAGATGAGGATGATGAGGATAGTGATTCCGGGGAGACTATGTCTC<br>CCTACTTCTACTCCTACTACTCCTATCACTAAGGCCCTCTGATACAGAG | 1050 |
| AGGGAACTACTATTATTGTTCGAAGACCAAAAACCGAGCGTCGTACGGCA<br>TCCCTTGATGATAATAACAAGCTTCTGGTTTTTGGCTCGCAGCATGCCGT | 1100 |
| CACAATCTCATCGAAAAGAAGTATAGATGCTCAATAAATGATCGAATTCA<br>GTGTTAGAGTAGCTTTTCTTCATATCTACGAGTTATTTACTAGCTTAAGT | 1150 |
| ACAGCTGAAAGTACTTTTGTGTGGGGATGAAGCTAAGCTTTCAAAATCGG<br>TGTCGACTTTCATGAAAACACACCCCTACTTCGATTCGAAAGTTTTAGCC | 1200 |
| CAACACTACGACGGGCTATTGAACATATCGAGGAGGTTGAACACGAGAAT<br>GTTGTGATGCTGCCCGATAACTTGTATAGCTCCTCCAACTTGTGCTCTTA | 1250 |
| CAGGTGTTGAAGCATCATGTTGAACAAATGAGAAAGACACTGCAGAATAA<br>GTCCACAACTTCGTAGTACAACTTGTTTACTCTTTCTGTGACGTCTTATT | 1300 |
| TCGATTACCGTACCCGGAACCAATTCAATACACTGAATACTCTGCCCGAT<br>AGCTAATGGCATGGGCCTTGGTTAAGTTATGTGACTTATGAGACGGGCTA | 1350 |
| CACCCGTCGAATCATCTCCTTCTCCACCTAGAAATGAGAGAAAACGATCA<br>GTGGGCAGCTTAGTAGAGGAAGAGGTGGATCTTTACTCTCTTTTGCTAGT | 1400 |
| CGAATGAGCACAACGACTCCTATGAAGAATGGAACTAGAGATGGATCTTC<br>GCTTACTCGTGTTGCTGAGGATACTTCTTACCTTGATCTCTACCTAGAAG | 1450 |
| GAAAGTTACCCTTTTTGCGATGCTCCTAGCAGTTCTGATTTTTAATCCGA<br>CTTTCAATGGGAAAAACGCTACGAGGATCGTCAAGACTAAAAATTAGGCT | 1500 |
| TTGGATTGCTCGCTGGAAGTGCGATATTCTCAAAAGCCGCTGCAGAAGCT<br>AACCTAACGAGCGACCTTCACGCTATAAGAGTTTTCGGCGACGTCTTCGA | 1550 |
| CCGATTGCCTCCCCGTTCGAGCATGGAAGAGTGATTGATGACCCGGATGG<br>GGCTAACGGAGGGGCAAGCTCGTACCTTCTCACTAACTACTGGGCCTACC | 1600 |

FIG. 3B

```
AACTAGCACTCGGACGCTTTTCTGGGAAGGGAGTATCATCAATATGAGCT    1650
TTGATCGTGAGCCTGCGAAAAGACCCTTCCCTCATAGTAGTTATACTCGA

ATGTCTGGGTGTTCAACATCTTAATGATCATATATGTGGTTGTCAAACTG    1700
TACAGACCCACAAGTTGTAGAATTACTAGTATATACACCAACAGTTTGAC

CTGATCCATGGTGACCCTGTTCAAGACTTCATGTCCGTTTCATGGCAGAC    1750
GACTAGGTACCACTGGGACAAGTTCTGAAGTACAGGCAAAGTACCGTCTG

TTTTGTGACGACTCGAGAGAAGGCGAGAGCCGAGTTGAACTCTGGAAATT    1800
AAAACACTGCTGAGCTCTCTTCCGCTCTCGGCTCAACTTGAGACCTTTAA

TGAAAGATGCTCAGAGAAAGTTCTGCGAGTGTCTTGCAACGTTGGATCGA    1850
ACTTTCTACGAGTCTCTTTCAAGACGCTCACAGAACGTTGCAACCTAGCT

TCGCTTCCATCACCGGGGGTTGATTCGGTGTTTTCGGTTGGCTGGGAATG    1900
AGCGAAGGTAGTGGCCCCCAACTAAGCCACAAAAGCCAACCGACCCTTAC

CGTTCGACATCTTTTGAATTGGTTGTGGATCGGGAGATACATCGCAAGAA    1950
GCAAGCTGTAGAAAACTTAACCAACACCTAGCCCTCTATGTAGCGTTCTT

GGCGCAGGTCCACCACGAAGCCTGTCTCAGTCGTTTGTAGGAGTCATGCG    2000
CCGCGTCCAGGTGGTGCTTCGGACAGAGTCAGCAAACATCCTCAGTACGC

CAGACTGCAGTTCTCTATCATGAAATTCATCAGCTCCATCTAATGGGTAT    2050
GTCTGACGTCAAGAGATAGTACTTTAAGTAGTCGAGGTAGATTACCCATA

CACTGGAAACTTCGAAGACACCTATGAACCATCCGCCCTAACGGGCCTCT    2100
GTGACCTTTGAAGCTTCTGTGGATACTTGGTAGGCGGGATTGCCCGGAGA

TCATGTCCCTCTGTGCAGTAAACCTTGCTGAAGCTGCCGGAGCATCAAAC    2150
AGTACAGGGAGACACGTCATTTGGAACGACTTCGACGGCCTCGTAGTTTG

GACGGACTTCCACGCGCCGTCATGGCTCAGATCTACATTTCTGCATCCAT    2200
CTGCCTGAAGGTGCGCGGCAGTACCGAGTCTAGATGTAAAGACGTAGGTA

CCAATGCCGTTTGGCTCTTCCGAACCTACTCGCACCATTCTTCTCGGGAT    2250
GGTTACGGCAAACCGAGAAGGCTTGGATGAGCGTGGTAAGAAGAGCCCTA

ACTTTTTACGAAGAGCTCGAAGGCACGTGCGTCGAGCTCCGGAGCACTCG    2300
TGAAAAATGCTTCTCGAGCTTCCGTGCACGCAGCTCGAGGCCTCGTGAGC

GTGTCCCATTTGTTATGGATCTTCCATCCAGCGACAAGAAAGTTCATGTC    2350
CACAGGGTAAACAATACCTAGAAGGTAGGTCGCTGTTCTTTCAAGTACAG

AGATGCGAAAAGGTTGGAGCATGTGTTGAGCTCGAAGCAGAAGCAGTTGA    2400
TCTACGCTTTTCCAACCTCGTACACAACTCGAGCTTCGTCTTCGTCAACT
```

FIG. 3C

```
GATTTGGGTCTTTTGTGGAAGATGAGCAATTATCCCCACTTGCTCGAATC          2450
CTAAACCCAGAAAACACCTTCTACTCGTTAATAGGGGTGAACGAGCTTAG

CGAACAACGCTGAAAGTGTACCTACTCTCCAAACTTGTACAGGAACTTGT          2500
GCTTGTTGCGACTTTCACATGGATGAGAGGTTTGAACATGTCCTTGAACA

CGGTGGTGACGAGATCTTTACAAAAAATGTGGAACGCATCCTAAATGACA          2550
GCCACCACTGCTCTAGAAATGTTTTTTACACCTTGCGTAGGATTTACTGT

ATGACCGTCTCGATGATGAAGTAGACGTGGTTGATGTTTCAAGACTTTTG          2600
TACTGGCAGAGCTACTACTTCATCTGCACCAACTACAAAGTTCTGAAAAC

GTGACAATTTCAACGCAGTGCGCTGCCATTTTGACTAATGAGAAGGATGA          2650
CACTGTTAAAGTTGCGTCACGCGACGGTAAAACTGATTACTCTTCCTACT

GTCAGCGAAATTCGGAACCTGGATCTCTCGAAACGGAGATGCTTGTTGCA          2700
CAGTCGCTTTAAGCCTTGGACCTAGAGAGCTTTGCCTCTACGAACAACGT

CATGGTGGACGCACGTTCTGACATGTGGAATCTATTGGAGGAGTAACAAG          2750
GTACCACCTGCGTGCAAGACTGTACACCTTAGATAACCTCCTCATTGTTC

AATGAGCTGGCACGGCAACACTATTCACTGATCAGGAACTGTCCGCCGAA          2800
TTACTCGACCGTGCCGTTGTGATAAGTGACTAGTCCTTGACAGGCGGCTT

GATTTTGACAGACAATCTGGGTTTGGCGGTTGGCCACGCGTTGTGTGCTC          2850
CTAAAACTGTCTGTTAGACCCAAACCGCCAACCGGTGCGCAACACACGAG

GCAAGATTTGCATAGATGACCGAGATTCCCCGAAAGTCAGTCAATACGTG          2900
CGTTCTAAACGTATCTACTGGCTCTAAGGGGCTTTCAGTCAGTTATGCAC

TGCATTCACACAAAGAAGTCGCTCGAATCCCTCCGACTATTCTCCACATC          2950
ACGTAAGTGTGTTTCTTCAGCGAGCTTAGGGAGGCTGATAAGAGGTGTAG

ATCGCGAGCATCAGGTGTGGTGTCTGGAATTCAGGAAGGTACACGCCGAA          3000
TAGCGCTCGTAGTCCACACCACAGACCTTAAGTCCTTCCATGTGCGGCTT

TGGCCTACGAATGGATTATGAACTCGCTGCTCGACGCGTGGCGTTCCAAT          3050
ACCGGATGCTTACCTAATACTTGAGCGACGAGCTGCGCACCGCAAGGTTA

CTATTCGCATCGAAACCCTACTGGACACAAAGCTTCAAGGGACAATCCAC          3100
GATAAGCGTAGCTTTGGGATGACCTGTGTTTCGAAGTTCCCTGTTAGGTG

GTTTAGTACGCTTTATCAAGAGGCGTATAATCATTATGCGATTATTAATG          3150
CAAATCATGCGAAATAGTTCTCCGCATATTAGTAATACGCTAATAATTAC

GGACAAGGGGAGATTGTTGGAGACTATTTGTCTACGAGCTCACGTGCCGA          3200
CCTGTTCCCCTCTAACAACCTCTGATAAACAGATGCTCGAGTGCACGGCT
```

FIG. 3D

```
ATGCTCAACGGAGCCAACCCACAAGCCACGTGGTCAGGCGYCCGACGCGT    3250
TACGAGTTGCCTCGGTTGGGTGTTCGGTGCACCAGTCCGCRGGCTGCGCA

TCGATCTACAAAAATGGACGCGGTCCGAGGAAGAGTGAGCATGCGACGCT    3300
AGCTAGATGTTTTTACCTGCGCCAGGCTCCTTCTCACTCGTACGCTGCGA

CGGCTCAACCGGACGCATTTCATCTTCATACACTGGTTAAACTACATACT    3350
GCCGAGTTGGCCTGCGTAAAGTAGAAGTATGTGACCAATTTGATGTATGA

TCTATGGATCTTTGAATTGAACAAAAAATGATTTTATTCAGAATAATGAT    3400
AGATACCTAGAAACTTAACTTGTTTTTACTAAAATAAGTCTTATTACTA

AAATACGATTATATATAAA
TTTATGCTAATATATATTT
```

FIG. 3E

```
MNEEFEGDVPMSDPFLSLVTKLDDIAPFPNNDPLDFDMEHNWQEPGPSQQ      50
PDPSIPGNQHSPPQEYYDIDGQRDVSTLHSLLNHNNDDFFSMRFSPPNFD     100
LGGGRGPSLAATQQLSGEGPASMLNPLQTSPPSGGYPPADAYRPLSLAQQ     150
LAAPAMTPHQAASLFVNTNGIDQKNFTHAMLSSPHHTSMTSQPYTEAMGH     200
INGYMSPYDQAQGPSGPSYYSQHHQSPPPHHHHHHPMPKIHENPEQVASP     250
SIEDAPETKPTHLVEPQSPKSPQNMKEELLRLLVNMSPSEVERLKNKKSG     300
ACSATNGPSRSKEKAAKIVIQETAEGDEDEDDEDSDSGETMSQGTTIIVR     350
RPKTERRTAHNLIEKKYRCSINDRIQQLKVLLCGDEAKLSKSATLRRAIE     400
HIEEVEHENQVLKHHVEQMRKTLQNNRLPYPEPIQYTEYSARSPVESSPS     450
PPRNERKRSRMSTTTPMKNGTRDGSSKVTLFAMLLAVLIFNPIGLLAGSA     500
IFSKAAAEAPIASPFEHGRVIDDPDGTSTRTLFWEGSIINMSYVWVFNIL     550
MIIYVVVKLLIHGDPVQDFMSVSWQTFVTTREKARAELNSGNLKDAQRKF     600
CECLATLDRSLPSPGVDSVFSVGWECVRHLLNWLWIGRYIARRRSTTKP      650
VSVVCRSHAQTAVLYHEIHQLHLMGITGNFEDTYEPSALTGLFMSLCAVN     700
LAEAAGASNDGLPRAVMAQIYISASIQCRLALPNLLAPFFSGYFLRRARR     750
HVRRAPEHSVSHLLWIFHPATRKFMSDAKRLEHVLSSKQKQLRFGSFVED     800
EQLSPLARIRTTLKVYLLSKLVQELVGGDEIFTKNVERILNDNDRLDDEV     850
DVVDVSRLLVTISTQCAAILTNEKDESAKFGTWISRNGDACCTWWTHVLT     900
CGIYWRSNKNELARQHYSLIRNCPPKILTDNLGLAVGHALCARKICIDDR     950
DSPKVSQYVCIHTKKSLESLRLFSTSSRASGVVSGIQEGTRRMAYEWIMN    1000
SLLDAWRSNLFASKPYWTQSFKGQSTFSTLYQEAYNHYAIINGTRGDCWR    1050
LFVYELTCRMLNGANPQATWSGXRRVRSTKMDAVRGRVSMRRSAQPDAFH    1100
LHTLVKLHTSMDL
```

FIG. 4

```
CGGCACGAGGATTAATGCTGATTTCTGGTCTGGACTACACAGCATTGCTG      50
GCCGTGCTCCTAATTACGACTAAAGACCAGACCTGATGTGTCGTAACGAC

GTATAAGGAGTCGGGACCAGAGGAGTAAGATTTCGGGAAGGAATCCCGTC     100
CATATTCCTCAGCCCTGGTCTCCTCATTCTAAAGCCCTTCCTTAGGGCAG

CGGTAGGGACTACTAGCATTCGCAAGTGACGTCCAGCAACCGGAGGACCC     150
GCCATCCCTGATGATCGTAAGCGTTCACTGCAGGTCGTTGGCCTCCTGGG

CCAACTGTAGAATCCGCATCACCATCCTAATCCCAACAAACCAATGACAT     200
GGTTGACATCTTAGGCGTAGTGGTAGGATTAGGGTTGTTTGGTTACTGTA

CTTGAGACCTCACCAGCCATGGATCCCTTCGTGTTCTTCATAGTACTGGC     250
GAACTCTGGAGTGGTCGGTACCTAGGGAAGCACAAGAAGTATCATGACCG

ATCGCTTTATGGCGTTCTTTACTTTTTCGACCGCTTCTTCAAGAGTTGCA     300
TAGCGAAATACCGCAAGAAATGAAAAAGCTGGCGAAGAAGTTCTCAACGT

TGCACTACCCGTACGATGCCTTCCTCAAGAACACCGGGCTGAGTATAAAT     350
ACGTGATGGGCATGCTACGGAAGGAGTTCTTGTGGCCCGACTCATATTTA

TTCATGAGCCTCCACTGGCACACGAGTGCCTTTAACAGGACCCTCCTACG     400
AAGTACTCGGAGGTGACCGTGTGCTCACGGAAATTGTCCTGGGAGGATGC

CTGGGGATCTGCCGGTAACAGCTGCACCCGGAGAGTAATGATCACCAGCT     450
GACCCCTAGACGGCCATTGTCGACGTGGGCCTCTCATTACTAGTGGTCGA

TTAATGTAGGAGTCCTGGTCACCTTTTCTCTGCTCCCGATCGGTCTGATC     500
AATTACATCCTCAGGACCAGTGGAAAAGAGACGAGGGCTAGCCAGACTAG

CTGCTCATTGCCACTATCTTCAGCAGTGGTGAACAAGACAGCTCTTCGTC     550
GACGAGTAACGGTGATAGAAGTCGTCACCACTTGTTCTGTCGAGAAGCAG

TGTATCCTCGCCCGTTGGAGTCCCTGTGCAGCTGGAAATTCTACTGCCCG     600
ACATAGGAGCGGGCAACCTCAGGGACACGTCGACCTTTAAGATGACGGGC

GCGTCAACTTGCCGTTGGAGGAGATCGGATACTACATCACAACCCTTGTG     650
CGCAGTTGAACGGCAACCTCCTCTAGCCTATGATGTAGTGTTGGGAACAC

CTCTGCTTGGTGGTGCACGAGATGGGACACGCCCTGGCCGCTGTGATGGA     700
GAGACGAACCACCACGTGCTCTACCCTGTGCGGGACCGGCGACACTACCT

GGATGTGCCTGTCACCGGGTTTGGAATAAAGTTCATCTTCTGCCTGCCGT     750
CCTACACGGACAGTGGCCCAAACCTTATTTCAAGTAGAAGACGGACGGCA

TAGCATACACGGAGCTCTCCCACGACCACTTAAACAGTCTACGTTGGTTC     800
ATCGTATGTGCCTCGAGAGGGTGCTGGTGAATTTGTCAGATGCAACCAAG
```

FIG. 5A

| | |
|---|---|
| CGCAAGCTACGTGTTCTGTGCGCTGGAATCTGGCATAATTTTGTGTTCGC<br>GCGTTCGATGCACAAGACACGCGACCTTAGACCGTATTAAAACACAAGCG | 850 |
| TGGCGTGTGCTATCTCTTAATCTCAACGGTGGGAATCACTATGTCACCTT<br>ACCGCACACGATAGAGAATTAGAGTTGCCACCCTTAGTGATACAGTGGAA | 900 |
| TGTACGCTTACAACCAACACGTAGTGGTCACTGAACTAACAAGGAAATCC<br>ACATGCGAATGTTGGTTGTGCATCACCAGTGACTTGATTGTTCCTTTAGG | 950 |
| CCGCTGAGGGGAGAGCGCGGCTTGCAAGTGGACAATCAAATAACCCAAGT<br>GGCGACTCCCCTCTCGCGCCGAACGTTCACCTGTTAGTTTATTGGGTTCA | 1000 |
| AAACGGCTGCCCAGTAAACAGCGAGGAGAGTTGGGTGACATGCCTGCAGA<br>TTTGCCGACGGGTCATTTGTCGCTCCTCTCAACCCACTGTACGGACGTCT | 1050 |
| ACTCTCTGAAGCTCAAGCCGGGCTACTGTGTGAGTGCGGACTTCGTGCAG<br>TGAGAGACTTCGAGTTCGGCCCGATGACACACTCACGCCTGAAGCACGTC | 1100 |
| CTTAACGACGAAAGCAGCGCCATCTCACATCATAGCATTGATGGTCAGCT<br>GAATTGCTGCTTTCGTCGCGGTAGAGTGTAGTATCGTAACTACCAGTCGA | 1150 |
| ACAGTGCTGTGATGAACTAAATCCGAACGTAAGCTGCTTCGAGGTGGTGG<br>TGTCACGACACTACTTGATTTAGGCTTGCATTCGACGAAGCTCCACCACC | 1200 |
| AGGACGCAAATGGAGATGTGCCGGTGGAGCTGCCGCAGCATGTATGTCTC<br>TCCTGCGTTTACCTCTACACGGCCACCTCGACGGCGTCGTACATACAGAG | 1250 |
| AATGTGCGCCGCACTTTGGAGGAGGTCTCCGAGCACTGCTCGTCCGGAGT<br>TTACACGCGGCGTGAAACCTCCTCCAGAGGCTCGTGACGAGCAGGCCTCA | 1300 |
| TTGCAACGAGGGATTCTGCCTACGACCGCTTATACGAAATATCACTGCCA<br>AACGTTGCTCCCTAAGACGGATGCTGGCGAATATGCTTTATAGTGACGGT | 1350 |
| TAATGACGTTCAAGCGACAGAATTTTCGCGGAGAGAAGCTGCCGCCGGTG<br>ATTACTGCAAGTTCGCTGTCTTAAAAGCGCCTCTCTTCGACGGCGGCCAC | 1400 |
| ATCTATGTGGGCCATCCATGGGATGTCACTCGAACTGTGGAGGTATCCGC<br>TAGATACACCCGGTAGGTACCCTACAGTGAGCTTGACACCTCCATAGGCG | 1450 |
| CTTTGTGCCGAGATATAGCTTATTAAAGGCAGCCTGGCCGGATGCCTGGC<br>GAAACACGGCTCTATATCGAATAATTTCCGTCGGACCGGCCTACGGACCG | 1500 |
| TGCTGCTCCTCAAGTATAACGTGGTCTTCAGCATAGGATTGGCGTTGATC<br>ACGACGAGGAGTTCATATTGCACCAGAAGTCGTATCCTAACCGCAACTAG | 1550 |
| AATGCCATTCCCTGCTTTGGTTTCGATGGCGCCCACATTACCAGCACCGT<br>TTACGGTAAGGGACGAAACCAAAGCTACCGCGGGTGTAATGGTCGTGGCA | 1600 |

FIG. 5B

```
GATACACAGCTTCTTGGTGGGCAGAGTGGATCAGCATGCCAAGAGAGATA      1650
CTATGTGTCGAAGAACCACCCGTCTCACCTAGTCGTACGGTTCTCTCTAT

TCATCTCGTTGATAATCACCAGCGTGGGTTCCCTTCTCTTTGCACTGGCC      1700
AGTAGAGCAACTATTAGTGGTCGCACCCAAGGGAAGAGAAACGTGACCGG

CTGCTTAAGGTGGCCTGGTTGAGTTTTCTGCGACCCCTGCTTTAAGAACT      1750
GACGAATTCCACCGGACCAACTCAAAAGACGCTGGGACGAAATTCTTGA

GAAATGGAAAACTGAAATGGATCCTGGGAGTTCAACTCCCTGCAAAGACG      1800
CTTTACCTTTTGACTTTACCTAGGACCCTCAAGTTGAGGGACGTTTCTGC

CTAGACTGCTATTTCACCTTCACGAAACACACAAAAACACAGCGAATTGT      1850
GATCTGACGATAAAGTGGAAGTGCTTTGTGTGTTTTGTGTCGCTTAACA

AGCACCTCAAAGATTCGATAGCTTTTTGTCATAGTCCTTAGTCTTAACTC      1900
TCGTGGAGTTTCTAAGCTATCGAAAACAGTATCAGGAATCAGAATTGAG

GTATTTATTTTCGTACGGTTGTCGAGCTCAAAAATAAAATCAAATTAAGC      1950
CATAAATAAAAGCATGCCAACAGCTCGAGTTTTTATTTTAGTTTAATTCG

TAAAAAAAAAAAAAAAAAAAC
ATTTTTTTTTTTTTTTTTTTG
```

FIG. 5C

```
MDPFVFFIVLASLYGVLYFFDRFFKSCMHYPYDAFLKNTGLSINFMSLHW      50

HTSAFNRTLLRWGSAGNSCTRRVMITSFNVGVLVTFSLLPIGLILLIATI     100

FSSGEQDSSSSVSSPVGVPVQLEILLPGVNLPLEEIGYYITTLVLCLVVH     150

EMGHALAAVMEDVPVTGFGIKFIFCLPLAYTELSHDHLNSLRWFRKLRVL     200

CAGIWHNFVFAGVCYLLISTVGITMSPLYAYNQHVVVTELTRKSPLRGER     250

GLQVDNQITQVNGCPVNSEESWVTCLQNSLKLKPGYCVSADFVQLNDESS     300

AISHHSIDGQLQCCDELNPNVSCFEVVEDANGDVPVELPQHVCLNVRRTL     350

EEVSEHCSSGVCNEGFCLRPLIRNITAIMTFKRQNFRGEKLPPVIYVGHP     400

WDVTRTVEVSAFVPRYSLLKAAWPDAWLLLLKYNVVFSIGLALINAIPCF     450

GFDGAHITSTVIHSFLVGRVDQHAKRDIISLIITSVGSLLFALALLKVAW     500

LSFLRPLL
```

FIG. 6

```
GTGTGCCTGACTGTTTTGTAGGTGTAAGGAGGGGCGTGGCCAAATAGTTT      50
CACACGGACTGACAAAACATCCACATTCCTCCCCGCACCGGTTTATCAAA

TTGGTATACGGATAGAATTTGGATGAAAAATAAAACGAAATCAAAACATT      100
AACCATATGCCTATCTTAAACCTACTTTTTATTTTGCTTTAGTTTTGTAA

TTTCAAAAGCGTGGAAGTTTTGGCCGGCTTGTGGGCATGGCAAAACGTTT      150
AAAGTTTTCGCACCTTCAAAACCGGCCGAACACCCGTACCGTTTTGCAAA

TTTGGCTATCCGTTAATCAACATACCGTTGCCCGGGACAATACCCACCAA      200
AAACCGATAGGCAATTAGTTGTATGGCAACGGGCCCTGTTATGGGTGGTT

GATCGTTGTACCCTACGAAACTGGATCCGGATCGCTGTCATGGCACTCTC      250
CTAGCAACATGGATGCTTTGACCTAGGCCTAGCGACAGTACCGTGAGAG

TTAATACATCCTCGACTACACCGCAGGAACCGCACCCTTCCGGCGAACCC      300
AATTATGTAGGAGCTGATGTGGCGTCCTTGGCGTGGGAAGGCCGCTTGGG

TGGCCCCCCGAACCACAGGTACTCAATAGCAGTACCACGGACCGCAGCCC      350
ACCGGGGGGCTTGGTGTCCATGAGTTATCGTCATGGTGCCTGGCGTCGGG

GCCTCCCCTTCTGCCCTGGGCGCAGAGCAGCCCCGCCTTTTTCTACGTCC      400
CGGAGGGGAAGACGGGACCCGCGTCTCGTCGGGGCGGAAAAAGATGCAGG

AGCAGATTACTCTGCGAACCAGTGTTCTCCCGTGGACGGAGGGAATGCAG     450
TCGTCTAATGAGACGCTTGGTCACAAGAGGGCACCTGCCTCCCTTACGTC

CTTATGGATGCGTTTCGTGCGCCGCTACACGAAGTTTTTAAATTGCTTGA     500
GAATACCTACGCAAAGCACGCGGCGATGTGCTTCAAAAATTTAACGAACT

AATTGTGCGCAATCACCAGAGCAGCGAAAACAAACGTACCCTGGAGCACA     550
TTAACACGCGTTAGTGGTCTCGTCGCTTTTGTTTGCATGGGACCTCGTGT

ACTGCCTACATGTAGACAACGTAAAGCGCGGAACACACGGGCAGCTGGAC     600
TGACGGATGTACATCTGTTGCATTTCGCGCCTTGTGTGCCCGTCGACCTG

CAGATCTTTCCGGAGTATGGCTGCCTGCTGCTCTCGCCCGCCAACCTGTG     650
GTCTAGAAAGGCCTCATACCGACGGACGACGAGAGCGGGCGGTTGGACAC

GACGCAGAACTCTCAGAACTTTACTCGGGACACAAACATCCTGAACACGA     700
CTGCGTCTTGAGAGTCTTGAAATGAGCCCTGTGTTTGTAGGACTTGTGCT

TATTTCAGTACCATAACCTACAGAAATCAAAAGTTTCCGCGGCGGAAATG     750
ATAAAGTCATGGTATTGGATGTCTTTAGTTTTCAAAGGCGCCGCCTTTAC

CTGTTTGGATTACCCATGCAGGACACTGGATTCAAGCGCTATCCATTGCG     800
GACAAACCTAATGGGTACGTCCTGTGACCTAAGTTCGCGATAGGTAACGC
```

FIG. 7A

```
CGCTCGGTCGCGTATTATACAGTATGCCTTGACGTTATTCCTCAAGCACA    850
GCGAGCCAGCGCATAATATGTCATACGGAACTGCAATAAGGAGTTCGTGT

ACGATATGGAGTATCTGGACACTCTAAAGGAAAAGCTGCTGCGACACTAT    900
TGCTATACCTCATAGACCTGTGAGATTTCCTTTTCGACGACGCTGTGATA

CCCCCACTCCCGTTGGCTAGTGCGTCGGCTGAAGAGCCGACGACCATAAC    950
GGGGGTGAGGGCAACCGATCACGCAGCCGACTTCTCGGCTGCTGGTATTG

TTACATCTTTTATCCAGGAGAGTACAGGATGTGGGAGCTGGTGCCTTACA    1000
AATGTAGAAAATAGGTCCTCTCATGTCCTACACCCTCGACCACGGAATGT

CAGTGGCCTTTATGTTGGTGTTTGCTTATGTGTACTTCTCTGTTCGAAAA    1050
GTCACCGGAAATACAACCACAAACGAATACACATGAAGAGACAAGCTTTT

ATCGATGTATTTCGTTCCCGCTTTTTGCTGGCCTTATGTAGCGTAATCAC    1100
TAGCTACATAAAGCAAGGGCGAAAAACGACCGGAATACATCGCATTAGTG

CACAGCCGGGAGCTTGGCCATGTCCCTTGGCTTGTGTTTCTTCTTTGGCC    1150
GTGTCGGCCCTCGAACCGGTACAGGGAACCGAACACAAAGAAGAAACCGG

TGACAATTTCGCTGCAGTCAAAGGACATTTTCCCCTACCTTGTAATCCTT    1200
ACTGTTAAAGCGACGTCAGTTTCCTGTAAAAGGGGATGGAACATTAGGAA

GTGGGATTGGAAAATAGCTTGGTGATCACAAAGAGCGTAGTCTCAATGGA    1250
CACCCTAACCTTTTATCGAACCACTAGTGTTTCTCGCATCAGAGTTACCT

CGAGACATTCGACGTGAAGATCCGCGTGGCGCAGGCTCTTAGCAAGGAGG    1300
GCTCTGTAAGCTGCACTTCTAGGCGCACCGCGTCCGAGAATCGTTCCTCC

GTTGGCATATATCCAAGACTCTTTTGACGGAGATAACAATTTTGACAATT    1350
CAACCGTATATAGGTTCTGAGAAAACTGCCTCTATTGTTAAAACTGTTAA

GGTCTTGCTACTTTCGTGCCCGTCATCCAGGAGTTTTGTATCTTTGCCAT    1400
CCAGAACGATGAAAGCACGGGCAGTAGGTCCTCAAAACATAGAAACGGTA

AGTCGGCTTGCTTTCCGATTTTATGCTACAGATGCTGCTCTTCTCAACAA    1450
TCAGCCGAACGAAAGGCTAAAATACGATGTCTACGACGAGAAGAGTTGTT

TACTGGCCATGAACATTAAGCGGACCGAGTATACGGCGGAGGCCAAGCAC    1500
ATGACCGGTACTTGTAATTCGCCTGGCTCATATGCCGCCTCCGGTTCGTG

CTTCCTAAGATGTTGCTGAGCTGCACCCAAGGGGCTGGTCGACAGGATTT    1550
GAAGGATTCTACAACGACTCGACGTGGGTTCCCCGACCAGCTGTCCTAAA

CCGATTTTTCGGGGCCGCCCCAGCACTGCCACCGTTTGTCCCTGGCACAT    1600
GGCTAAAAAGCCCCGGCGGGGTCGTGACGGTGGCAAACAGGGACCGTGTA
```

FIG. 7B

```
TTCAGCGTTCTCAGTCGCATCCAAAACTGTGTTTTGCTGATCCCGCATCT          1650
AAGTCGCAAGAGTCAGCGTAGGTTTTGACACAAAACGACTAGGGCGTAGA

GTTAGCGATCGTACAAGCTTGGTTAATGGACACTCGTCGCCGGAGCAACG          1700
CAATCGCTAGCATGTTCGAACCAATTACCTGTGAGCAGCGGCCTCGTTGC

AATACCCAAACGCATAAAGATTGTAAATTTCTGGGCGCGGACTCGCTTTT          1750
TTATGGGTTTGCGTATTTCTAACATTTAAAGACCCGCGCCTGAGCGAAAA

TTCAGCGTGCCTTCATGATCTGGATGATTGTGTGGATATGCTCTATAGTT          1800
AAGTCGCACGGAAGTACTAGACCTACTAACACACCTATACGAGATATCAA

TATAATTCGGGATATCTGGAGCAGTTGTTTAGCATGCAGAGCAACGGCAC          1850
ATATTAAGCCCTATAGACCTCGTCAACAAATCGTACGTCTCGTTGCCGTG

AATGACGGCAACCCTTGAACTTCAACGGCGACTACAGGCGGGTCGGGGAG          1900
TTACTGCCGTTGGGAACTTGAAGTTGCCGCTGATGTCCGCCCAGCCCCTC

CAGTCAGCAGTTTTTTCGAGGGATGGCAAGCGGACGGGCAGCGTGCCACG          1950
GTCAGTCGTCAAAAAAGCTCCCTACCGTTCGCCTGCCCGTCGCACGGTGC

AGTGCGCCAAGCGGAAGCGGCTTTTCTACGCCAATAAAAGCTCCTCTAGC          2000
TCACGCGGTTCGCCTTCGCCGAAAAGATGCGGTTATTTTCGAGGAGATCG

GATCGATATAAACGAAACGGCCGAGGAAATGATGAGACTTCGATATCCCA          2050
CTAGCTATATTTGCTTTGCCGGCTCCTTTACTACTCTGAAGCTATAGGGT

GCTTCGACCTAAACTATTTCCTTTCAAACTTCCACTGGTCCACGATTATG          2100
CGAAGCTGGATTTGATAAAGGAAAGTTTGAAGGTGACCAGGTGCTAATAC

AAACAGTACAACATCTCACTAAGTGGGCACTACGTTACCCTGCTACCGAC          2150
TTTGTCATGTTGTAGAGTGATTCACCCGTGATGCAATGGGACGATGGCTG

CATTCGCCTTAGTCATGCCATCGCTCCGGAGCTAGCCACTCTGTTGCGGA          2200
GTAAGCGGAATCAGTACGGTAGCGAGGCCTCGATCGGTGAGACAACGCCT

ATCCGCAGGAGCAGCTGCAACAAAATTTTCAATGGAAGGCCCTAGCCGCT          2250
TAGGCGTCCTCGTCGACGTTGTTTTAAAAGTTACCTTCCGGGATCGGCGA

GCACTCGATCCGCTGGACTTTAACGATGACGACGTGCGCCGTGAGTCTCC          2300
CGTGAGCTAGGCGACCTGAAATTGCTACTGCTGCACGCGGCACTCAGAGG

GATGGTAATGGCAGAGGGGTTGCCTCTGGTTCCCAAGAGCCCCATGGAAA          2350
CTACCATTACCGTCTCCCCAACGGAGACCAAGGGTTCTCGGGGTACCTTT

TATTTTTCGCCATCCTCTTGTGCTGCATCAGCATCTTCGTGCTTTGCTAC          2400
ATAAAAAGCGGTAGGAGAACACGACGTAGTCGTAGAAGCACGAAACGATG
```

FIG. 7C

```
ACGATGGTGGTTTTCTACCGCTGCATATGTACCAGGAACTATGCCGAGTG    2450
TGCTACCACCAAAAGATGGCGACGTATACATGGTCCTTGATACGGCTCAC

GCGCTCCAGTTGGCACGAATCTGAGGCACCGTACAAGCAGACTGAGCAAA    2500
CGCGAGGTCAACCGTGCTTAGACTCCGTGGCATGTTCGTCTGACTCGTTT

TCCTGGAGGGAGTTCCAACGCAAATCGCCGGACACAAACATCGCATTGAA    2550
AGGACCTCCCTCAAGGTTGCGTTTAGCGGCCTGTGTTTGTAGCGTAACTT

TGCCTGGTGTCTGACGGCGCCTACATAATCAGCTGCTGCCTTAAAGGCCA    2600
ACGGACCACAGACTGCCGCGGATGTATTAGTCGACGACGGAATTTCCGGT

AATCCGAGTGTGGGATGCACGCAGTGGCGAGCAGCTAACCAGCATCTCCC    2650
TTAGGCTCACACCCTACGTGCGTCACCGCTCGTCGATTGGTCGTAGAGGG

GATCCGATATTCAGATCTCTCAGCAGCGGACGGATGGGCAGACGCTGGTA    2700
CTAGGCTATAAGTCTAGAGAGTCGTCGCCTGCCTACCCGTCTGCGACCAT

CGAAAGCTGGCCGTGTCACCGGTCTGGTGCCTTGACTACTTCGATAATCT    2750
GCTTTCGACCGGCACAGTGGCCAGACCACGGAACTGATGAAGCTATTAGA

AATCGCAGTAGGCTGCGCCAACGGCCGCGTAGAATTGTGGGAATCCCCTG    2800
TTAGCGTCATCCGACGCGGTTGCCGGCGCATCTTAACACCCTTAGGGGAC

CGGGATTGCTTAAGTGTGCATACCAGGAAGACGCGAAGAGAAACCAGGGT    2850
GCCCTAACGAATTCACACGTATGGTCCTTCTGCGCTTCTCTTTGGTCCCA

ATAACCCACATCCACCTGAACGGCGATCGAGTGATTGTGGCGCGTCTTAA    2900
TATTGGGTGTAGGTGGACTTGCCGCTAGCTCACTAACACCGCGCAGAATT

TGGCCGACTAGATTTTTACCGCTTAGAGACGTACTACAAGGGGAAGCAAA    2950
ACCGGCTGATCTAAAAATGGCGAATCTCTGCATGATGTTCCCCTTCGTTT

TCGACTGGGGTTTTACCTCGGCTTACAGGAGAACTCATGTTCGAACTGGA    3000
AGCTGACCCCAAAATGGAGCCGAATGTCCTCTTGAGTACAAGCTTGACCT

TCCACTGGAAGCCTGGGATTAATGTTGCAGCAGCAGCGCTGTCAGCAAGA    3050
AGGTGACCTTCGGACCCTAATTACAACGTCGTCGTCGCGACAGTCGTTCT

AGCATCCCAGAAGACCACCAAGGAGGAAATGAAAATCACATTGGAGGGTG    3100
TCGTAGGGTCTTCTGGTGGTTCCTCCTTTACTTTTAGTGTAACCTCCCAC

TAAGACTAGCCCATCAGCAGCCAATCACATGCATGCAGGTCGTTAACGAC    3150
ATTCTGATCGGGTAGTCGTCGGTTAGTGTACGTACGTCCAGCAATTGCTG

ATGGTTTTCACTGGCAGCCAGGATCACACCCTCAAGGTGTATTGCCTCAA    3200
TACCAAAAGTGACCGTCGGTCCTAGTGTGGGAGTTCCACATAACGGAGTT
```

FIG. 7D

```
TAAGTCGGATGTTGAGTATACGCTCCACGGTCACTGTGGGCCTGTAACCT        3250
ATTCAGCCTACAACTCATATGCGAGGTGCCAGTGACACCCGGACATTGGA

GTCTCTTTGTGGATCGCTGGCAACCTGGCACAGGGGGGTCTGGGTCCCAG        3300
CAGAGAAACACCTAGCGACCGTTGGACCGTGTCCCCCCAGACCCAGGGTC

GACGGCCTGCTCTGCGTATGGGATCTGTTCACGGGAGCCTGCATGTATAA        3350
CTGCCGGACGAGACGCATACCCTAGACAAGTGCCCTCGGACGTACATATT

TATACAAGCTCACGACGGAGCCGTCAGCTGCCTGGCCTGTGCGCCCAGTT        3400
ATATGTTCGAGTGCTGCCTCGGCAGTCGACGGACCGGACACGCGGGTCAA

ACGTAATCTCGCTAGGCACGGACGAGAGGATTTGCGTATGGGAACGATTT        3450
TGCATTAGAGCGATCCGTGCCTGCTCTCCTAAACGCATACCCTTGCTAAA

CAGGGAAACCTGTTGACTACCATCAACATCTCAAACGCATACTCGAGCCT        3500
GTCCCTTTGGACAACTGATGGTAGTTGTAGAGTTTGCGTATGAGCTCGGA

ACTGATGCTAACACCGTCACTATTGGTTACGAGCAAAATGGGTAAGGCCT        3550
TGACTACGATTGTGGCAGTGATAACCAATGCTCGTTTTACCCATTCCGGA

CATTCTTGATTGCCAATATAAGAGGGACAGTAAATAATAAATTTAATTCC        3600
GTAAGAACTAACGGTTATATTCTCCCTGTCATTTATTATTTAAATTAAGG

AACACAGGATCTCTTATTGTGTGGGATGTGCGCACTGGGCAGCCGGCTCG        3650
TTGTGTCCTAGAGAATAACACACCCTACACGCGTGACCCGTCGGCCGAGC

CGAGGTCAAACTGGACTTTGCAAACCTGCAGCTCTGTCCCAAAATAATGA        3700
GCTCCAGTTTGACCTGAAACGTTTGGACGTCGAGACAGGGTTTTATTACT

TGCTTGCCTGCGATTCGGTAGTTTGCGACTACGGAAATGAGATCCGCGTC        3750
ACGAACGGACGCTAAGCCATCAAACGCTGATGCCTTTACTCTAGGCGCAG

GTCCGCTTTCCTATCGTGGCAGACAAGTGCCATTAAAGCGCAAAATTTTA        3800
CAGGCGAAAGGATAGCACCGTCTGTTCACGGTAATTTCGCGTTTTAAAAT

ATTTAGCGTGGTTCGCTAGCACCTAGGAATAAGTTGACTTAAGGCTTTAA        3850
TAAATCGCACCAAGCGATCGTGGATCCTTATTCAACTGAATTCCGAAATT

AACGCCTGGAAGTCATTGACGCATTCACTATTTTATATAAATATATACAC        3900
TTGCGGACCTTCAGTAACTGCGTAAGTGATAAAATATATTTATATATGTG

TATTAGGGTCCGCAGCAACTTACGGTTTTAACACAAGCTGTACGTATCTC        3950
ATAATCCCAGGCGTCGTTGAATGCCAAAATTGTGTTCGACATGCATAGAG

ATCTCTAGAATTTTGTGTTAGTTTGTGGACACTAAGTGTAACAGCTACGC        4000
TAGAGATCTTAAAACACAATCAAACACCTGTGATTCACATTGTCGATGCG
```

FIG. 7E

```
TCCGGTAGGTTAAGGAACTAAACTAAATGAATCAGATATATACACATATA    4050
AGGCCATCCAATTCCTTGATTTGATTTACTTAGTCTATATATGTGTATAT

TTTTCGCGTAATTATATAAACTACATAGTGTCTTAAAGCGCCTCAGCCTA    4100
AAAAGCGCATTAATATATTTGATGTATCACAGAATTTCGCGGAGTCGGAT

ATATAAAATGACTAAATGTTAAAATAAA
TATATTTTACTGATTTACAATTTTATTT
```

FIG. 7F

```
MKNKTKSKHFSKAWKFWPACGHGKTFFGYPLINIPLPGTIPTKIVVPYET      50
GSGSLSWHSLNTSSTTPQEPHPSGEPWPPEPQVLNSSTTDRSPPPLLPWA      100
QSSPAFFYVQQITLRTSVLPWTEGMQLMDAFRAPLHEVFKLLEIVRNHQS      150
SENKRTLEHNCLHVDNVKRGTHGQLDQIFPEYGCLLLSPANLWTQNSQNF      200
TRDTNILNTIFQYHNLQKSKVSAAEMLFGLPMQDTGFKRYPLRARSRIIQ      250
YALTLFLKHNDMEYLDTLKEKLLRHYPPLPLASASAEEPTTITYIFYPGE      300
YRMWELVPYTVAFMLVFAYVYFSVRKIDVFRSRFLLALCSVITTAGSLAM      350
SLGLCFFFGLTISLQSKDIFPYLVILVGLENSLVITKSVVSMDETFDVKI      400
RVAQALSKEGWHISKTLLTEITILTIGLATFVPVIQEFCIFAIVGLLSDF      450
MLQMLLFSTILAMNIKRTEYTAEAKHLPKMLLSCTQGAGRQDFRFFGAAP      500
ALPPFVPGTFQRSQSHPKLCFADPASVSDRTSLVNGHSSPEQRIPKRIKI      550
VNFWARTRFFQRAFMIWMIVWICSIVYNSGYLEQLFSMQSNGTMTATLEL      600
QRRLQAGRGAVSSFFEGWQADGQRATSAPSGSGFSTPIKAPLAIDINETA      650
EEMMRLRYPSFDLNYFLSNFHWSTIMKQYNISLSGHYVTLLPTIRLSHAI      700
APELATLLRNPQEQLQQNFQWKALAAALDPLDFNDDDVRRESPMVMAEGL      750
PLVPKSPMEIFFAILLCCISIFVLCYTMVVFYRCICTRNYAEWRSSWHES      800
EAPYKQTEQILEGVPTQIAGHKHRIECLVSDGAYIISCCLKGQIRVWDAR      850
SGEQLTSISRSDIQISQQRTDGQTLVRKLAVSPVWCLDYFDNLIAVGCAN      900
GRVELWESPAGLLKCAYQEDAKRNQGITHIHLNGDRVIVARLNGRLDFYR      950
LETYYKGKQIDWGFTSAYRRTHVRTGSTGSLGLMLQQQRCQQEASQKTTK      1000
EEMKITLEGVRLAHQQPITCMQVVNDMVFTGSQDHTLKVYCLNKSDVEYT      1050
LHGHCGPVTCLFVDRWQPGTGGSGSQDGLLCVWDLFTGACMYNIQAHDGA      1100
VSCLACAPSYVISLGTDERICVWERFQGNLLTTINISNAYSSLLMLTPSL      1150
LVTSKMGKASFLIANIRGTVNNKFNSNTGSLIVWDVRTGQPAREVKLDFA      1200
NLQLCPKIMMLACDSVVCDYGNEIRVVRFPIVADKCH
```

FIG. 8

```
GTTTATTAAGCTGCAAATATACTCGTGAAAAAAATCAAAACAACCATGAA        50
CAAATAATTCGACGTTTATATGAGCACTTTTTTAGTTTTGTTGGTACTT

CAACAAGTGTTGCAACTATTACTAACTAGTCGCTAGTTTAAAGCAAAGTG       100
GTTGTTCACAACGTTGATAATGATTGATCAGCGATCAAATTTCGTTTCAC

CGTTGACATTAACCAGTTATGGAAAAACAAAAGCACACGTGAACTAAGAA       150
GCAACTGTAATTGGTCAATACCTTTTGTTTTCGTGTGCACTTGATTCTT

AACAGATAGAAGGTGGTAAAGCATTCGCAATGGACACGACACTGATGAAC       200
TTGTCTATCTTCCACCATTTCGTAAGCGTTACCTGTGCTGTGACTACTTG

TTAATAGACGCTCCGCTGGACGAGTCCATGGATTTGTTCAAAGCGGAGGA       250
AATTATCTGCGAGGCGACCTGCTCAGGTACCTAAACAAGTTTCGCCTCCT

TGTCTTCGAACCGTTCGACGCCGACCTGCACTCGGACATGCTGGACATCA       300
ACAGAAGCTTGGCAAGCTGCGGCTGGACGTGAGCCTGTACGACCTGTAGT

TCCTCAACGACATGGACCTGGCGCCGACGCAGATGTACAACATGCTGCTG       350
AGGAGTTGCTGTACCTGGACCGCGGCTGCGTCTACATGTTGTACGACGAC

GACGAGCCTCGAACGCATACCCAGCAGACGCAGTCCGTGGATCAGCAGCC       400
CTGCTCGGAGCTTGCGTATGGGTCGTCTGCGTCAGGCACCTAGTCGTCGG

GCAATCCGTCGAGCAACAGCCGCACGTGAAAAGCGAGCACTCTTCGCCAG       450
CGTTAGGCAGCTCGTTGTCGGCGTGCACTTTTCGCTCGTGAGAAGCGGTC

TGCACATCAAGGAGGAACTGCATCAGCAGCAACAACAGTCGCCGCTTCTC       500
ACGTGTAGTTCCTCCTTGACGTAGTCGTCGTTGTTGTCAGCGGCGAAGAG

GTCTACAAACCAGATCCCCTCATAGCCACAAGCTACAATTGTCCCCAGCA       550
CAGATGTTTGGTCTAGGGAGTATCGGTGTTCGATGTTAACAGGGGTCGT

ACAGCCGACGGGCCTTTTGAAGGCCGCCCAACCAACAGCCACCATACATC       600
TGTCGGCTGCCCGGAAAACTTCCGGCGGGTTGGTTGTCGGTGGTATGTAG

ACATGGACGCCCAGCGGATGCCGCCGAACACGGCGGTGTATCCCCATCT       650
TGTACCTGCGGGTCGCCTACGGCGGCTTGTGCCGCCACATAGGGGTAGA

CTGGGCAGTAGCTTTGTCTACCAGTCCATGTCCCCGCCCACGTCGCCGGT       700
GACCCGTCATCGAAACAGATGGTCAGGTACAGGGCGGGTGCAGCGGCCA

GGAGTCTGCGAACCAGAATGTCAATGTCATGCAGCCCGTTGCTGCAACTC       750
CCTCAGACGCTTGGTCTTACAGTTACAGTACGTCGGGCAACGACGTTGAG

CTGCTCCCGCTTCTGCTCCTTTGCCCCAGCAGTCGTATCCGCAACCCTTC       800
GACGAGGGCGAAGACGAGGAAACGGGGTCGTCAGCATAGGCGTTGGGAAG
```

FIG. 9A

```
ATTACGTACAACTCTAAGGCCGGAATGACTTCCGATGAAGCCATGTACTT      850
TAATGCATGTTGAGATTCCGGCCTTACTGAAGGCTACTTCGGTACATGAA

GCTCTTGCAGCCCACGGTAGCCAGTCCAACCCCATCTCCACCTGTGGCTC      900
CGAGAACGTCGGGTGCCATCGGTCAGGTTGGGGTAGAGGTGGACACCGAG

CACCACCGACAAGCACAGGTAGTCGGGCCAGCAAGTGCGAGTGGCACCA       950
GTGGTGGCTGTTCGTGTCCATCAGCCCGGTCGTTCCACGCTCACCGTGGT

CTGGCTCCGTCACCTGCCGCTATGGAAGTCCAGGGCAAGGTACCTATCAA     1000
GACCGAGGCAGTGGACGGCGATACCTTCAGGTCCCGTTCCATGGATAGTT

CCGGGTTCAACCCAAGGTGAAGGAAGTAAAGCGCTCGGCCCACAACGCCA     1050
GGCCCAAGTTGGGTTCCACTTCCTTCATTTCGCGAGCCGGGTGTTGCGGT

TCGAGCGGCGCTATCGCACCTCAATCAACGACAAGATTAACGAGTTGAAG     1100
AGCTCGCCGCGATAGCGTGGAGTTAGTTGCTGTTCTAATTGCTCAACTTC

AACTTGGTAGTGGGAGAGCAGGCCAAGCTGAACAAGTCCGCAGTGTTGCG     1150
TTGAACCATCACCCTCTCGTCCGGTTCGACTTGTTCAGGCGTCACAACGC

GAAATCCATAGACAAGATTCGGGATCTGCAACGCCAGAATCACGATCTGA     1200
CTTTAGGTATCTGTTCTAAGCCCTAGACGTTGCGGTCTTAGTGCTAGACT

AGGCAGAGTTGCAGCGCCTGCAGAGGGAGCTAATGGCACGCGACGGCTCC     1250
TCCGTCTCAACGTCGCGGACGTCTCCCTCGATTACCGTGCGCTGCCGAGG

AAGGTGAAGGATTTACTTCAGCTGGGCACTCGGCCTGGTAGAGCATCCAA     1300
TTCCACTTCCTAAATGAAGTCGACCCGTGAGCCGGACCATCTCGTAGGTT

GAAGCGCCGCGAGAGCTCGCAGACCTTTACCACGGATGCCGGACTGACGC     1350
CTTCGCGGCGCTCTCGAGCGTCTGGAAATGGTGCCTACGGCCTGACTGCG

CGCCACGCAGCGATGAATCGGATCCTTCGCTCTCGCCCATGCACTCGGAC     1400
GCGGTGCGTCGCTACTTAGCCTAGGAAGCGAGAGCGGGTACGTGAGCCTG

ATCTCGTTGCCGCCATCACCCTATGGTGGATCCACCGCCAGCTGTAGCAG     1450
TAGAGCAACGGCGGTAGTGGGATACCACCTAGGTGGCGGTCGACATCGTC

TGGCAGCAGCAGCAGCAATGAAGAACCACTGGTGGTGCCCAGCTCTATGC     1500
ACCGTCGTCGTCGTCGTTACTTCTTGGTGACCACCACGGGTCGAGATACG

GCGGCATGGCCACCCACTCTCGCCTCGGACTCTGCATGTTTATGTTCGCC     1550
CGCCGTACCGGTGGGTGAGAGCGGAGCCTGAGACGTACAAATACAAGCGG

ATCCTGGCCGTCAATCCCTTCAAGACCTTTCTCCAGCGCGGCCACTATGA     1600
TAGGACCGGCAGTTAGGGAAGTTCTGGAAAGAGGTCGCGCCGGTGATACT
```

FIG. 9B

```
CAGTAATGACGATCTTGGCGACATGAGCGGTCAAAGACGCATTCTCTCTT    1650
GTCATTACTGCTAGAACCGCTGTACTCGCCAGTTTCTGCGTAAGAGAGAA

ACGACGTGGAAGGTGAAGGTTTTGCTGTCTGGCAGCAGAGTTCCTGGATA    1700
TGCTGCACCTTCCACTTCCAAAACGACAGACCGTCGTCTCAAGGACCTAT

TGGCTATTGAACTTCACACTGATGCTTGGATGCTTGGTGAAATTGCTGGT    1750
ACCGATAACTTGAAGTGTGACTACGAACCTACGAACCACTTTAACGACCA

TTACGGTGATCCGCAGCTGGACGCGCAAACGGACGCCTACTGCCAGCACA    1800
AATGCCACTAGGCGTCGACCTGCGCGTTTGCCTGCGGATGACGGTCGTGT

GGCAGCGGGCTGACTTCTATTTTAGCCAAGGACAGTCGTCTCAGGCCTAC    1850
CCGTCGCCCGACTGAAGATAAAATCGGTTCCTGTCAGCAGAGTCCGGATG

GCCGGTTACCTCAACTGTCTGCATATGTTTGGATTAAGTCTACCGGCGTC    1900
CGGCCAATGGAGTTGACAGACGTATACAAACCTAATTCAGATGGCCGCAG

GCGCTTGGAGTGTTACTTGCAGACCACGTGGCAGTTCCTTCGTTTTCTTT    1950
CGCGAACCTCACAATGAACGTCTGGTGCACCGTCAAGGAAGCAAAAGAAA

TCCATCGCCTCTGGCTGGGTCGGGTGCTGTCACGGCGGTCCGGTGGGCTG    2000
AGGTAGCGGAGACCGACCCAGCCCACGACAGTGCCGCCAGGCCACCCGAC

TTTAGCAACGCCGCCAGCAGGAAACAGGCGCTGGCATCTGCACGCGAACT    2050
AAATCGTTGCGGCGGTCGTCCTTTGTCCGCGACCGTAGACGTGCGCTTGA

GGCCCTGCTCTTCAACCGACTGAATCAATTGCAACTGACTGGAAATGGAA    2100
CCGGGACGAGAAGTTGGCTGACTTAGTTAACGTTGACTGACCTTTACCTT

GCCGCGGTGACATGAACGGCATTATGATGGCACTATTCGCAAGCAACATG    2150
CGGCGCCACTGTACTTGCCGTAATACTACCGTGATAAGCGTTCGTTGTAC

GCTGAAGTGGCGCACAATCTACTGACACCGCGCGAGACCATCTGCATCCA    2200
CGACTTCACCGCGTGTTAGATGACTGTGGCGCGCTCTGGTAGACGTAGGT

CGTAATGACAGCGTTGCGAATGAAGCGCAGTGCCCCAAAATGGTTGCAAC    2250
GCATTACTGTCGCAACGCTTACTTCGCGTCACGGGGTTTTACCAACGTTG

AGTTCTTCGCCCGATACTACATGAGCCGGGCTCGTCAAGAGTGCGGTCGC    2300
TCAAGAAGCGGGCTATGATGTACTCGGCCCGAGCAGTTCTCACGCCAGCG

ACTAGGGCCACCGAGCAAACGCAGGAGCTACGTTGGGCATTCACAGCCTA    2350
TGATCCCGGTGGCTCGTTTGCGTCCTCGATGCAACCCGTAAGTGTCGGAT

TGGATATCGCTACTGCGCCACGCACGTCTTCACGTACGATCTGAGCGACT    2400
ACCTATAGCGATGACGCGGTGCGTGCAGAAGTGCATGCTAGACTCGCTGA
```

FIG. 9C

```
CCGGCGAGCAGGATGGATTCTTCACACGTCTTAGGAATCCATGTGATCCC        2450
GGCCGCTCGTCCTACCTAAGAAGTGTGCAGAATCCTTAGGTACACTAGGG

GCTGCCCACGTCATTAAGCAATATCGAGAGCATTTGCTGTTTAAATCCAT        2500
CGACGGGTGCAGTAATTCGTTATAGCTCTCGTAAACGACAAATTTAGGTA

TCAGTGTCTGGTAGGAGCGGGCCACAAATCGGGAGGCCTGCCCACATCTT        2550
AGTCACAGACCATCCTCGCCCGGTGTTTAGCCCTCCGGACGGGTGTAGAA

CTGTCAGCGGAGAGGCGGAACAGTTGCAGCAACAGCAGCACAGCGGCACC        2600
GACAGTCGCCTCTCCGCCTTGTCAACGTCGTTGTCGTCGTGTCGCCGTGG

ATTGTCAGCAATGTTCTTAAGTACACGTCCCTCCTTAAGGACACTCTCTG        2650
TAACAGTCGTTACAAGAATTCATGTGCAGGGAGGAATTCCTGTGAGAGAC

GGCTGATGAGGATGAGCGGGATACAAACGTGGTGTGGTGGGCCGATGTTT        2700
CCGACTACTCCTACTCGCCCTATGTTTGCACCACACCACCCGGCTACAAA

TGGAGACCGCAGTGCACTGGCTCCTTGGTGAAGACACGCTGGCCGAGCAA        2750
ACCTCTGGCGTCACGTGACCGAGGAACCACTTCTGTGCGACCGGCTCGTT

TTGTACGGCAGGATCAAGCAAATGCCCACGCAGCTGCAACAGTGCGGCGA        2800
AACATGCCGTCCTAGTTCGTTTACGGGTGCGTCGACGTTGTCACGCCGCT

AAACGATCATCTGCCCAAGGCGCTGCATGCTGTGCTGCGAGCTAAGATGA        2850
TTTGCTAGTAGACGGGTTCCGCGACGTACGACACGACGCTCGATTCTACT

TCTTACTAAAAAACAATGGCAACGCACTGGACAAAAGTCTCAAGCAATTG        2900
AGAATGATTTTTTGTTACCGTTGCGTGACCTGTTTTCAGAGTTCGTTAAC

GTAAACATCCTCTGCGATGAGTCGAGTGTGGAGCTCCAAGAGTGCTTGAC        2950
CATTTGTAGGAGACGCTACTCAGCTCACACCTCGAGGTTCTCACGAACTG

TGTCAACCGGATCACCGACGCCAAGGGTATAAAGCTGCTTTTCCAGTTGC        3000
ACAGTTGGCCTAGTGGCTGCGGTTCCCATATTTCGACGAAAAGGTCAACG

TTACCTGCGATTGGCTGCTCGAAACTAGGACTGCTCTGTGGGAACTGGAA        3050
AATGGACGCTAACCGACGAGCTTTGATCCTGACGAGACACCCTTGACCTT

CACATGAATATGGAGGACGATGGCTTCTACCAAGTGCCAGGTGAAGTGCT        3100
GTGTACTTATACCTCCTGCTACCGAAGATGGTTCACGGTCCACTTCACGA

CGAGAAGTTCCAGACCGATTTGAACTCGTTGCGCAACATTGTGGAGAATA        3150
GCTCTTCAAGGTCTGGCTAAACTTGAGCAACGCGTTGTAACACCTCTTAT

TACCGAACGCCCAATCGCGCATATATTTGTACGAGGCAGTTTGTCGCCTG        3200
ATGGCTTGCGGGTTAGCGCGTATATAAACATGCTCCGTCAAACAGCGGAC
```

FIG. 9D

```
ATGGCTGGAGCCTCACCGTGTCCAACGCAACAGCTCTTGGACAGGAGTCT     3250
TACCGACCTCGGAGTGGCACAGGTTGCGTTGTCGAGAACCTGTCCTCAGA

GCGATCACGCAACGCCCACTCGTCCATCTTCTGCGGCAGCAAGGATCGGC     3300
CGCTAGTGCGTTGCGGGTGAGCAGGTAGAAGACGCCGTCGTTCCTAGCCG

GGCAGCAGAACTTCGTGGGCGGAGAGCGGGAACGGGCTTCGGCCATGTAC     3350
CCGTCGTCTTGAAGCACCCGCCTCTCGCCCTTGCCCGAAGCCGGTACATG

GTGGCCTGCAAGTATCTCCCGCCTGCGCTGCTCAGCTCCCGGGTGAACG      3400
CACCGGACGTTCATAGAGGGCGGACGCGACGAGTCGAGGGCCCACTTGC

TGCTGGCATGTTAGCCGAGGCGGCCAAGACCCTGGAGAAGGTGGGCGACA     3450
ACGACCGTACAATCGGCTCCGCCGGTTCTGGGACCTCTTCCACCCGCTGT

AGCGAAAGCTCAAGGAGTGCTACCAGCTGATGAAGTCGCTGGGCAACGGC     3500
TCGCTTTCGAGTTCCTCACGATGGTCGACTACTTCAGCGACCCGTTGCCG

ATTGGCAGCGTGAAGGCTTAGGATAGTAGTGAAGTACATAATAAGTGGCA     3550
TAACCGTCGCACTTCCGAATCCTATCATCACTTCATGTATTATTCACCGT

CGAACGTGGTGTGGATTTTCAGCAAATGAATACCCGTTTGCTATTCAAAA     3600
GCTTGCACCACACCTAAAAGTCGTTTACTTATGGGCAAACGATAAGTTTT

GAATTACAAATGCCTAGGTCTTTATAATTACGCTATTCCTCTGTTTTCCA     3650
CTTAATGTTTACGGATCCAGAAATATTAATGCGATAAGGAGACAAAAGGT

CGCCCGGTTATGCTTAGATTGTAATTTTAAAATTATTTAATATGGACATT     3700
GCGGGCCAATACGAATCTAACATTAAAATTTAATAAATTATACCTGTAA

TTATTTGTTTATTATTTACCGTACTTGTTAAACGTATTTATAACAATAAA     3750
AATAAACAAATAATAAATGGCATGAACAATTTGCATAAATATTGTTATTT

TATTTTAACAGATTTAAA
ATAAAATTGTCTAAATTT
```

FIG. 9E

```
MDTTLMNLIDAPLDESMDLFKAEDVFEPFDADLHSDMLDIILNDMDLAPT      50
QMYNMLLDEPRTHTQQTQSVDQQPQSVEQQPHVKSEHSSPVHIKEELHQQ      100
QQQSPLLVYKPDPLIATSYNCPQQQPTGLLKAAQPTATIHHMDAQRMPPN      150
TAVYPPSLGSSFVYQSMSPPTSPVESANQNVNVMQPVAATPAPASAPLPQ      200
QSYPQPFITYNSKAGMTSDEAMYLLLQPTVASPTSPPVAPPPTSTGSRA       250
SKVRVAPLAPSPAAMEVQGKVPINRVQPKVKEVKRSAHNAIERRYRTSIN      300
DKINELKNLVVGEQAKLNKSAVLRKSIDKIRDLQRQNHDLKAELQRLQRE      350
LMARDGSKVKDLLQLGTRPGRASKKRRESSQTFTTDAGLTPPRSDESDPS      400
LSPMHSDISLPPSPYGGSTASCSSGSSSSNEEPLVVPSSMRGMATHSRLG      450
LCMFMFAILAVNPFKTFLQRGHYDSNDDLGDMSGQRRILSYDVEGEGFAV      500
WQQSSWIWLLNFTLMLGCLVKLLVYGDPQLDAQTDAYCQHRQRADFYFSQ      550
GQSSQAYAGYLNCLHMFGLSLPASRLECYLQTTWQFLRFLFHRLWLGRVL      600
SRRSGGLFSNAASRKQALASARELALLFNRLNQLQLTGNGSRGDMNGIMM      650
ALFASNMAEVAHNLLTPRETICIHVMTALRMKRSAPKWLQQFFARYYMSR      700
ARQECGRTRATEQTQELRWAFTAYGYRYCATHVFTYDLSDSGEQDGFFTR      750
LRNPCDPAAHVIKQYREHLLFKSIQCLVGAHKSGGLPTSSVSGEAEQLQ       800
QQQHSGTIVSNVLKYTSLLKDTLWADEDERDTNVVWWADVLETAVHWLLG      850
EDTLAEQLYGRIKQMPTQLQQCGENDHLPKALHAVLRAKMILLKNNGNAL      900
DKSLKQLVNILCDESSVELQECLTVNRITDAKGIKLLFQLLTCDWLLETR      950
TALWELEHMNMEDDGFYQVPGEVLEKFQTDLNSLRNIVENIPNAQSRIYL      1000
YEAVCRLMAGASPCPTQQLLDRSLRSRNAHSSIFCGSKDRRQQNFVGGER      1050
ERASAMYVACKYLPPALLSSPGERAGMLAEAAKTLEKVGDKRKLKECYQL      1100
MKSLGNGIGSVKA
```

FIG. 10

ANIMAL MODELS AND METHODS FOR ANALYSIS OF LIPID METABOLISM AND SCREENING OF PHARMACEUTICAL AND PESTICIDAL AGENTS THAT MODULATE LIPID METABOLISM

FIELD OF THE INVENTION

The present invention relates to animal models useful for the study of lipid metabolism that have been genetically modified to express or mis-express proteins involved in the sterol regulatory element binding protein (SREBP) pathway. The invention also relates to novel SREBP pathway nucleic acid and polypeptide sequences and their uses.

BACKGROUND OF THE INVENTION

Triglycerides, phospholipids, and cholesterol, which form the three major classes of lipid, perform a variety of necessary functions in cell metabolism and are vital constituents of biological membranes. However, elevated levels of lipids and/or improper lipid metabolism have been implicated in a variety of health disorders. Of particular concern mis increased blood cholesterol which leads to atherosclerosis (the deposition of cholesterol on arterial walls). This in turn may lead to heart disease, stroke or other disorders of the circulatory system. Accordingly, there is much interest within the pharmaceutical industry to understand the mechanisms involved in cholesterol synthesis and metabolism, particularly on the molecular level, so that blood cholesterol lowering drugs can be developed for the treatment or prevention of atherosclerosis.

Recent advances have been made in understanding some of the mechanisms involved in mammalian lipid metabolism. A key component is the sterol regulatory element binding protein (SREBP) pathway. SREBPs are transcription factors that activate genes involved in cholesterol and fatty acid metabolism. In the cholesterol biosynthetic pathway of vertebrates, SREBPs directly activate transcription of the genes encoding 3-hydroxy-3-methylglutaryl (HMG) coenzyme A synthase, HMG-CoA reductase, farnesyl diphosphate synthase, and squalene synthase. In the fatty acid and triglyceride biosynthetic pathways, the direct targets of SREBPs include fatty acid synthase, acetyl-CoA carboxylase, glycerol-3-phosphate acyltransferase, and acyl-CoA binding protein. Additionally, SREBPs modulate transcription of stearoyl CoA desaturase-1 and lipoprotein lipase. SREBPs also directly activate transcription of the gene encoding the low density lipoprotein (LDL) receptor, which provides cholesterol and fatty acids through receptor-mediated endocytosis. SREBPs are also implicated in the process of fat cell differentiation and adipose cell gene expression, particularly as transcription factors that can promote adipogenesis in a dominant fashion (reviewed by Spiegelman et al., Cell (1996) 87:377–389).

In high sterol conditions, SREBPs are retained as membrane-bound protein precursors that are kept inactive by virtue of being attached to the nuclear envelope and endoplasmic reticulum (ER) and therefore, excluded from the nucleus. As depicted in FIG. 1A, an SREBP in its membrane-bound form has large N-terminal and C-terminal segments facing the cytoplasm and a short loop projecting into the lumen of the organelle. The N-terminal domain is a transcription factor of the basic-helix-oop-helix-eucine zipper (bHLH-Zip) family, and contains an "acid blob" typical of many transcriptional activators. (Brown and Goldstein, Cell (1997) 89:331–340)

The N-terminal acid blob is followed by a basic helix-loop-helix-leucine zipper domain (bHLH-Zip) similar to those found in many other DNA-binding transcriptional regulators. bHLH-Zip domains have two functions: the helix-loop-helix subdomain mediates dimerization, and the basic region binds to specific DNA sequences tat include a direct repeat of 5'-PyCAPy-3'. SREBP binds to the sequence 5'-ATCACCCCAC-3' (SEQ ID NO:30) which is known as "sterol regulatory element 1" (SRE-1) and is upstream of the LDL receptor gene.

SREBPs are unique among bHLH-Zip proteins by virtue of the C-terminal domains attached to the bHLH-Zip domain. These include (from—to C-terminus): (1) a hydrophobic membrane-spanning sequence of about 20 amino acids, (2) a hydrophilic stretch of about 31 amino acids that projects into the lumen of the ER, (3) a second hydrophobic membrane-spanning domain of about 20 amino acids, and (4) a C-terminal domain which, in vertebrates, has been determined to be required for sterol regulation of SREBP cleavage.

In low sterol conditions, the acid blob/bHLH-Zip domain of SREBP is released from the membrane after which it is rapidly franslocated into the nucleus and binds specific DNA sequences to activate transcription. Two sequential proteolytic cleavages are involved. Referring to FIG. 1B, a first protease, referred to as the site 1 protease (S1P) cleaves SREBP at approximately the middle of the lumenal loop. S1P has been cloned from Chinese hamster ovary (CHO) cells (GI (GenBank Identifier No. (hereinafter "GI") 3892203) and a human cell line (GI4506774) (Sakai et al., J. Biol. Chem (1998) 273:5785–5793), and encodes a membrane bound glycoprotein of 1052 amino acids with subtilisin-like sequence features.

After cleavage at site 1, a second protease (the site 2 protease, S2P) cleaves the N-terminal fragment and releases the mature N-terminal domain into the cytosol, from which it rapidly enters the nucleus, apparently with a portion of the transmembrane domain still attached at the C-terminus. Mature, transcriptionally active SREBP is rapidly degraded in a proteosome-dependent process. This combination of proteolytic processing and rapid turnover allows the SREBP system to rapidly respond to changes in cellular membrane components. S2P homologues have been identified in both vertebrates and invertebrates and have been cloned from human cells and hamster cells (Rawson et al., Molec Cell (1997) 1:47–57). It is a membrane protein containing an HEXXH sequence characteristic of zinc metalloproteases. This family of proteins has high hydrophobicity throughout the amino acid sequence, suggesting the existence of several membrane-spanning regions.

A third component of the processing system for SREBPs is called SREBP Cleavage Activating Protein (SCAP). SCAP is a large transmembrane protein that activates S1P in low-sterol conditions. The N-terminal 730 amino acids have alternating hydrophobic and hydrophilic sequences which are predicted to form up to eight membrane spanning sequences separated by short hydrophilic stretches. This domain is strikingly similar to a domain of HMG CoA reductase (Hua et al., Cell (1996) 87:415–426) which is necessary to impart sterol regulation. In low sterol conditions, HMG-CoA reductase is quite stable, but when sterols are added the enzyme is rapidly degraded. It is believed that the membrane-spanning domain in SCAP, like its counterpart in HMG CoA reductase, can sense the levels of sterol in the ER membrane, either directly or indirectly.

The C-terminal domain of SCAP is hydrophilic and is made up of about 550 amino acids organized into four WD repeats. Recent work has demonstrated that these WD repeats bind directly to the C-terminal regulatory domain of SREBP suggesting that SCAP and SREBP are part of a stable complex in the membrane of the ER (Sakai et al., supra). It is likely that S1P and perhaps S2P are also part of the complex since SCAP is essential for activation of S1P activity. This SREBP processing complex is depicted in FIG. 2.

The involvement of the SREBP pathway in the regulation of cholesterol metabolism is of interest not only because excess blood cholesterol can lead to atherosclerosis, but also because there seem to be parallels between the processing of SREBPs and the processing of β-amyloid precursor protein which has been implicated in Alzheimer's disease (Brown and Goldstein, supra). To date, the SREBP pathway has been studied primarily using mammalian cell culture, by the isolation of mutant cells that are defective in regulation of cholesterol metabolism or intracellular cholesterol trafficking. The mutants can then serve as hosts for cloning genes by functional complementation. This has led to the molecular cloning of the S1P, S2P and SCAP genes (Rawson et al., supra; and et al., supra; and Goldstein et al., U.S. Pat. Nos. 5,527,690 and 5,891,631).

Some SREBP pathway genes have been identified in invertebrates. The isolation of a Drosophila SREBP, referred to as "HLH 106" (GI079656) has been described (Theopold et al., Proc. Natl. Acad. Sci., USA, (1996) 93(3): 1195–1199). An expressed sequence tag (EST) from *C. elegans* which has homology to S2P is described by Rawson et al., supra and is listed in GenBank (GI1559384). Additionally, GenBank has listed a protein predicted from the *C elegans* genome as having HMG-CoA reductase homology (GI3875380).

SUMMARY OF THE INVENTION

The use of invertebrate model organism genetics can greatly facilitate the elucidation of biochemical pathways, and the identification of molecules that can modulate such pathways. Accordingly, it is an object of the invention to provide invertebrate nucleic acids and polypeptides involved in the SREBP pathway. It is also an object of the invention to provide invertebrate model organisms, including novel mutant phenotypes, for the study of lipid metabolism in general, and more particularly, for the elucidation of the SREBP pathway. It is a further object of the invention to provide methods for screening molecules that modulate lipid metabolism and/or the function of genes and proteins involved in the SREBP pathway.

These and other objects are provided by flies and nematodes that have been genetically modified to express or misexpress an SREBP pathway gene, for example using transposon mutagenesis, RNA interference, chemical mutagenesis, or other genetic techniques, In certain embodiments, expression of the SREBP pathway protein is driven by a heterologous promoter that is tissue-specific, developmentally-specific, or inducible, so that the effects of the expression or mis-expression can be observed in specific tissues, at certain developmental stages, or at specified times, respectively. Additionally, the SREBP pathway protein may be linked to one or more selectable markers that allows detection of expression. Typically, the expression of the SREBP pathway protein results in an identifiable phenotype. In the case of nematodes, the invention provides novel methods for the in vivo measurement of lipid content using BODIPY-fatty acid conjugates. The animal models can be used in genetic screens to identify other genes involved in lipid metabolism. They can also be used for screening small molecule libraries directly on whole organisms for possible therapeutic or pesticide use.

The invention also provides novel isolated nucleic acids (SEQ ID NOs:1, 3, and 5). and the SREBP pathway proteins encoded thereby (SEQ ID NOs:2, 4, and 6, respectively), as well as derivatives and fragments thereof. Methods are provided for constructing vectors containing the isolated nucleic acids. Such vectors can be used for making the animal models of the invention. They can also be introduced into host cells to be used for a variety of purposes including two-hybrid screening assays, production of SREBP pathway proteins, screening small molecules that affect lipid synthesis or metabolism, etc.

BRIEF DESCRIPTION OF THE DRAWINGS

FIGS. 3A–E show a cDNA sequence that encodes *C. elegans* SREBP (SEQ ID NO:1).

FIG. 4 shows the predicted amino acid sequence (SEQ ID NO:2) of the polypeptide encoded by the *C. elegans* SREBP gene.

FIGS. 5A–C show a cDNA sequence that encodes Drosophila S2P (SEQ ID NO:3).

FIG. 6 shows the predicted amino acid sequence (SEQ ID NO:4) of the polypeptide encoded by the Drosophila S2P gene.

FIGS. 7A–7F the cDNA sequence that encodes Drosophila SCAP (SEQ ID NO:5).

FIG. 8 shows the predicted amino acid sequence (SEQ ID NO:6) of the polypeptide encoded by the Drophila SCAP gene.

FIGS. 9A–9E show the nucleic acid sequence encoding Drosophila SREBP (GI079656; SEQ ID NO:7).

FIG. 10 shows the predicted amino acid sequence (SEQ ID NO:8) of Drosophila SREBP.

DETAILED DESCRIPTION OF THE INVENTION

Figure 1B:
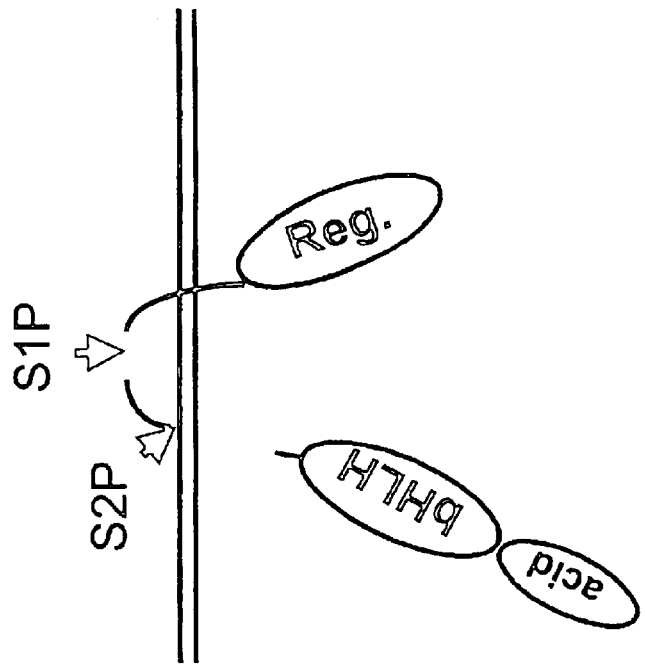
FIGS. 1A and 1B depict the inactive, membrane-bound form of SREBP (FIG. 1A) and the two-step proteolytic cleavage which activates SREBP in low sterol conditions (FIG. 1B).
Figure 1A:
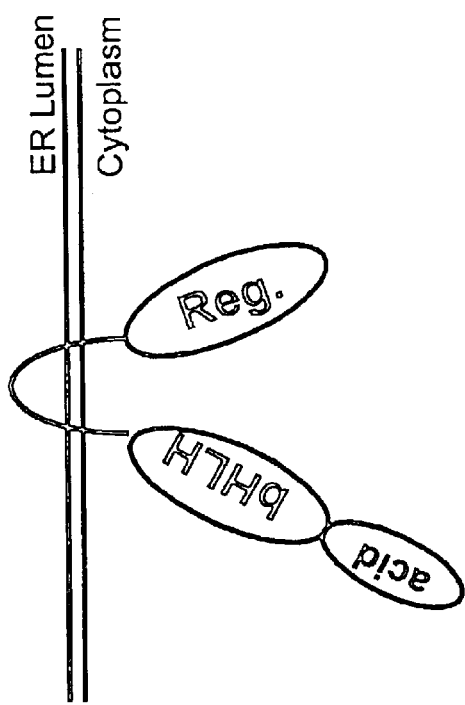
Figure 2:
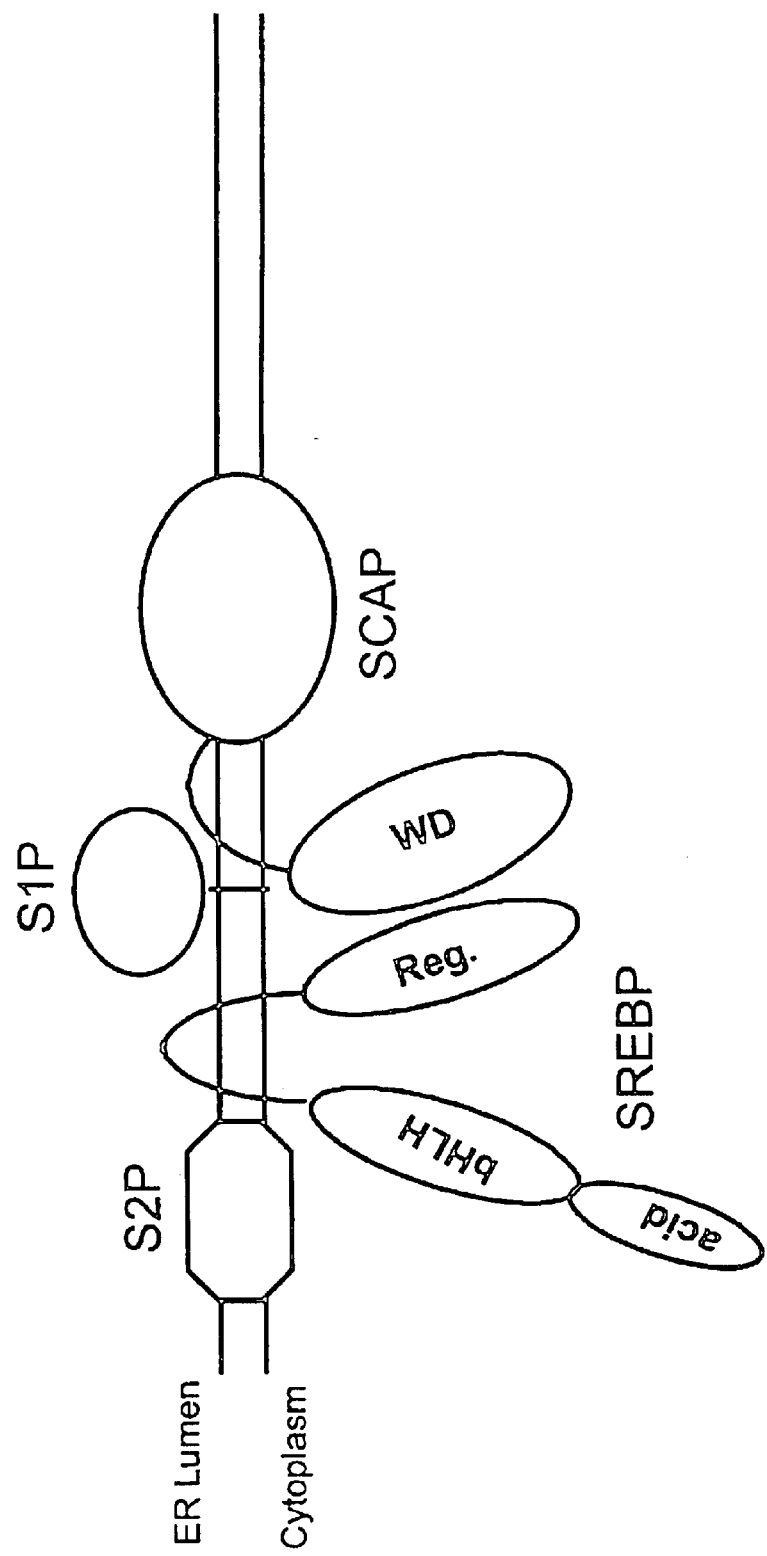
FIG. 2 depicts the presumed interactions between SREBP, SCAP, S1P and S2P in the SREBP processing complex.

The use of invertebrate model organism genetics and related technologies can greatly facilitate the elucidation of biological pathways (Scangos, Nat. Biotechnol. (1997) 15:1220–1221; Margolis and Duyk, Nat. Biotechnol. (1998) 16:311). Of particular use are the insect and nematode model organisms, *Drosophila melanogaster, and C. elegans*. An extensive search for SREBP pathway nucleic acids and their encoded proteins in *C. elegans and Drosophila melanogaster* was conducted in an attempt to identify new and useful tools for probing the function and regulation of the SREBP pathway. Novel SREBP pathway nucleic acids and their encoded proteins are identified herein. As used in this description, the term "SREBP pathway nucleic acid" refers to a nucleic acid that encodes any one of SREBP, SCAP, S1P, and S2P. The newly identified SREBP pathway nucleic acids have led to the discovery of several mutant phenotypes that can be used to study the pathways involved in lipid and fatty acid metabolism. The use of invertebrate model organisms such as *Drosophila melanogaster and C. elegans* for analyzing the expression and mis-expression of SREBP pathway proteins has great advantages over the traditional approach of using mammalian cell culture due to the ability to rapidly carry out large-scale, systematic genetic screens as well as the ability to screen small molecule libraries directly on whole organisms. Thus, the invention provides a superior approach for identifying other components involved in the synthesis, activation, control and turnover of SREBP pathway proteins. Systematic genetic analysis of the SREBP pathway using invertebrate model organisms can lead to the identification of new drug targets, therapeutic agents, diagnostics and prognostics useful in the treatment of disorders associated with lipid metabolism. Additionally, use of these invertebrate model organisms could lead to the identification and validation of pesticide targets directed to components of the SREBP pathway.

The details of the conditions used for the identification and/or isolation of each novel SREBP pathway nucleic acid and protein are described in the Examples section below. Various non-limiting embodiments of the invention and applications and uses of these novel *C. elegans and Drosophila melanogaster* SREBP pathway genes and proteins are discussed in the following sections. The entire contents of all references cited herein are incorporated by reference in their entireties for all purposes. Additionally, the citation of a reference in the preceding background section is not an admission of prior art against the claims appended hereto.

Nucleic Acids of the SREBP Pathway

The invention relates generally to nucleic acid sequences of the SREBP pathway, and more particularly SREBP pathway nucleic acid sequences of *C. elegans and Drosophila melanogaster*, and methods of using these sequences. As described in the Examples below, the present invention provides a nucleic acid sequence (SEQ ID NO:1) that was isolated from *C. elegans* and encodes an SREBP homologue referred to herein as "ceSREBP". The invention also provides nucleic acid sequences that were isolated from *Drosophila melanogaster* and encode homologues of S2P (dS2P; SEQ ID NO:3) and SCAP (dSCAP; SEQ ID NO:5). In addition to the fragments and derivatives of SEQ ID NOs 1, 3, and 5, as described in detail below, the invention includes the reverse complements thereof Also, the subject nucleic acid sequences, derivatives and fragments thereof may be RNA molecules comprising the nucleotide sequence of any one of SEQ ID NOs 1, 3, and 5 (or derivative or fragment thereof) wherein the base U (uracil) is substituted for the base T (thymine). The DNA and RNA sequences of the invention can be single- or double-stranded. Thus, the term "nucleic acid sequence", as used herein, includes the reverse complement, RNA equivalent, DNA or RNA double-stranded sequences, and DNA/RNA hybrids of the sequence being described, unless otherwise indicated explicitly or by context.

Fragments of these sequences can be used for a variety of purposes, for example, as nucleic acid hybridization probes and replication/amplification primers. Certain "antisense" fragments, i.e. that are reverse complements of the sequences set forth in any one of SEQ ID NOs: 1, 3, and 5, have utility in inhibiting the function of SREBP pathway proteins. The fragments are of length sufficient to specifically hybridize with the corresponding SEQ ID NO 1, 3, or 5. In particular, the invention provides fragments of at least 12, preferably at least 24, more preferably at least 36, and more preferably at least 96 contiguous nucleotides of any one of SEQ ID NOs: 1, 3, and 5. In some embodiments, fragments of at least 200 or 500 nucleotides may be preferred. When the fragments are flanked by other nucleic acid sequences, the total length of the combined nucleic acid sequence is less than 15 kb, and preferably less than 10 kb, more preferably less than 2 kb, and in some embodiments, more preferably less than 500 bases.

Preferred fragments of ceSREBP (SEQ ID NO:1) include those having at least 535 contiguous nucleotides of SEQ ID NO:1, and more preferably at least 540 nucleotides. In another embodiment of the invention, a fragment contains approximately residues 1090 to 1290 of SEQ ID NO:1, which encodes a bHLH-Zip domain. Other preferred fragments comprise any one of the following contiguous sequences of SEQ ID NO:1: nucleotides 1–85, 70–90, 76–218, 203–223, 208–528, 513–533, 517–637, 623–643, 626–1058, 1043–1063, 1048–1293, 1279–1299, 1277–1486, 1473–1493, 1477–2016, 2002–2022, 2004–2413, 2399–2419, 2404–2641, 2627–2647, 2632–2795, 2781–3001, 2786–3156, 3142–3162, and 3147–3397.

Preferred fragments of dS2P (SEQ ID NO:3) include those having at least 1226 contiguous nucleotides of SEQ ID NO:3, and more preferably at least 1231 nucleotides. Other preferred fragments comprise any one of the following contiguous sequences of SEQ ID NO:3: nucleotides 5–296, 281–301, 287–734, 719–739, and 725–1958.

Preferred fragments of dSCAP (SEQ ID NO:5) include those having at least 2274 contiguous nucleotides of SEQ ID NO:5, and more preferably at least 2279 nucleotides. Other preferred fragments comprise any one of the following contiguous sequences of SEQ ID NO:5: nucleotides 1–160, 150–170, 151–544, 529–549, 526–719, 704–724, 711–2988, 2974–3004, 2981–3191, 3177–3197, 3182–3546, 3532–3552 and 3537–3765.

Additionally, fragments of any of the foregoing sequences that are double-stranded RNA (dsRNA) molecules have utility in RNA interference (RNAi) studies, as described in more detail below, where model organisms exhibiting loss-of-function phenotype are generated. Typically, dsRNA molecules for RNAi studies are from about 200 to 2000 bp, and are preferably 600–900 bp in size.

The subject nucleic acid sequences may consist solely of any one of SEQ ID NOs:1, 3, and 5, or fragments thereof Alternatively, the subject nucleic acid sequences and fragments thereof may be joined to other components such as labels, peptides, agents that facilitate transport across cell membranes, hybridization-triggered cleavage agents or intercalating agents. The subject nucleic acid sequences and fragments thereof may also be joined to other nucleic acid sequences (i.e. they may comprise part of larger sequences) and are of synthetic/non-natural sequences and/or are isolated, i.e. unaccompanied by at least some of the material with which it is associated in its natural state. Preferably, the isolated nucleic acids constitute at least about 0.5%, and more preferably at least about 5% by weight of the total nucleic acid present in a given fraction, and are preferably recombinant, meaning that they comprise a non-natural sequence or a natural sequence joined to nucleotide(s) other than that which it is joined to on a natural chromosome.

The invention also provides derivative nucleic acid sequences which hybridize to the nucleic acid sequence of any one of SEQ ID NOs:1, 3, and 5 under stringency conditions such that each hybridizing derivative nucleic acid is related to the subject nucleic acid by a certain degree of sequence identity. In a specific embodiment, the derivative nucleic acid hybridizes to the reverse complement of SEQ ID NO:1, 3 or 5 and has the antigenicity of a polypeptide encoded by SEQ ID NO:2, 4, or 6, respectively. The temperature and salt concentrations at which hybridizations are performed have a direct effect on the results that are obtained. With "stringent" or "high stringency" conditions, a denaturing agent, such as formamide, is used during hybridization. The formamide is typically used at 25% to 50% (v/v) in a buffered diluent comprising 1x to 6xSSC (I1xSSC is 150 mM NaCl and 15 mM sodium citrate; SSPE may be substituted for SSC, 1xSSPE is 150 mM NaCl, 10 mM Na $H_2PO_4$, and 1.25 mM EDTA, pH7.4). The hybridization temperature is typically about 42° C. High stringency conditions also employ a wash buffer with low ionic strength, such as 0.1x to about 0.5xSSC, at relatively high temperature, typically greater than about 55° C. to about 70° C. Moderately stringent conditions typically use 0% to 25% formamide in 1x to 6xSSC, and use reduced hybridization temperatures, usually in the range of about 27° C. to about 40° C. The wash buffer can have increased ionic strength, e.g. about 0.6x to about 2xSSC, and is used at reduced temperatures, usually from about 45° C. to about 55° C. With "non-stringent" or "low stringency" hybridization conditions, the hybridization buffer is the same as that used for moderately stringent or high stringency, but does not contain a denaturing agent. A reduced hybridization temperature is used, typically in the range of about 25° C. to about 30° C. The wash buffer has increased ionic strength, usually around 2x to about 6xSSC, and the wash temperature is in the range of about 35° C. to about 47° C. Procedures for nucleic acid hybridizations are well-known in the art (Ausubel et al., Current Protocols in Molecular Biology (1995) Wiley Interscience Publishers; Sambrook et al., Molecular Cloning: A Laboratory Manual (1989) Cold Spring Harbor Press, New York; Shilo and Weinberg, Proc. Natl. Acad. Sci. U.S.A. (1981) 78:6789–6792).

In a specific embodiment of the invention, nucleic acids are provided that are capable of hybridizing to any one of SEQ ID NOs:1, 3, and 5, or the above-specified fragments thereof, under any one of the hybridization conditions listed in Table 1. Hybridization conditions 8–10, as listed in Table 1, are generally considered "high stringency" conditions; conditions 4–7 are generally considered "moderately stringent", and conditions 1–3 are considered "non-stringent".

TABLE I

| Condition # | Hybridization Buffer | Hybridization Temp. | Wash Buffer | Wash Temp. |
|---|---|---|---|---|
| 1 | 6x SSC/ 0% formamide | 25° C. | 4x SSC | 35° C. |
| 2 | 6x SSC/ 0% formamide | 25° C. | 4x SSC | 40° C. |
| 3 | 6x SSC/ 0% formamide | 27° C. | 4x SSC | 47° C. |
| 4 | 6x SSC/ 0% formamide | 34° C. | 2x SSC | 45° C. |
| 5 | 6x SSC/ 0% formamide | 40° C. | 0.8x SSC | 45° C. |
| 6 | 3x SSC/ 0% formamide | 40° C. | 0.6x SSC | 50° C. |
| 7 | 1x SSC/ 0% formamide | 40° C. | 0.6x SSC | 55° C. |
| 8 | 6x SSC/ 25% formamide | 42° C. | 0.5x SSC | 60° C. |
| 9 | 2x SSC/ 25% formamide | 42° C. | 0.4x SSC | 65° C. |
| 10 | 1x SSC/ 25% formamide | 42° C. | 0.3x SSC | 70° C. |

Condition #1 shown in Table 1 is designed to isolate nucleic acids having at least about 50% sequence identity with the target nucleic acid (with % identity calculated as described below). With each subsequent condition, the stringency is such that the isolated nucleic acid has a sequence identity of at least 5% greater than what would be isolated by using the next lower condition number. Thus, for example, condition #2 is designed to isolate nucleic acids having at least about 55% sequence identity with the target nucleic acid, and conditions #9 and #10 are designed to isolate nucleic acids having at least about 90% and 95% sequence identity, respectively, to the target nucleic acid. Preferably, each hybridizing derivative nucleic acid has a length that is at least 30% of the length of the subject nucleic acid sequence described herein to which it hybridizes. More preferably, the hybridizing nucleic acid has a length that is at least 50%, still more preferably at least 70%, and most preferably at least 90% of the length of the subject nucleic acid sequence to which it hybridizes.

As used herein, "percent (%) nucleic acid sequence identity" with respect to a subject sequence, or a specified portion of a subject sequence, is defined as the percentage of nucleotides in the candidate derivative nucleic acid sequence identical with the nucleotides in the subject sequence (or specified portion thereof), after aligning the sequences and introducing gaps, if necessary to achieve the maximum percent sequence identity, as generated by the program WU-BLAST-2.0a 19 (Altschul et al., J. Mol. Biol. parameters set to default values. The HSP S and HSP S2 parameters are dynamic values and are established by the program itself depending upon the composition of the particular sequence and composition of the particular database against which the sequence of interest is being searched. A % nucleic acid sequence identity value is determined by the number of matching identical nucleotides divided by the sequence length for which the percent identity is being reported. Preferably, derivative nucleic acid sequences of the present invention have at least 70% preferably at least 80%, more preferably at least 85%, still more preferably at least 90%, and most preferably at least 95% sequence identity with any one of SEQ ID NOs:1, 3, and 5. In some preferred embodiments, the derivative nucleic acid encodes a polypeptide comprising an amino acid sequence of any one of SEQ ID NOs:2, 4, and 6, or a functionally active fragment thereof.

A derivative of the subject nucleic acid sequence, or fragment thereof, may comprise 100% sequence identity with the subject nucleic acid sequence, but be a derivative thereof in the sense that it has one or more modifications at the base or sugar moiety, or phosphate backbone. Examples of modifications are well known in the art (Bailey J. E. Ullmann's Encyclopedia of Industrial Chemistry (1998), $6^{th}$ ed. Wiley and Sons). Such derivatives may be used to provide modified stability or any other desired property.

Another type of derivative of the subject nucleic acid sequences includes corresponding humanized sequences. A humanized nucleic acid sequence is one in which one or more codons has been substituted with a codon that is more commonly used in human genes. The following list shows, for each amino acid, the calculated codon frequency (number in parentheses) in humans genes for 1000 codons (Wada et al., Nucleic Acids Research (1990) 18(Suppl.): 2367–2411):

| Human codon frequency per 1000 codons: | | | | | |
|---|---|---|---|---|---|
| ARG: CGA (5.4), | CGC (11.3), | CGG (10.4), | CGU (4.7), | AGA (9.9), | AGG (11.1) |
| LEU: CUA (6.2), | CUC (19.9), | CUG (42.5), | CUU (10.7), | UUA (5.3), | UUG (11.0) |
| SER: UCA (9.3), | UCC (17.7), | UCG (4.2), | UCU (13.2), | AGC (18.7), | AGU (9.4) |
| THR: ACA (14.4), | ACC (23.0), | ACG (6.7), | ACU (12.7) | | |
| PRO: CCA (14.6), | CCC (20.0), | CCG (6.6), | CCU (15.5) | | |
| ALA: GCA (14.0), | GCC (29.1), | GCG (7.2), | GCU (19.6) | | |
| GLY: GGA (17.1), | GGC (25.4), | GGG (17.3), | GGU (11.2) | | |
| VAL: GUA (5.9), | GUC (16.3), | GUG (30.9), | GUU (10.4) | | |
| LYS: AAA (22.2), | AAG (34.9) | | | | |
| ASN: AAC (22.6), | AAU (16.6) | | | | |
| GLN: CAA (11.1), | CAG (33.6) | | | | |
| HIS: CAC (14.2), | CAU (9.3) | | | | |
| GLU: GAA (26.8), | GAG (41.4) | | | | |
| ASP: GAC (29.0), | GAU (21.7) | | | | |
| TYR: UAC (18.8), | UAU (12.5) | | | | |
| CYS: UGC (14.5), | UGU (9.9) | | | | |
| PHE: UUU (22.6), | UUC (15.8) | | | | |
| ILE: AUA (5.8), | AUC (24.3), | AUU (14.9) | | | |
| MET: AUG (22.3) | | | | | |
| TRP: UGG (13.8) | | | | | |
| TER: UAA (0.7), | AUG (0.5), | UGA (1.2) | | | |

Thus, an SREBP pathway nucleic acid sequence in which the glutamic acid codon, GAA has been replaced with the codon GAG, which is more commonly used in human genes, is an example of a humanized SREBP pathway nucleic acid sequence. A detailed discussion of the humanization of nucleic acid sequences is provided in U.S. Pat. No. 5,874,304 to Zolotukhin et al.

Isolation, Production, and Expression of Nucleic Acids of the SREBP Pathway

Nucleic acid encoding the amino acid sequence of any one of SEQ ID NOs:2, 4, and 6, may be obtained from an appropriate cDNA library prepared from any eukaryotic species that encodes SREBP pathway proteins such as vertebrates, preferably mammalian (e.g. primate, porcine, bovine, feline, equine, and canine species, etc.) and invertebrates, such as arthropods, particularly insects species (preferably *Drosophila melanogaster*) and arachnids, and nematodes (preferably *C. elegans*). An expression library can be constructed using known methods. For example, mRNA can be isolated to make cDNA which is ligated into a suitable expression vector for expression in a host cell into which it is introduced. Various screening assays can then be used to select for the gene or gene product (e.g. oligonucleotides of at least about 20 to 80 bases designed to identify the gene of interest, or labeled antibodies that specifically bind to the gene product).

Polymerase chain reaction (PCR) can also be used to isolate nucleic acids of the SREBP pathway where oligonucleotide primers representing fragmentary sequences of interest amplify RNA or DNA sequences from a source such as a genomic or cDNA library (as described by Sambrook et al., supra). Additionally, degenerate primers for amplifying homologues from any species of interest may be used. Once a PCR product of appropriate size and sequence is obtained, it may be cloned and sequenced by standard techniques, and utilized as a probe to isolate a complete cDNA or genomic clone.

Fragmentary sequences of SEQ ID NOs 1, 3 and 6 may be synthesized by known methods. For example, oligonucleotides may be synthesized using an automated DNA synthesizer available from commercial suppliers (e.g. Biosearch, Novato, Calif.; Perkin-Elmer applied Biosystems, Foster City, Calif.). Antisense RNA sequences can be produced intracellularly by transcription from an exogenous sequence, e.g. from vectors that contain antisense SREBP pathway nucleic acid sequences. Newly generated sequences may be identified and isolated using standard methods.

An isolated SREBP pathway nucleic acid sequence can be inserted into any appropriate cloning vector, for example bacteriophages such as lambda derivatives, or plasmids such as PBR322, pUC plasmid derivatives and the Bluescript vector (Stratagene, San Diego, Calif.). Recombinant molecules can be introduced into host cells via transformation, transfection, infection, electroporation, etc. The transformed cells can be cultured to generate large quantities of the SREBP pathway nucleic acid. Suitable methods for isolating and producing the subject nucleic acid sequences are well-known in the art (Sambrook et al., supra; Glover (ed.), DNA Cloning: A Practical Approach, Vol. 1, 2, 3, 4, (1995) MRL Press, Ltd., Oxford, U.K.).

The nucleotide sequence coding an SREBP pathway protein or a functionally active fragment or derivative thereof, can be inserted into any appropriate expression vector for the transcription and translation of the inserted protein-coding sequence. Alternatively, the necessary transcriptional and translational signals can be supplied by the native SREBP pathway gene and/or its flanking regions. A variety of host-vector systems may be utilized to express the protein-coding sequence such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, DNA, plasmid DNA, or cosmid DNA. Expression of an SREBP pathway protein may be controlled by a suitable promoter/enhancer element. In addition, a host cell strain may be selected which modulates the expression of the inserted sequences, or modifies and processes the gene product in the specific fashion desired.

In a specific embodiment, a vector is used that comprises a promoter operably linked to an SREBP pathway gene nucleic acid, one or more origins of replication, and optionally, one or more selectable markers (e.g. thymidine kinase activity, resistance to antibiotics, etc.) so that expression of the gene product can be detected. Alternatively, recombinant expression vectors can be identified by assaying for the expression of the SREBP pathway gene product based on the physical or functional properties of the SREBP pathway protein in in vitro assay systems (e.g. immunoassays).

In specific embodiments, the SREBP pathway protein, fragment, or derivative may be expressed as a fusion, or chimeric protein product (i.e. it is joined via a peptide bond to a heterologous protein sequence of a different protein). Such a chimeric product can be made by ligating the appropriate nucleic acid sequences encoding the desired amino acid sequences to each other in the proper coding frame (using methods known in the art) and expressing the chimeric product. Alternatively, such a chimeric product may be made by protein synthetic techniques, e.g. by use of a peptide synthesizer.

Once a recombinant which expresses the SREBP pathway gene sequence is identified, the gene product can be isolated using standard methods (e.g. ion exchange, affinity, and sizing column chromatography; centrifugation; differential solubility). The amino acid sequence of the protein can be deduced from the nucleotide sequence of the chimeric gene contained in the recombinant. As a result, the protein can be synthesized by standard chemical methods known in the art (Hunkapiller et al., Nature (1984) 310:105–111). Alternatively, native SREBP-pathway proteins can be purified from natural sources, by standard methods (e.g. immunoaffinity purification).

SREBP Pathway Proteins

The invention provides SREBP pathway proteins that comprise or consist of an amino acid sequence of any one of SEQ ID NOs: 2, 4, and 6, or fragments or derivatives thereof. Compositions comprising these proteins may consist essentially of the SREBP pathway proteins. Alternatively, the SREBP pathway proteins may be a component of a composition that comprises other components (e.g. a diluent such as saline, a pharmaceutically acceptable carrier or excipient, a culture medium, carriers used in pesticide formulations, etc.).

Typically, a derivative of an SREBP pathway protein will share a certain degree of sequence identity or sequence similarity with any one of SEQ ID NOs 2, 4, and 6, or a fragment thereof. As used herein, "percent (%) amino acid sequence identity" with respect to a subject sequence, or a specified portion of a subject sequence, is defined as the percentage of amino acids in the candidate derivative amino acid sequence identical with the amino acid in the subject sequence (or specified portion thereof), after aligning the sequences and introducing gaps, if necessary to achieve the maximum percent sequence identity, as generated by the program WU-BLAST-2.0al 9 (Altschul et al., supra) using the same parameters discussed above for derivative nucleic acid sequences. A % amino acid sequence identity value is determined by the number of matching identical amino acids divided by the sequence length for which the percent identity is being reported. Preferably, derivative amino acid sequences of the present invention have at least 80%, preferably at least 85%, more preferably at least 90%, and most preferably at least 95% sequence identity with any contiguous stretch of at least 20 amino acids, preferably at least 25 amino acids, and more preferably at least 30 amino acids of any one of SEQ ID NOs 2, 4, and 6. "Percent (%) amino acid sequence similarity" is determined by doing the same calculation as for determining % amino acid sequence identity described above, but including conservative amino acid substitutions in additional to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine and valine; interchangeable polar amino acids are glutamine and asparagine; interchangeable basic amino acids arginine, lysine and histidine; interchangeable acidic amino acids aspartic acid and glutamic acid; and interchangeable small amino acids alanine, serine, threonine, methionine, and glycine.

The preferred derivative of ceSREBP consists of or comprises an amino acid sequence that has at least 55%, preferably at least 66%, and more preferably, at least 65% sequence identity with amino acid residues 335–428 of SEQ ID NO:2 (i.e. the bHLH-Zip domain). Other preferred derivatives of ceSREBP consist of or comprise an amino acid sequence that shares at least 75% similarity, preferably at least 80% similarity, and more preferably, at least 85% similarity with amino acid residues 335–428 of SEQ ID NO:2. Preferably, such derivatives share antigenicity with amino acid residues 335–428 of SEQ ID NO:2.

The invention also provides proteins having amino acid sequences that consist of or comprise a fragment of any one of SEQ ID NOs 2, 4, and 6. The fragments usually have at least 10, preferably at least 12, and more preferably at least 15 contiguous amino acids of any one of SEQ ID NOs 2, 4, and 6. A preferred fragment of ceSREBP contains at least 8, preferably at least 10, and more preferably at least 12 contiguous amino acids of residues 335 to 428 of SEQ ID NO:2.

Preferably the fragment or derivative of the SREBP pathway protein is "functionally active" meaning that the SREBP pathway protein derivative or fragment exhibits one or more functional activities associated with a full-length, wild-type SREBP pathway protein comprising the amino acid sequence of any one of SEQ ID NOs:2, 4, and 6. As an example, functionally active SREBP pathway protein fragments or derivatives include polypeptides that have the antigenicity of the SREBP pathway protein such that they can be used in immunoassays, for immunization, for inhibition of SREBP pathway activity, etc. As another example, a fragment or derivative of SREBP may be considered functionally active if it binds a regulatory DNA element of an appropriate target gene such as the SRE-1 sequence. S2P may be considered functionally active if it cleaves SREBP at site 2 (as depicted in FIG. 1B), etc. A fragment or derivative of SCAP may be considered functionally active it is capable of binding to the C-terminal regulatory domain of SREBP. Fragments or derivatives of SREBP pathway proteins can be tested for functional activity by various procedures known in, the art. In a preferred method which is described in detail below, a model organism, such as an insect (e.g. *D. melanogaster*) or won (e.g. *C. elegans*), or other model system, is used in genetic studies to assess the phenotypic effect of a fragment or derivative (i.e. mutant). As used herein, functionally active fragments also include polypeptides that are lacking one or more structural or functional domains of an SREBP pathway protein. Examples of such domains include transmembrane domains, cytosolic domains, lumenal domains, regulatory domains, etc. Thus, for example, an SREBP polypeptide lacking the N-terminal acidic region and/or the C-terminal regulatory region, is considered a functionally-active fragment.

The SREBP pathway derivatives of the invention can be produced by various methods known in the art. The manipulations which result in their production can occur at the gene or protein level. For example, a cloned SREBP pathway gene sequence can be cleaved at appropriate sites with restriction endonuclease(s) (Wells et al., Philos. Trans. R. Soc. London SerA (1986) 317:415), followed by further enzymatic modification if desired, isolated, and ligated in vitro, and expressed to produce the desired derivative. Alternatively, an SREBP pathway gene can be mutated in vitro or in vivo, to create and/or destroy translation, initiation, and/or termination sequences, or to create variations in coding regions and/or to form new restriction endonuclease sites or destroy preexisting ones, to facilitate further in vitro modification. A variety of mutagenesis techniques are known in the art such as chemical mutagenesis, in vitro site-directed mutagenesis (Carter et al., Nucl. Acids Res. (1986) 13:4331), use of TAB® linkers (available from Pharmacia and Upjohn, Kalamazoo, Mich.), etc.

At the protein level, manipulations include post translational modification, e.g. glycosylation, acetylation, phosphorylation, a midation, derivatization by known protecting/blocking groups, proteolytic cleavage, linkage to an antibody molecule or other cellular ligand, etc. Any of numerous chemical modifications may be carried out by known technique (e.g. specific chemical cleavage by cyanogen bromide, trypsin, chyrnotrypsin, papain, V8 protease, $NaBH_4$, acetylation, formylation, oxidation, reduction, metabolic synthesis in the presence of tunicamycin, etc.). Derivative proteins can also be chemically synthesized by use of a peptide synthesizer, for example to introduce nonclassical amino acids or chemical amino acid analogs as substitutions or additions into the SREBP pathway protein sequence.

Chimeric or fusion proteins can be made comprising an SREBP pathway protein or fragment thereof (preferably consisting of at least a domain or motif of the SREBP pathway protein, or at least 6, and preferably at least 10 amino acids of the SREBP pathway protein) joined at its amino- or carboxy-terminus via a peptide bond to an amino acid sequence of a different protein. Such a chimeric protein can be produced by any known method, including: recombinant expression of a nucleic acid encoding the protein (comprising an SREBP pathway-coding sequence joined in-frame to a coding sequence for a different protein); ligating the appropriate nucleic acid sequences encoding the desired amino acid sequences to each other in the proper coding frame, and expressing the chimeric product; and protein synthetic techniques, e.g. by use of a peptide synthesizer.

Antibodies to SREBP Pathway Proteins

SREBP pathway proteins, including functional derivatives and fragments thereof (e.g. an SREBP pathway protein encoded by a sequence of any one of SEQ ID NOs:2, 4, and 6, or a subsequence thereof) may be used as an immunogen to generate monoclonal or polyclonal antibodies and antibody fragments or derivatives (e.g. chimeric, single chain, Fab fragments). For example, antibodies to a particular domain of an SREBP pathway protein may be desired (e.g. an SRE binding domain). In a specific embodiment, fragments of an SRFBP pathway protein identified as hydrophilic are used as immunogens for antibody production using art-known methods. Various known methods for antibody production can be used including cell culture of hybridomas; production of monoclonal antibodies in germ-free animals (PCT/US90/02545); the use of human hybridomas (Cole et al., Proc. Natl. Acad. Sci. U.S.A. (1983) 80:2026–2030; Cole et al., in Monoclonal Antibodies and Cancer Therapy (1985) Alan R. Liss, pp. 77–96), and production of humanized antibodies (Jones et al., Nature (1986) 321:522–525; U.S. Pat. No. 5,530,101).

Molecules Which Interact With SREBP Pathway Proteins

The present invention provides methods of identifying or screening for molecules, such as proteins or other compounds, which interact with SREBP pathway proteins, or derivatives, or fragments thereof. Assays to find interacting proteins can be performed by any method known in the art, for example, immunoprecipitation with an antibody that binds to the protein in a complex followed by analysis by size fractionation of the immunoprecipitated proteins (e.g. by denaturing or nondenaturing polyacrylamide gel electrophoresis), Western analysis, non-denaturing gel electrophoresis, etc. A preferred method for identifying interacting proteins is a two hybrid assay system or variation thereof (Fields and Song, Nature (1989) 340:245–246; U.S. Pat. No. 5,283,173; for review see Brent and Finley, Annu. Rev. Genet. (1997) 31:663–704).

The most commonly used two-hybrid screen system is performed using yeast. All systems share three elements: 1) a gene that directs the synthesis of a "bait" protein fused to a DNA binding domain; 2) one or more "reporter" genes having an upstream binding site for the bait, and 3) a gene that directs the synthesis of a "prey" protein fused to an activation domain that activates transcription of the reporter gene. For the screening of proteins that interact with SREBP pathway proteins, the "bait" is preferably an SREBP pathway protein having an amino acid sequence of any one of SEQ ID NOs:2, 4, and 6 (or derivative or fragment thereof), expressed as a fusion protein to a DNA binding domain. Because most two-hybrid systems are engineered to enter the nucleus and activate transcription, transmembrane portions of proteins can interfere with proper association, folding, and nuclear transport of bait or prey segments (Ausubel et al., supra; Allen et al., Trends Biochem. Sci. (1995) 20:511–516). Therefore, the "bait" is preferably an SREBP pathway protein derivative or a fragment that lacks transmembrane domains. The "prey" protein is a protein to be tested for ability to interact with the bait, and is expressed as a fusion protein to a transcription activation domain. In one embodiment, the prey proteins can be obtained from recombinant biological libraries expressing random peptides.

The bait fusion protein can be constructed using any suitable DNA binding domain. In a preferred system, the bait contains DNA binding and dimerization domains of the E. coli LexA repressor protein. LexA binds tightly to several different operators, and carries a dimerization domain at its C. terminus. In another preferred system, the bait contains residues 1–147 of the yeast GAL4 protein which binds tightly to appropriate DNA binding sites, localizes fused proteins to the nucleus, and directs dimerization (Bartel et al., BioTechniques (1993) 14:920–924, Chasman et al., Mol. Cell. Biol. (1989) 9:4746–4749; Ma et al., Cell (1987) 48:847–853; Ptashne et al., Nature (1990) 346:329–331).

The prey fusion protein can be constructed using any suitable activation domain such as GAL4, VP-16, etc. In various embodiments the preys contain useful moieties such as nuclear localization signals (Ylikomi et al., EMBO J. (1992) 11:3681–3694; Dingwall and Laskey, TIBS (1991)

16:479–481) or epitope tags (Allen et al., supra) to facilitate isolation of the encoded proteins. Activation tagged proteins also differ in whether they are expressed constitutively, or conditionally. In a preferred embodiment, the prey is conditionally expressed, allowing the transcription phenotypes obtained in selections (or "hunts") for interactors to be ascribed to the synthesis of the tagged protein, thus reducing the number of false positive cells that grow because their reporters are aberrantly transcribed.

Any reporter gene can be used that has a detectable phenotype. In various specific embodiments, some reporter genes allow cells expressing them to be selected by growth on appropriate medium (e.g. HIS3, LEU2 described by Chien et al., Proc. Nati. Acad. Sci. U.S.A. (1991) 88:9572–9582; and Gyuris et al., Cell (1993) 75:791–803). Others allow cells expressing them to be visually screened such as LacZ and GFP (Chien et al., supra; and http:/www.bio101.com). Reporters also differ in the number and affinity of upstream binding sites (e.g. 1exA operators) for the bait, and in the position of these sites relative to the transcription start point. Finally, reporter genes differ in the number of molecules of the reporter gene product necessary to score the phenotype. These differences affect the strength of the protein interactions the reporters can detect. Thus, for example, one or more tandem copies (e.g. four or five copies) of the appropriate DNA binding site can be introduced upstream of the TATA box in the desired promoter (e.g. in the area of about position −100 to about −400). In a preferred aspect, 4 or 5 tandem copies of the 17 bp UAS (GAL4 DNA binding site) are introduced upstream of the TATA box in the desired promoter, which is upstream of the desired coding sequence for a selectable or detectable marker.

Although the preferred host for two-hybrid screening is the yeast, the host cell in which the interaction assay and transcription of the reporter gene occurs can be any cell, such as mammalian (e.g. monkey, mouse, rat, human, bovine), chicken, bacterial, or insect cells. Expression constructs encoding and capable of expressing the binding domain fusion proteins, the transcriptional activation domain fusion proteins, and the reporter gene product(s) are provided within the host cell, by mating of cells containing the expression constructs, or by cell fusion, transformation, electroporation, microinjection, etc. The host cell used should not express an endogenous transcription factor that binds to the same DNA site as that recognized by the DNA binding domain fusion population. Also, preferably, the host cell is mutant or otherwise lacking in an endogenous, functional form of the reporter gene(s) used in the assay. Various vectors and host strains for expression of the two fusion protein populations in yeast can be used (U.S. Pat. No. 5,1468,614; Bartel et al., Cellular Interactions in Development (1993) Hartley, ed., Practical Approach Series xviii, IRL Press at Oxford University Press, New York, N.Y., pp. 153–179; and Fields and Stemglanz, Trends In Genetics (1994) 10:286–292. As an example of a mammalian system, interaction of activation tagged VP16 derivatives with a GALA-derived bait drives expression of reporters that direct the synthesis of Hygromycin B phosphotransferase, Chloramphenicol acetyltransferase, or CD4 cell surface antigen (Fearon et al., Proc. Natl. Acad. Sci. U.S.A. (1992) 89:7958–7962). In another embodiment, interaction of VPI6-tagged derivatives with GAL4-derived baits drives the synthesis of SV40 T antigen, which in turn promotes the replication of the prey plasmid, which carries an SV40 origin (Vasavada et al., Proc. Natl. Acad. Sci. U.S.A. (1991) 88:10686–10690).

False positives arising from transcriptional activation by the DNA binding domain fusion proteins in the absence of a transcriptional activator domain fusion protein can be prevented or reduced by negative selection for such activation within a host cell containing the DNA binding fusion population, prior to exposure to the activation domain fusion population. For example, if such cell contains URA3 as a reporter gene, negative selection is canned out by incubating the cell in the presence of 5-fluoroorotic acid (5-FOA), which kills self-activating DNA-binding domain hybrids.

In a preferred embodiment, the bait SREBP pathway gene and the prey library of chimeric genes are combined by mating the two yeast strains on solid media for a period of approximately 6–8 hours. Alternatively, the mating can be performed in liquid media. The resulting diploids contain both kinds of chimeric genes, i.e., the DNA-binding domain fusion and the activation domain fusion.

Transcription of the reporter gene can be detected by a linked replication assay, for example, as described by Vasavada et al., supra, or using immunoassay methods, preferably as described in Alam and Cook (Anal. Biochem. (1990)188:245–254). The activation of other reporter genes like URA3, HIS3, LYS2, or LEU2 enables the cells to grow in the absence of uracil, histidine, lysine, or leucine, respectively, and hence serves as a selectable marker. Other types of reporters are monitored by measuring a detectable signal. For example, GFP and lacZ have gene products that are fluorescent and chromogenic, respectively.

After interacting proteins have been identified, the DNA sequences encoding the proteins can be isolated. In one method, the activation domain sequences or DNA-binding domain sequences (depending on the prey hybrid used) are amplified, for example, by PCR using pairs of oligonucleotide primers specific for the coding region of the DNA binding domain or activation domain. Other known amplification methods can be used, such as ligase chain reaction, use of Q replicase, or methods described by Kricka et al. (Molecular Probing, Blotting, and Sequencing (1995) Academic Press, New York, Chapter 1 and Table IX).

If a shuttle (yeast to *E. coli*) vector is used to express the fusion proteins, the DNA sequences encoding the proteins can be isolated by transforming the yeast DNA into *E. coli* and recovering the plasmids from *E. coli*. Alternatively, the yeast vector can be isolated, and the insert encoding the fusion protein subcloned into a bacterial expression vector, for growth of the plasmid in *E. coli*.

The two hybrid system can be used for screening candidate molecules that modulate interaction between the SREBP pathway protein and the protein with which it interacts. Briefly, the protein-protein interaction assay can be carried out by assaying for reporter gene activity as described above, except that it is done in the presence of one or more candidate molecules. An increase or decrease in reporter gene activity relative to that present when the one or more candidate molecules are absent indicates that the candidate molecule has an effect on the interacting pair. In a preferred method, inhibition of an interaction is selected when the inhibition is necessary for cell survival (e.g. an interaction that activates the URA3 gene, causing yeast to die in medium containing the chemical 5-fluoroorotic acid (Rothstein, Meth. Enzymol. (1983)101:167–180)). The identification of inhibitors of such interactions can also be accomplished using competitive inhibitor assays.

In Vivo and in Vitro Models of SREBP Pathway Gene Function and Dysfunction

Both genetically modified animal models (i.e. in vivo models), such as *C. elegans* and *Drosophila melanogaster*, and in vitro models such as genetically engineered cell lines expressing or mis-expressing SREBP pathway genes, are useful for studying lipid metabolism and disorders associated with abnormal lipid metabolism. Such models that display detectable phenotypes, such as those described in more detail below and in the examples, can be used for the identification and characterization of SREBP pathway genes or other genes of interest and/or phenotypes associated with the mutation or mis-expression of an SREBP pathway protein. The term "mis-expression" as used herein encompasses mis-expression due to gene mutations. Thus, a mis-expressed SREBP pathway protein may be one having an amino acid sequence that differs from wild-type (i.e. it is a derivative of the normal protein). A mis-expressed SREBP pathway protein may also be one in which one or more amino acids have been deleted, and thus is a "fragment" of the normal protein. As used herein, "mis-expression" also includes over-expression (e.g. by multiple gene copies), underexpression, and non-expression (e.g. by gene knockout or blocking expression that would otherwise normally occur). As used in the following discussion concerning in vivo and in vitro models, the term "gene of interest" refers to an SREBP pathway gene (i.e. SREBP, SCAP, S1P, and S2P), or any gene involved in regulation or modulation of the SREBP pathway. Such genes may include any gene involved in the biosynthesis or metabolism of cholesterol or fatty acids such as HMG coenzyme A synthase, HMG-CoA reductase, farnesyl diphosphate synthase, squalene synthase, fatty acid synthase, acetyl-CoA carboxylase, glycerol-3-phosphate acyltransferase, acyl-CoA binding protein, stearoyl CoA desaturase-1, lipoprotein lipase, and the LDL receptor.

The in vivo and in vitro models may be genetically engineered or modified so that they 1) have deletions and/or insertions of one or more SREBP pathway genes, 2) harbor interfering RNA sequences derived from SREBP pathway genes, 3) have had one or more endogenous SREBP pathway genes mutated, and/or 4) contain transgenes for mis-expression of wild-type or mutant forms of such genes. Such genetically modified in vivo and in vitro models are useful for identification of new genes that are involved in the synthesis, activation, control, etc. of SREBP pathway genes and/or gene products. Further, other genes of interest that are involved in cholesterol and/or fatty acid biosynthesis or metabolism may be identified. The newly identified genes could constitute possible pesticide targets (as judged by animal model phenotypes such as non-viability, block of normal development, defective feeding, defective movement, or defective reproduction). Alternatively, or additionally, they may constitute possible therapeutic targets, particularly in the area of metabolic diseases and disorders, for example, cholesterol synthesis, metabolism, and other fatty acid disorders. The model systems can also be used for testing potential pesticidal or pharmaceutical compounds that interact with the SREBP pathway, for example by administering the compound to the model system using any suitable method (e.g. direct contact, ingestion, injection, etc.) and observing any changes in phenotype, for example, changes in lipid content, lethality, etc.

A variety of known expression modification methods can be used to genetically modify the animal models and cell cultures so that they express or mis-express SREBP pathway proteins. Some specific examples include radiation mutagenesis such as X-rays, gamma rays, and ultraviolet radiation; chemical mutagenesis using, for example, ethylmethane sulfonate (EMS), methylmethane sulfonate (MMS), N-ethyl-N-nitrosourea (ENU), triethylmelamine, diepoxyalkanes, ICR-170, or formaldehyde; double-stranded RNA interference; use of peptide and RNA aptamers; transposon mutagenesis and transgene-mediated mis-expression. For some applications, it is useful to use genetic modification techniques that result in inheritable expression or mis-expression patterns such that the progeny of the genetically-modified animals can be studied. Various genetic modification techniques are discussed in more detail below and in the Examples.

Chemical Mutagenesis

A commonly-used chemical mutagen for creating loss-of-function mutations is ethyl methanesulfonate (EMS). In *C. elegans*, EMS mutagenesis can result in small deletions at a rate of approximately 13%. Accordingly, there is about a 95% probability of identifying a deletion in a gene of interest by screening $4 \times 10^6$ EMS-mutagenized genomes. Briefly, several million nematodes are mutagenized with EMS using the procedure described by Sulston and Hodgkin (The nematode *Caenorhabditis elegans* (1 988) Wood, Ed., Cold Spring Harbor Laboratory Press, Cold Spring Harbor, N.Y., pp. 587–606). The mutagenized nematodes are then distributed in small pools in 96-well plates, each pool composed of approximately 400 haploid genomes. A portion of each pool is used to generate a corresponding library of genomic DNA derived from the mutagenized nematodes. The DNA library is screened with a PCR assay to identify pools that carry genomes with deletions of interest. Mutant worms carrying the desired deletions are recovered from the corresponding pools of the mutagenized animals. Although EMS is a preferred mutagen to generate deletions, other mutagens can be used that also provide a significant yield of deletions, such as X-rays, gamma-rays, diepoxybutane, formaldehyde and trimethylpsoralen with ultraviolet light.

Chemical mutagenesis methods, and other methods, for generating loss-of-function mutations in *D. melatiogaster* are described by Ashburner (Drosophila: A Laboratory Manual (1989) Cold Spring Harbor, N.Y., Cold Spring Harbor Laboratory Press).

RNA-mediated Interference With Gene Expression

RNA-mediated interference (RNAi), is an effective method for generating loss-of-function phenotypes. Loss-of-function phenotypes can be generated by injecting anti-sense RNA that is partially homologous to a gene of interest into embryos using methods described by Schubiger and Edgar (Methods in Cell Biology (1994) 44:697–713). Another antisense RNA methodology involves expression of an antisense RNA partially homologous to the gene of interest by operably joining a portion of the gene in the antisense orientation to a powerful promoter (such as heat shock gene promoters, or promoters controlled by potent exogenous transcription factors, such as GAL4 and tTA) that can drive the expression of large quantities of the antisense RNA. Antiscnse RNA-generated loss-of-function phenotypes have been reported for several Drosophila genes (LaBonne et al., Dev. Biol. (1989) 136(1):16; Schuh and Jackie, Genome (1989) 31(1):422–5; and Geisler et al. Cell (1992) 71(4):613–21).

Loss-of-function phenotypes can also be generated by cosuppression methods where a sense strand RNA corresponding to a partial segment of the gene of interest is injected into the animal (Bingharn, Cell (1997) 90(3):385–7; Smyth, Curr. Biol. (1997) 7(12):793-Que and Jorgensen, Dev. Genet. (1998) 22(1):100–9; and Pal-Bhadra et at., Cell (1997) 90(3):479–90).

A preferred method for generating loss-of-function phenotypes is by double-stranded RNA interference (dsRNAi), which has been shown to be very effective in both *C. elegans* (Fire et al., Nature (1998) 391:806–811) and Drosophila (Kennerdall and Carthew, Cell (1998) 95:1017–1026). Briefly, complementary sense and antisense RNAs derived from a substantial portion Of the gene of interest are synthesized in vitro. Phagemid DNA templates containing cDNA clones of the gene are inserted between opposing promoters for T3 and T7 phage RNA polymerases. Alternatively, PCR products can be amplified from coding regions of the gene of interest, where the primers used for the PCR reactions are modified by the addition of phage T3 and T7 promoters. The resulting sense and antisense RNAs arc annealed in an injection buffer. In another embodiment, the interfering double-stranded RNA can be generated in vivo by co-expression of the complimentary sense and antisense RNAs derived from the gene of interest in the same cells. Interfering double-stranded RNA is administered to the animalsusually by injection or by soaking the animals in a solution containing the double-stranded RNA. The animals and their progeny are then inspected for phenotypes of interest.

Peptide and RNA Aplamers

Another method for generating loss-of-function phenotypes is the use of peptide aptamers, which are peptides or small polypeptides that act as dominant inhibitors of protein function. Peptide aptamers specifically bind to target proteins, blocking their function (Kolonin and Finley, Proc. Natl. Acad. Sci. (1998) 95:14266–71). Due to the highly selective nature of peptide aptamers, they may be used not only to target a specific protein, but also to target specific functions of a given protein (e.g. a DNA binding function). Further, peptide aptamers may be expressed in a controlled fashion by use of promoters which regulate expression in a temporal, spatial or inducible manner. Peptide aptamers act dominantly; therefore, they can be used to analyze proteins for which loss-of-function mutants are not available.

Peptide aptamers that bind with high affinity and specificity to a target protein may be isolated by a variety of techniques known in the art. In one method, they are isolated from random peptide libraries by yeast two-hybrid screens (Xu et al., Proc. Natl. Acad. Sci. (1997) 94:12473–78). They can also be isolated from phage libraries (Hoogenboom et al., Immunotechnology (1998) 4:1–20).

RNA aptamers are specific RNA ligands for proteins, that can specifically inhibit protein function of the gene (Good et al., Gene Therapy (1997) 4:45–54; Ellington. et al., Biotechnol. Annu. Rev. (1995) 1:185–214). In vitro selection methods can be used to identify RNA aptamers having a selected specificity (Bell et al., J. Biol. Chem. (1998) 273:14309–14). RNA aptamers can be used to decrease the expression of an SREBP pathway protein or derivative thereof, or a protein that interacts with any one of SREBP, S1P, S2P, and SCAP.

Transgenesis

Methods are well known for incorporating exogenous nucleic acid sequences into the genome of animals or cultured cells to create transgenic animals or recombinant cell lines. For invertebrate animal models, the most common methods involve the use of transposable elements. There are several suitable transposable elements that can be used to incorporate nucleic acid sequences into the genome of model organisms. Transposable elements are particularly useful for inserting sequences into a gene of interest so that the encoded protein is not properly expressed, creating a "knock-out" animal having a loss-of-function phenotype. Techniques are well-established for the use of P element in Drosophila (Rubin and Spradling, Science (1982) 218:348–53; U.S. Pat. No. 4,670,388) and Tel in *C. elegans* (Zwaal et al., Proc. Natl. Acad. Sci. U.S.A. (1993) 90:7431–7435; and *Caenorhabditis elegans*: Modern Biological Analysis of an Organism (1995) Epstein and Shakes, Eds.). Other Tc1-like transposable elements can be used such as "minos" (U.S. Pat. No. 5,348,874), "mariner" (Robertson, Insect Physiol. (1995) 41:99–105), and "sleeping beauty"(Ivics et al., Cell (1997) 91(4):501–510). Additionally, several transposable elements, that appear to function in a variety of diverse species, have been identified, including "piggyBac" (Thibault et al., Insect Mol Biol (1999) 8(1): 119–23), "hobo" (Atkinson et al., Proc. Natl. Acad. Sci. U.S.A. (1993) 90:9693–9697), and "hermes" (Sarkar et al., Insect Biochem & Molec. Biol. (1997) 27:359–363).

P elements, or marked P elements, are preferred for the isolation of loss-of-function mutations in Drosophila SREBP pathway genes because of the precise molecular mapping of these genes, depending on the availability and proximity of preexisting P element insertions for use as a localized transposon source (Hamilton and Zinn, Methods in Cell Biology (1994) 44:81–94; and Wolfner and Goldberg, Methods in Cell Biology (1994) 44:33–80). Typically, modified P elements are used which contain one or more elements that allow detection of animals containing the P element. Most often, marker genes are used that affect the eye color of Drosophila, such as derivatives of the Drosophila white or rosy genes (Rubin and Spradling, Science (1982) 218(4570):348–353; and Klemenz et al., Nucleic Acids Res. (1987) 15(10):3947–3959). However, in principle, any gene can be used as a marker that causes a reliable and easily scored phenotypic change in transgenic animals. Various other markers include bacterial plasmid sequences having selectable markers such as ampicillin resistance (Steller and Pirrotta, EMBO. J. (1985) 4:167–171); and lacZ sequences fused to a weak general promoter to detect the presence of enhancers with a developmental expression pattern of interest (Bellen et al., Genes Dev. (1989) 3(9):1288–1300). Other examples of marked P elements useful for mutagenesis have been reported (Nucleic Acids Research (1998) 26:85–88; and http://flybase.bio.indiana.edu).

A preferred method of transposon mutagenesis in Drosophila employs the "local hopping" method described by Tower et al. (Genetics (1993) 133:347–359). Each new P insertion line can be tested molecularly for transposition of the P element into the SREBP pathway gene of interest by assays based on PCR. For each reaction, one PCR primer is used that is homologous to sequences contained within the P element and a second primer is homologous to the coding region or flanking regions of the SREBP pathway gene. Products of the PCR reactions are detected by agarose gel clectrophoresis. The sizes of the resulting DNA fragments reveal the site of P element insertion relative to the SREBP pathway gene. Alternatively, Southern blotting and restriction mapping using DNA probes derived from genomic DNA or cDNAs of the SREBP pathway gene can be used to detect transposition events that rearrange the genomic DNA of the gene. P transposition events that map to the SREBP pathway gene can be assessed for phenotypic effects in heterozygous or homozygous mutant Drosophila.

In another embodiment, Drosophila lines carrying P insertions in an SREBP pathway gene, can be used to generate localized deletions using known methods (Kaiser, Bioassays (1990) 12(6):297–301; Harnessing the power of *Drosophila genetics*, In Drosophila melanogaster: Practical Uses in Cell and Molecular Biology, Goldstein and Fyrberg, Eds., Academic Press, Inc. San Diego, Calif.). This is particularly useful if no P element transpositions are found that disrupt a particular SREBP pathway gene of interest. Briefly, flies containing P elements inserted near an SREBP pathway gene are exposed to a further round of transposase to induce excision of the element. Progeny in which the transposon has excised are typically identified by loss of the eye color marker associated with the transposable element. The resulting progeny will include flies with either precise or imprecise excision of the P element, where the imprecise excision events often result in deletion of genomic DNA neighboring the site of P insertion. Such progeny are screened by molecular techniques to identify deletion events that remove genomic sequence from the gene of interest, and assessed for phenotypic effects in heterozygous and homozygous mutant Drosophila.

In C. elegans, Tc1 transposable element can be used for directed mutagenesis of a gene of interest. Typically, a Tc1 library is prepared by the methods of Zwaal et al., supra and Plasterk, supra, using a strain in which the Tc1 transposable element is highly mobile and present in a high copy number. The library is screened for Tc1 insertions in the region of interest using PCR with one set of primers specific for Tc1 sequence and one set of gene-specific primers. As described in detail in Example 4 below, using such procedures, C. elegans strains have been isolated that contain Tc1 transposon insertions within the SREBP gene. The screen for Tc1 deletions is performed and deletion animals are recovered.

In addition to creating loss-of-function phenotypes, transposable elements can be used to incorporate an SREBP pathway gene, or mutant or derivative thereof, as an additional gene into any region of an animal's genome resulting in mis-expression (including over-expression) of the gene. Alternatively, homologous recombination or gene targeting techniques can be used to substitute the gene for one or both copies of the animal's homologous gene. The transgene can be under the regulation of either an exogenous or an endogenous promoter element, and be inserted as either a minigene or a large genomic fragment. In one application, gene function can be analyzed by ectopic expression, using, for example, Drosophila (Brand et al., Methods in Cell Biology (1994) 44:635–654) or C. elegans (Mello and Fire, Methods in Cell Biology (1995) 48:451–482).

Typically, transgenic animals are created that contain gene fusions of the coding regions of the SREBP pathway gene (from either genomic DNA or cDNA) operably joined to a specific promoter and transcriptional enhancer whose regulation has been well characterized, preferably heterologous promoters/enhancers (i.e. promoters/enhancers that are non-native to the SREBP pathway genes being expressed). Heat shock promoters/enhancers, useful for temperature induced mis-expression in Drosophila include the hsp70 and hsp83 genes, and in C. elegans, include hsp 16-2 and hsp 16-41. Tissue specific promoters/enhancers are also useful, and in Drosophila, include sevenless (Bowtell et al., Genes Dev. (1988) 2(6):620–34), eyeless (Bowtell et a., Proc. Natl. Acad. Sci. U.S.A. (1991) 88(15):6853–7), and glass-responsive promoters/enhancers (Quiring et al., Science (1994) 265:785–9) which are useful for expression in the eye; and enhancers/promoters derived from the dpp or vestigal genes which are useful for expression in the wing (Staehling-Hampton et al., Cell Growth Differ. (1994) 5(6): 585–93; Kim et al., Nature (1996) 382:133–138). Finally, where it is necessary to restrict the activity of dominant active or dominant negative transgenes to regions where the pathway is normally active, it may be useful to use endogenous promoters of genes in the pathway, such as the SREBP pathway genes.

In C. elegans, examples of useful tissue specific promoters/enhancers include the myo-2 gene promoter, useful for pharyngeal muscle-specific expression; the h1h-1 gene promoter, useful for body- muscle-specific expression; and the mec-3 gene promoter, useful for touch-neuron-specific gene expression. In a preferred embodiment, gene fusions for directing the mis-expression of SREBP pathway genes are incorporated into a transformation vector which is injected into nematodes along with a plasmid containing a dominant selectable marker, such as rol-6. Transgenic animals are identified as those exhibiting a roller phenotype, and the transgenic animals are inspected for additional phenotypes of interest created by mis-expression of the SREBP pathway gene.

In Drosophila, binary control systems that employ exogenous DNA regulatory elements and exogenous transcriptional activator proteins, are particularly useful for testing the mis-expression of genes in a wide variety of developmental stage-specific and tissue-specific patterns. Two examples of binary exogenous regulatory systems include the UAS/GAL4 system from yeast (Hay et al., Proc. Natl. Acad. Sci. U.S.A. (1997) 94(10):5195–200; Ellis et al., Development (1993) 119(3):855–65), and the "Tet system" derived from E. coli (Bello et al., Development (1998) 125:2193–2202). The UAS/GAL4 system is a well-established and powerful method of mis-expression in Drosophila which employs the $UAS_G$ upstream regulatory sequence for control of promoters by the yeast GAL4 transcriptional activator protein (Brand and Perrimon, Development (1993) 118(2):401–15). In this approach, transgenic Drosophila, termed "target" lines, are generated where the gene of interest to be mis-expressed is operably fused to an appropriate promoter controlled by $UAS_G$. Other transgenic Drosophila strains, termed "driver" lines, are generated where the GAL4 coding region is operably fused to promoters/enhancers that direct the expression of the GAL4 activator protein in specific tissues, such as the eye, wing, nervous system, gut, or musculature. The gene of interest is not expressed in the target lines for lack of a transcriptional activator to drive transcription from the promoter joined to the gene of interest. However, when the UAS-target line is crossed with a GAL4 driver line, mis-expression of the gene of interest is induced in resulting progeny in a specific pattern that is characteristic for that GAL4 line. The technical simplicity of this approach makes it possible to sample the effects of directed mis-expression of the gene of interest in a wide variety of tissues by generating one transgenic target line with the gene of interest, and crossing that target line with a panel of pre-existing driver lines.

In the "Tet" binary control system, transgenic Drosophila driver lines are generated where the coding region for a tetracycline-controlled transcriptional activator (tTA) is operably fused to promoters/enhancers that direct the expression of tTA in a tissue-specific and/or developmental stage-specific manner. The driver lines are crossed with transgenic Drosophila target lines where the coding region for the gene of interest to be mis-expressed is operably fused to a promoter that possesses a tTA-responsive regulatory element. When the resulting progeny are supplied with food supplemented with a sufficient amount of tetracycline, expression of the gene of interest is blocked. Expression of the gene of interest can be induced at will simply by removal of tetracycline from the food. Also, the level of expression of the gene of interest can be adjusted by varying the level of tetracycline in the food. Thus, the use of the Tet system as a binary control mechanism for mis-expression has the advantage of providing a means to control the amplitude and timing of mis-expression of the gene of interest, in addition to spatial control. Consequently, if a gene of interest (e.g. a tumor suppressor gene) has lethal or deleterious effects when mis-expressed at an early stage in development, such as the embryonic or larval stages, the function of the gene of interest in the adult can still be assessed by adding tetracycline to the food during early stages of development and removing tetracycline later so as to induce mis-expression only at the adult stage.

Dominant negative mutations, where a mutation to a gene creates an inactive protein, can result in loss-of-function or reduced-function phenotype even in the presence of a normal copy of the gene, can be made using known methods (Hershkowitz, Nature (1987) 329:219–222). In the case of active monomeric proteins, over expression of an inactive form, achieved for example, by linking the mutant gene to a highly active promoter, can cause competition for natural substrates or ligands sufficient to significantly reduce net activity of the normal protein. Alternatively, changes to active site residues can be made to create a virtually irreversible association with a target.

In the case of active multimeric proteins, several strategies can guide selection of a dominant negative mutant. In one embodiment, activity of a multmeric complex can be decreased by expression of genes coding exogenous protein fragments that bind to the association domains of the wild type proteins and prevent multimer formation. Alternatively, over-expression of an inactive protein unit can sequester wild-type active units in inactive multimers, and thereby decrease multimeric activity (Nocka et al., EMBO J. (1996) 9:1805–1813). For example, in the case of multimeric DNA biriding proteins, the DNA binding domain can be deleted, or the activation domain deleted. Also, in this case, the DNA binding domain unit can be expressed without the activation domain causing sequestering of the target DNA. Thereby, DNA binding sites are tied up without any possible activation of expression. In the case where a particular type of unit normally undergoes a confirmation change during activity, expression of a rigid unit can also inactivate resultant complexes. It is also possible to replace an activation domain with a transcriptional repression domain and thus change a transcriptional activator into a transcriptional repressor. Transcriptional repression domains from the engrailed and Kruppel proteins have been used for such a purpose (Jaynes and O' Ferrell, EMBO J. (1991) 10:1427–1433; Licht. et al., Proc. Natl. Acad. Sci. USA (1993) 90:11361–65).

Expression Analysis of SREBP Pathway Genes

Various expression analysis techniques may be used to identify genes which are differentially expressed between a cell line or an animal expressing a wild type SREBP pathway gene compared to another cell line or animal expressing a mutant SREBP pathway gene. Such expression profiling techniques include differential display, serial analysis of gene expression (SAGE), nucleic acid array technology, subtractive hybridization, and proteome analysis (e.g. mass-spectrometry and two-dimensional protein gels). Nucleic acid array technology may be used to determine a global (i.e., genome-wide) gene expression pattern in a normal animal for comparison with an animal having a mutation in one or more SREBP pathway gene. Gene expression profiling can also be used to identify other genes (or proteins) that may have a functional relation to (e.g. may participate in a signaling pathway with) or be a transcriptional target of an SREBP pathway gene. The genes are identified by detecting changes in their expression levels following mutation, i.e., insertion, deletion or substitution in, or over-expression, under-expression, mis-expression or knock-out, of an SREBP pathway gene.

Phenotypes Associated With SREBP Pathway Gene Mutations

After isolation of model animals carrying mutated or mis-expressed SREBP pathway genes or inhibitory RNAs, animals are carefully examined for phenotypes of interest. For analysis of SREBP pathway genes that have been mutated (i.e. deletions, insertions, and/or point mutations) animal models that are both homozygous and heterozygous for the altered SREBP pathway gene are analyzed. Examples of specific phenotypes that may be investigated include lethality; sterility; and changes in various characteristics of the animal such as motility, body shape, body size and weight, metabolism, lipid accumulation, feeding, development, morphogenesis of organs, brood size, thermotaxis, etc. Some phenotypes more specific to flies include alterations in: morphogenesis of the peripheral sensory organs, imaginal discs, eye development, wing development, leg development, bristle development, antennae development, gut development, fat body, and musculature. Some phenotypes more specific to nematodes include: alterations in chemotaxis, a dauer constitutive phenotype, a dauer defective phenotype, and a pale-intestine phenotype. A phenotype of particular interest in *C. elegans* is the pale intestine phenotype, which is indicative of defects in lipid metabolism and is discussed in more detail below and in the Examples.

Genomic sequences containing an SREBP pathway gene can be used to confirm whether an existing mutant Drosophila or *C. elegans* line corresponds to a mutation in one or more SREBP pathway genes, by rescuing the mutant phenotype. Briefly, a genomic fragment containing the SREBP pathway gene of interest and potential flanking regulatory regions can be subcloned into any appropriate Drosophila or *C. elegans* transformation vector, and injected into the animals. For Drosophila, an appropriate helper plasmid is used in the injections to supply transposase. Resulting transformants are crossed for complementation testing to an existing panel of Drosophila or *C. elegans* lines whose mutations have been mapped to the vicinity of the gene of interest (Fly Pushing: The Theory and Practice of Drosophila Genetics, (1997) Cold Spring Harbor Press, Plainview, N.Y.; and *Caenorhabditis elegans*: Modem Biological Analysis of an Organism, supra. If a mutant line is discovered to be rescued by this genomic fragment, as judged by complementation of the mutant phenotype, then the mutant line likely harbors a mutation in the SREBP pathway gene. This prediction can be further confirmed by sequencing the SREBP pathway gene from the mutant line to identify the lesion in the SREBP pathway gene.

Identification of Genes That Modify SREBP Pathway Genes

The characterization of new phenotypes created by mutations in SREBP pathway genes enables one to test for genetic interactions between SREBP pathway genes and other genes that may participate in the same, related, or interacting genetic or biochemical pathway(s). Individual genes can be used as starting points in large-scale genetic modifier screens as described in more detail below. Alternatively, RNAi methods can be used to simulate loss-of-function mutations in the genes being analyzed. It is of particular interest to investigate whether there are any interactions of SREBP pathway genes with other well-characterized genes, particularly genes involved in lipid metabolism. For example, a candidate gene that may be tested for interaction with the SREBP pathway is the insulin receptor gene (referred to as in in Drosophila, and daf-2 in C. elegans).

Genetic Modifier Screens

A genetic modifier screen using invertebrate model organisms is a particularly preferred method for identifying genes that interact with SREBP pathway genes, because large numbers of animals can be systematically screened making it more likely that interacting genes will be identified. In C. elegans and Drosophila, a screen of up to about 10,000 animals is considered to be a pilot-scale screen. Moderate-scale screens usually employ about 10,000 to about 50,000 flies or up to about 100,000 worms, and large-scale screens employ greater than about 50,000 or 100,000 flies or worms, respectively. In a genetic modifier screen, animals having a mutant phenotype due to a mutation in one or more SREBP pathway genes are further mutagenized, for example by chemical mutagenesis or transposon mutagenesis. The mutagenesis procedures used in typical genetic modifier screens of C. elegans are well known in the art. One method involves exposure of hermaphrodites that carry mutations in one or more SREBP pathway genes to a mutagen, such as EMS or trimethylpsoralen with ultraviolet radiation (Huang and Stemberg, Methods in Cell Biology (1995) 48:97–122). Alternatively, transposable elements are used, oftentimes by the introduction of a mutator locus, such as mui-2, which promotes mobility of transposons (Anderson, Methods in Cell Biology (1995) 4:31–58).

In Drosophila, the mutagenesis methods and other procedures used in a genetic modifier screen depend upon the precise nature of the mutant allele being modified; these methods are discussed in more detail below under the Drosophila genetic modifier screen subheading.

Progeny of the mutagenized animals are generated and screened for the rare individuals that display suppressed or enhanced versions of the original mutant SREBP pathway phenotype. Such animals are presumed to have mutations in other genes, called "modifier" genes, that participate in the same phenotype-generating pathway. The newly-identified modifier genes can be isolated away from the mutations in the SREBP pathway genes by genetic crosses, so that the intrinsic phenotypes caused by the modifier mutations can be assessed in isolation.

Modifier genes can be mapped using a combination of genetic and molecular methods known in the art. Modifiers that come from a genetic screen in C. elegans are preferably mapped with visible genetic markers and/or with molecular markers such as STS markers (The Nematode Caenorhabditis elegans, supra; Caenorhabditis elegans: Modern Biological Analysis of an Organism, supra). Modifier genes may be uncovered by identification of a genomic clone which rescues the mutant phenotype, as described above. Alternatively, modifier genes that are identified by a Te1-based screen can be uncovered using transposon display technology (Korswagen et al., Proc Natl Acad Sci U.S.A. (1996) 93(25):14680–5).

Standard techniques used for the mapping of modifiers that come from a genetic screen in Drosophila include meiotic mapping with visible or molecular genetic markers; complementation analysis with deficiencies, duplications, and lethal P-element insertions; and cytological analysis of chromosomal aberrations (Fly Pushing: Theory and Practice of Drosophila Genetics, supra; Drosophila: A Laboratory Handbook, supra). Genes corresponding to modifier mutations that fail to complement a lethal P-element may be cloned by plasmid resuce of the genomic sequence surrounding that P-element. Alternatively, modifier genes may be mapped by phenotype rescue and positional cloning (Sambrook et al., supra).

Newly identified modifier mutations can be tested directly for interaction with other genes of interest known to be involved or implicated in the SREBP using methods described above. Also, the new modifier mutations can be tested for interactions with genes in other pathways that are not believed to be related to SREBP signaling (e.g. Notch in Drosophila, and tin in C. elegans). New modifier mutations that exhibit specific genetic interactions with other genes implicated in lipid metabolism, but not interactions with genes in unrelated pathways, are of particular interest.

The modifier mutations may also be used to identify "complementation groups". Two modifier mutations are considered to fall within the same complementation group if animals carrying both mutations in trans exhibit essentially the same phenotype as animals that are homozygous for each mutation individually and, generally, are lethal when in trans to each other (Fly Pushing: The Theory and Practice of Drosophila Genetics, supra). Generally, individual complementation groups defined in this way correspond to individual genes.

When SREBP pathway modifier genes are identified, homologous genes in other species can be isolated using procedures based on cross-hybridization with modifier gene DNA probes, PCR-based strategies with primer sequences derived from the modifier genes, and/or computer searches of sequence databases. For therapeutic applications related to the function of SREBP pathway, human and rodent homologues of the modifier genes are of particular interest. For pesticide and other agricultural applications, homologues of modifier genes in insects and arachnids are of particular interest. Insects, arachnids, and other organisms of interest include, among others, Isopoda; Diplopoda; Chilopoda; Symphyla; Thysanura; Collembola; Orthoptera, such as *Blattella germanica*; Dermaptera; Isoptera; Anoplura; Mallophaga; Thysanoptera; Heteroptera; Homoptera, including *Bemisia tabaci*, and *Myzus* spp.; Lepidoptera including *Plodia interpunctella*, *Pectinophora gossypiella*, Plutelia spp., Heliothis spp., and Spodoptera species; Coleoptera such as *Leptinotarsa decemlineata*, Diabrotica spp., Anthonomus spp., and Tribolium spp.; Hymenoptera, including *Apis mellhfera*; Diptera, including Anopheles spp.; Siphonaptera, including *Ctenocephalides felis*; Arachnida; and Acarinan, including *Amblyoma americanum*; and nematodes, including Meloidogyne spp., and *Heterodera glycinii*.

Genetic Modifier Screens in Drosophila

The procedures involved in typical Drosophila genetic modifier screens are well-known in the art (Wolfner and Goldberg, Methods in Cell Biology (1994) 44:33–80; and Karim et al., Genetics (1996) 143:315–329). The procedures used differ depending upon the precise nature of the mutant allele being modified. If the mutant allele is genetically recessive, as is commonly the situation for a loss-of-function allele, then most typically males, or in some cases females, which carry one copy of the mutant allele are exposed to an effective mutagen, such as EMS, MMS, ENU, triethylamine, diepoxyalkanes, ICR-170, formaldehyde, X-rays, gamma rays, or ultraviolet radiation. The mutagenized animals are crossed to animals of the opposite sex that also carry the mutant allele to be modified. In the case where the mutant allele being modified is genetically dominant, as is commonly the situation for ectopically expressed genes, wild type males are mutagenized and crossed to females carrying the mutant allele to be modified.

The progeny of the mutagenized and crossed flies that exhibit either enhancement or suppression of the original phenotype are immediately crossed to adults containing balancer chromosomes and used as founders of a stable genetic line. In addition, progeny of the founder adult are retested under the original screening conditions to ensure stability and reproducibility of the phenotype. Additional secondary screens may be employed, as appropriate, to confirm the suitability of each new modifier mutant line for further analysis.

Although the above-described Drosophila genetic modifier screens are quite powerful and sensitive, some genes that participate in the SREBP pathway may be missed in this approach, particularly if there is functional redundancy of those genes. This is because the vast majority of the mutations generated in the standard mutagenesis methods will be loss-of-function mutations, whereas gain-of-function mutations that could reveal genes with functional redundancy will be relatively rare. Another method of genetic screening in Drosophila has been developed that focuses specifically on systematic gain-of-function genetic screens (Rorth et al., Development (1998) 125:1049–1057). This method is based on a modular mis-expression system utilizing components of the GAL4/UAS system (described above) where a modified P element, termed an "enhanced P" (EP) element, is genetically engineered to contain a GAL4-responsive UAS element and promoter. The resulting transposon is used to randomly tag genes by insertional mutagenesis (similar to the method of P element mutagenesis described above). Thousands of transgenic Drosophila strains, termed EP lines, can be generated, each containing a specific UAS-tagged gene. This approach takes advantage of the preference of P elements to insert at the 5'-ends of genes. Consequently, many of the genes that are tagged by insertion of EP elements become operably fused to a GAL4-regulated promoter, and increased expression or mis-expression of the randomly tagged gene can be induced by crossing in a GAL4 driver gene.

Systematic gain-of-function genetic screens for modifiers of phenotypes induced by mutation or mis-expression of an SREBP pathway gene can be performed by crossing several thousand Drosophila EP lines into a genetic background containing a mutant or mis-expressed SREBP pathway gene, and further containing an appropriate GAL4 driver transgene. The progeny of this cross are then analyzed for enhancement or suppression of the original mutant phenotype as described above. Those identified as having mutations that interact with the SREBP pathway can be crossed further to verify the reproducibility and specificity of this genetic interaction. EP insertions that demonstrate a specific genetic interaction with a mutant or mis-expressed SREBP pathway gene, have a physically tagged a new gene which can be identified and sequenced using PCR or hybridization screening methods, allowing the isolation of the genomic DNA adjacent to the position of the EP element insertion.

BODIPY-fatty Acid Conjugates for Determining Lipid Content of Nematodes

Because defects in the SREBP pathway can result in abnormal metabolism of lipids, a method for readily identifying mutant model organisms that exhibit abnormalities in lipid metabolism would be beneficial. Prior methods for assessing lipid content in nematodes includes the use of non-vital stains such as Sudan Black (Kimura et al., Science (1997) 277:942–6).

However, the drawbacks of these techniques are that the nematodes must be fixed prior to staining. Fixation can introduce artifacts, making an accurate assessment difficult, and furthermore, kills the animals making it impossible to carry out further genetic analysis on the animals that are tested. In order to avoid these problems associated with fixing nematodes, certain vital stains were tried that are routinely used for staining lipid in cultured cells such as Nile Red (Greenspan et al., J Cell Biol, (1985) 100:965–973). However, it was found that these dyes tended to result in background fluorescence of gut granules which are autofluorescent organelles of the intestinal epithelial cells that are thought be to lysosomes. In many cases, these fluorescent vital stains appeared to be concentrated in gut granules, enhancing their fluorescence and causing difficulty in accurately measuring the fluorescence due to lipid droplet staining in the intestine. Accordingly, the invention provides an improved method for measuring lipid storage in live nematodes. It has been found that BODIPY® dyes conjugated to fatty acids (e.g. BODIPY® FL C12 (4,4-difluoro-5,7-dimethyl-4-bora-3a,4a-diaza-s-indacene-3-dodecanoic acid), and C1-BODIPY® 500/510 C12 (4,4-difluoro-5-methyl-4-bora-3a,4a-diaza-s-indacene-3-dodecanoic acid) Molecular Probes, Eugene, Oreg.) concentrate in lipid droplets in the intestines of living nematodes. These dyes do not have the drawbacks associated with other vital dyes because, in addition to clearly staining and fluorescing in lipid droplets in the intestine, they quench the background fluorescence due to the gut granules. Accordingly, the invention provides a method of using BODIPY®-fatty acid conjugates to stain live nematodes for determining the relative and absolute lipid content in response to changes in metabolic conditions brought on by a) changes in genetic backgrounds including mutations in genes essential for control of metabolic processes, b) changes in environmental conditions such as food sources, temperature, and crowding conditions, and c) different developmental states including the dauer larva. This method is particularly valuable in uses that involve genetic screens and compound screens based on changes in metabolic processes such as the SREBP processing pathway, among others. The method allows considerable increases in accuracy of lipid quantification in vivo over the use of other fluorescent lipophilic stains, making automated sorting of the nematodes based on fluorescence feasible.

BODIPY® conjugates have previously been used to study (1) lipid content in the surface membrane of Shistosoma mansoni worms (Redman and Kusel, Parasitology (1996) 113(2):137–143), (2) lipid endocytosis in cultured mammalian fibroblasts (Pagano and Chen, Ann N Y Acad Sci (1998) 845:152–160), (3) lipid trafficking between the Golgi apparatus and plasma membrane of cultured mammalian fibroblasts (Pagano et al., J. Cell. Biol (1991) 113(6): 1267–1279), (4) fatty acid transport by Saccharomyces (Faergeman et al., J. Biol. Chem (1997) 272(13): 8531–8538) and (5) distribution of ivermectin in muscle vesicle membranes of Ascari suum (Marin and Kusel, Parasitology (1992) 104(3):549–555). However, these prior uses of BODIPY® conjugates do not suggest the applicability of BODIPY® conjugates, and in particular, BODIPY® fatty acid conjugates, for quantification of lipid storage in nematodes. Moreover, the fact that BODIPY® fatty acid conjugates quenches background fluorescence from lysosomes, providing for more accurate quantification, is an unexpected and important advantage provided by the invention that permits large-scale, automated sorting of animals based on fluorescence.

BODIPY® fatty acid conjugates can be used to stain nematodes of different genetic backgrounds for use in genetic screens, both de novo screens for mutations affecting lipid content of whole nematodes and modifier screens for mutations that change lipid accumulation in mutant nematodes (for example, the insulin receptor (daf-2) or the SREBP homolog (pin-1) nematodes). The intestines of the nematodes can be visually examined for lipid content under a fluorescent microscope and mutant animals can be subsequently propagated for cloning purposes. This method can be used in conjunction with automatic flow sorter technology to rapidly separate large numbers of living nematodes by lipid content. This would be useful either for automated high throughput genetic screening or for large scale automated separation of dauer larvae from other developmental stages. Additionally, the method can be used to determine changes in lipid accumulation in nematodes exposed to inhibitory compounds that might serve as therapeutic agents for the control of diabetes, obesity, lipid storage diseases, or other human or animal diseases. A test compound can be administered to a nematode by direct contact, ingestion, injection, or any suitable method and changes in lipid content of the nematode or its progeny are observed. Further, the method is applicable to reverse genetic screening using inhibitory RNA. For example, nematodes could be exposed to combinations of large numbers of RNAs in 384-well plates and screened for changes in lipid content mediated by RNAi using fluorometry or direct visual observation.

EXAMPLES

The following examples show how the nucleic acid sequences of SEQ ID NOs 1, 3, and 5 were isolated, and how these sequences, and derivatives and fragments thereof, as well as other SREBP pathway nucleic acids and gene products can be used for genetic studies to elucidate mechanisms of the SREBP pathway as well as the discovery of potential pharmaceutical or pesticidal agents that interact with the pathway. As used herein, all *C. elegans*-derived gene sequences are designated by the letters "ce" in front of the gene sequence. Likewise, all Drosophila-derived gene sequences are designated by the letter "d" in front of the gene sequence. These Examples are provided merely as illustrative of various aspects of the invention and should not be construed to limit the invention in any way.

Example 1

Cloning of C. Elegans SREBP

The *C. elegans* genomic database was searched with the protein sequence of the human SREBP-1, SREBP-2, and *Drosophila melanogaster* SREBP homologue, HLH106, using the TBLASTN search tool (Altschul et al., supra). One *C. elegans* open reading frame showed significant homology with all three of the above SREBP proteins. This homology extends throughout most of the SREBP protein sequences. The *C. elegans* open reading frame is located on two overlapping clones on the right arm of chromosome III (Y47D3 and H10N23). At the time of the search, there were no previous annotations, gene predictions, or candidate mutants that mapped to this region that would suggest previous identification of this open reading frame as an SREBP-related gene.

Using BLAST analyses (Altschul et al., supra) and the GENSCAN Genefinder program (Burge and Karlin, J. Mol. Biol. (1997) 268(1):78–94), a predicted exon-intron structure for the *C. elegans* SREBP-related gene (ceSREBP) was generated. This *C. elegans* homologue of SREBP cDNA was cloned in order to validate its existence as an expressed mRNA, and to determine the cDNA and protein sequence for the elucidation of ceSREBP function. Moreover, cloning of ceSREBP is a prerequisite for future genetic manipulations that require knowledge of the sequence, such as RNAi experiments, generation of misexpression constructs, isolation of Te1 insertion or chemical deletion mutants, etc.

Cloning Strategy:

The N-terminal and C-terminal ends of ceSREBP were cloned using gene-specific internal primers and non-specific primers at 3' and 5' ends. Internal primers were made to regions of high homology according to the GENSCAN prediction for ceSREBP, that were also predicted by the ACEDB Genefinder (Richard Durbin and Jean Thierry Mieg (1991-present), A *C. elegans* Database Documentation, code and data available from anonymous FTP servers at lirmm.lirmm.limm.fr, cele.mrc-lmb.cam.ac.uk and ncbi.nlm.nih.gov). They were designed to amplify the ends of the cDNA, not the full-length cDNA. Once the end sequence was known, the full-length cDNA was amplified in overlapping N-terminal and C-terminal parts using gene-specific primer pairs. The template for amplification was a mixed-stage, 1 st strand cDNA pool that was synthesized from poly-A+RNA using the NotI primer/adapter (Life Technologies, Gaithersburg, Mich.).

N-terminal:

Antisense, internal primer for amplification of the N-terminal was made to sequence encoding the ceSREBP bHLHz region: GTACGACGCTCGGTTTTGGTC (SEQ ID NO:31). Sense primer no. 1 was the 5' splice leader (SL1) sequence:

GGTTTAATTACCCAAGTTTGAG (SEQ ID NO:32). Amplifications were performed using Expand™ buffers and enzyme mixes (Roche, Summerville, N.J.). Amplification conditions were as follows:

---

2 µl *C. elegans* (ce) mixed-stage 1st strand cDNA
5 µl 2 mM dNTPs
5 µl Expand ™ High Fidelity 10x buffer with MgCl$_2$
3 µl SL1, 5 µM
3 µl ceSREDP, 5 µM
0.75 µl Expand ™ High Fidelity enzyme mix
31.25 µl H$_2$O
94° C. 2 min
10 cycles of:    94° C. 1 sec
                 52° C. 30 sec
                 68° C. 4 min
25 cycles of:    94° C. 15 sec
                 52° C. 30 sec
                 68° C. 4 min + 20 sec/cycle
72° C. 5 min
4° C. hold
1 µl Amplitaq ™ (Perkin-Elmer, Foster City, CA) added with an additional incubation for 10 min at 72° C.

---

PCR products were run on a 1% agarose gel. The major product was a band of about 1 kb in size.

C-terminal:

Sense primer no. 2, was an internal primer made to a region of homology between human SREBP1 and Genscan-predicted ceSREBP, encoding LCAVNLAE (SEQ ID NO:92): CCTCTGTGCAGTAAACCTTGCTG (SEQ ID NO:93). The non-specific antisense primer, pN1, was made to the 5' end of the NotI primer/adapter: GACTACTTCTA-GATGGCGAGC (SEQ ID NO:9). The same amplification conditions as for the N-terminal were used using these primers. The product of this amplification was 1.3 kb in size.

Cloning and Sequencing:

PCR fragments were gel-purified by beta-agarase treatment (NEB, Beverly, Mass.) cloned into the pCR2.1 vector (Invitrogen, San Diego, Calif.) essentially according to manufacturer's protocols for ligation and transformation into E. coli. Individual colonies were screened for an insert of the correct size by PCR using M 13 forward and reverse primers to pCR2.1. Individual colonies from each transformation were grown up overnight in 3 ml LB-Amp, and DNA was prepared using Easy-Pure Preps™ (super mini) (Primm Labs, Cambridge, Mass.). DNA preps were digested using EcoRI enzyme to check for clones with correct insert size. Clones were end-sequenced with Big Dye™ dye-terminator sequencing kit (ABI, Foster City, Calif.) using M13 forward and reverse primers to pCP2.1.

```
1 µl miniprep DNA (~100 ng)
1 µl Big Dye ™
1 µl primer, 0.8 µM
0.5 µl 5× buffer (400 mM Tris, pH 9; 10 mM MgCl₂)
1.5 µl H₂O.
96° C. for 5 min
25 cycles of:       96° C. for 30 sec
                    50° C. for 15 sec
                    60° C. for 4 min
```

Reactions were ethanol precipitated and sequenced. Sequencing products were analyzed using Sequencher program (Gene Codes Corporation, Ann Arbor, Mich.) and BLAST (Altschul et al, supra). A single N-term contiguous sequence ("contig") was assembled that shared sequence identity with the YAC sequence Y47D3 (GI:3646936) from which gene predictions were made, and was virtually identical to the gene prediction in this region. Two non-overlapping C-terminal contigs were assembled, one of which contained the sequence of sense primer no.2; the other, pN1. Both shared identity with Y47D3 in BLAST searches to C. elegans genomic sequence and showed homology to SREBP sequences from other species. A likely termination codon and possible poly-A signals were identified.

Amplification of Full-length cDNA:

A longer C-terminal fragment was amplified which overlapped with the N-terminal fragment and contained the remainder of the unknown sequence. The ~2.9 kb fragment was amplified using the same conditions as for the N- and C-terminals but with the primers described below. Another difference is that 3 µl ce mixed stage 1 st strand cDNA was used rather than 2 µl. The primers used were a sense primer within the ~1 kb N-terminal fragment, and referred to as Y47-4, and a primer referred to as ceSREBP7, which includes the predicted termination codon:

Y47-4: AGCAATGGAACATATCAACGGG (SEQ ID NO:33)

ceSREBP7: CAATTCAAAGATCCATAGAAGTATG (SEQ ID NO:34).

The ~2.9 kb fragment was cloned into the pCR2.1 vector as described above.

Sequencing the Full-length cDNA:

To obtain complete sequence of the full-length gene of ceSREBP, the following set of seven sequencing primers (ceSREBPs1–s7; contained within SEQ ID NO:1) were synthesized based on sequences derived from the original N-terminal and C-terminal contigs, and to the most highly conserved regions of the predicted gene.

sense ceSREBPs1: GCATGTTCAGCGACGAATGG (SEQ ID NO:35)

ceSREBPs2: GCAACACTACGACGGGCTAT (SEQ ID NO:36)

ceSREBPs3: TGGATTGCTCGCTGGAAGTG (SEQ ID NO:37)

ceSREBPs4: GGAACTTGTCGGTGGTGACG (SEQ ID NO:38)

antisense ceSREBPs5: CCCTTGAAGCTTTGTGTCCA (SEQ ID NO:39)

ceSREBPs6: CGTGGAAGTCCGTCGTTTGA (SEQ ID NO:40)

ceSREBPs7: GGTCACCATGGATCAGCAGT (SEQ ID NO:41)

These primers, as well as M13 forward and reverse, were used to sequence clones containing the ~1.3 and the ~2.9 kb C-terminal fragments using the above-described sequencing methods. When aligned with previously obtained sequence, these yielded a single open reading frame (ORF) of ~3.4 kb in size which. BLAST analysis against GenBank sequences, showed highest homology to other SREBPs.

Error-free cDNA Clones:

All the C-terminal clones that contributed to the above contig contained PCR errors (i.e., single nucleotide discrepancies from the other clones). To obtain error-free sequence the ~3 kb C-term fragment was re-amplified using the high-fidelity ePfu enzyme (Stratagene) and, as template, a commercial mixed stage cDNA library (Stratagene), in addition to the 1 st strand cDNA pool.

Reaction 1

2 µl library cDNA

5 µl 10 ×Pfu buffer

10 µl 2 mM dNTPs

10 µl Y47-4, 5 µM

10 µl ceSREBP7, 5 µM

1 µl Pfu 12 1 H₂O

Reaction 2 was the same as the first with the exception that 0.5 µl Amplitaq™ was used, and 0.5 µl Pfu was used instead of 1 µl.

For both reactions:

```
94° C. 2 min
35 cycles of:       94° C. 15 sec
                    55° C. 30 sec
                    72° C. 6 min
72° C. 10 min
4° C. hold
1 µAmplitaq ™ added with an additional
incubation for 10 min at 72° C.
```

The fragments from both reactions were cloned into the pCRII vector as described above for the pCR2.1 vector. One clone from each of the above reactions was sequenced through using the following primers:

M13 forward and reverse; ceSREBPs1, s2, s3, s4, s6, s7 (above); and the following additional primers ceSREBPs9–s15 (contained within SEQ ID NO:1):

Sense ceSREBPs9: CGTTGGATCGATCGCTTCCA (SEQ ID NO:42)

ceSREBPs10: CCGCCGAAGATTTTGACAGA (SEQ ID NO:43)

ceSREBPs11: TGGGACAAGGGGAGATTGTT (SEQ ID NO:44)

Antisense ceSREBPs12: GAACGTGCGTCCACCATGTG (SEQ ID NO:45)

ceSREBPs13: GCTCCAACCTTTTCGCATCT (SEQ ID NO:46)

ceSREBPs14: GGAGATGATTCGACGGGTGA (SEQ ID NO:47)

ceSREBPs15: TCCCCGGAATCACTATCCTC (SEQ ID NO:48)

These sets of reactions gave full sequence in both directions and gave identical sequence from the two clones.

Two clones were also sequenced that contained the ~1 kb N-terminal fragment with the following additional primers (contained within SEQ ID NO:1):

Sense ceSREBPs8: GCAGCGTCGCTTTTTGTTAA (SEQ ID NO:49)

Antisense ceSREBPs16: TGATGGTGGTGATGAGGTGG (SEQ ID NO:50)

ceSREBPs17: AATTGTTGGGTGGCGGCTAG (SEQ ID NO:53)

These reactions, together with sequence from M13 forward and reverse primers, gave a full sequence in both directions that was nearly identical to the posted, unfinished sequence from Y47D3. The cDNA sequence of the ceSREBP gene is provided in SEQ ID NO:1. The cDNA is 3419 nucleotides long. This full-length clone contained a single open reading frame with an apparent translation al initiation site at nucleotide position 24 and a stop signal at nucleotide position 3365. The predicted polypeptide precursor is 1113 amino acids long. Additional features include an acidic domain at about nucleotides 24 to 233 (amino acid residues 1 to 69); a possible second acidic domain at about nucleotides 987 to 1040 (amino acid residues 321 to 338); a basic Helix-loop-helix domain at about nucleotides 1089 to 1286 (amino acid residues 355 to 421); a first transmembrane domain at about nucleotides 1455 to 1514 (amino acid residues 477 to 497); and a second transmembrane domain at about nucleotides 1653 to 1706 (amino acid residues 543 to 561).

A BLAST analysis against the Y47D3 clone which has a total of 351,956 nucleotides, revealed 12 regions of Y4D3 which share sequence identity with SEQ ID NO:1, as shown in Table II.

TABLE II

| Base # of SEQ ID NO: 1 | Base # of Y47D3 | % Sequence Identity |
|---|---|---|
| 1–80 | 179,410–179,331 | 100 |
| 81–213 | 178,918–178,786 | 100 |
| 214–523 | 178,528–178,218 | 100 |
| 527–632 | 177,448–177,338 | 96 |
| 633–1052 | 177,286–176,864 | 100 |
| 1053–1288 | 176,520–176,285 | 100 |
| 1289–1482 | 175,768–175,568 | 100 |
| 1483–2011 | 175,523–174,994 | 100 |
| 2012–2408 | 174,687–174,288 | 100 |
| 2409–2636 | 174,228–174,001 | 100 |
| 2637–2790 | 173,954–173,801 | 100 |
| 2791–3151 | 155,054–154,694 | 100 |
| 3152–3397 | 154,638–154,393 | 100 |

An alignment of the predicted protein sequence (SEQ ID NO:2) against the human and Drosophila SREBP proteins was performed. Amino acid residues 353 to 423 of SEQ ID NO:2 share 45% and sequence identity and 77% sequence similarity with amino acid residues 281–351 of Drosophila melanogaster SREBP (SEQ ID NO:8; Theopold et al., supra; GI079656). Amino acid residues 466 to 826 of SEQ ID NO:2 share 28% sequence identity and 47% sequence similarity with human SREBP2 (GI1082805). The presence of other gene and protein sequences bearing significant homology to ceSREBP was investigated using the BLAST family of computer programs (Altschul et al., supra). The amino acid sequence of a sterol regulatory element-binding protein-1 (SREBP-1) from Mus musculus (GI4240012) was most similar, sharing 52% sequence identity and 71% sequence similarity with amino acid residues 335–428 of SEQ ID NO:2 and having up to 5 contiguous identical amino acids in common with SEQ ID NO:2. Sequence similarity, to a lesser extent, was revealed between SEQ ID NO:2 and sequences from U.S. Pat. No. 5,780,262 (GI3998144), and others.

The presence of other gene and protein sequences bearing significant homology to ceSREBP was investigated using the BLAST family of computer programs against public databases. The following amino acid sequences were the most similar: SREBP-1, Chinese Hamster (GI1083186); SREBP-1, Cricetulus griseus (GI516003); Sequence 54 from U.S. Pat. No. 5,527,690 (GI610915); SREBP2 precursor, human (GI082805); SREBP-2, Homo sapiens (GI451330); SREBP2 precursor, Chinese hamster (GI1083185); Sequence 38 from U.S. Pat. No. 5,527,690 (GI1610908); SREBP-1, Homo sapiens (GI409405); SREBP-2, Cricetulus griseus (GI551506); Transcription factor ADD1, Rat (GI540006); and HLH106, Drosophila Melanogaster (GI107965).

Subsequent to the above analysis, a Genefinder prediction of the ceSREBP protein was entered into the Genbank database, which is 100% identical to SEQ ID NO:2, and is designated GI3881008.

Example 2 ceSREBP Expression Analisis

Strategy

Expression of ceSREBP was assayed using a transcriptional reporter system in which the putative promoter/enhancer region of ceSREBP was fused to GFP. To determine how much genomic sequence to include in the reporter construct, the Y47D3 contig containing the N-terminal region of the ceSREBP cDNA and ~25 kb upstream of the ceSRPEBP initiation codon, was analyzed using ACEDB Genefinder and GENSCAN programs (Burge and Karlin, supra). There were no known genes within this region, and no predicted genes reported by either program. Of the two predicted genes within 8 kb of ceSREBP, one, 5 kb upstream of ceSREBP showed limited homologies by BLAST analysis to C. elegans expressed sequence tags (EST). A genomic fragment of 4.5 kb was chosen as the putative promoter/enhancer region.

Amplification of Genomic Enhancer Promoter Region

PCR primers were designed to amplify the 4.5 kb genomic fragment, including the first few amino acids of ceSREBP. Restriction sites were included in the primers to facilitate subcloning into the GFP reporter vector pPD117.01 (from the laboratory of Dr. Andrew Z. Fire (Fire Lab)), Carnegie Institution of Washington, Baltimore, Md.) in an in-frame translation al fusion to GFP. The sense primer, nucleotides 71,242–71,265 of Y47D3 (GI:3646936), contained an AscI site; the antisense primer, nucleotides 66,719–66,747 of Y47D3, contained a KpnI/Asp718 site:

ceSREBPp1: ATGGGCGCGCCAACCAAAGTGTGAT-GCAACAG (SEQ ID NO:28)

ceSREBPp2: GAGGGTACCTCGTTCATTCT-GAAAAAAAAAAGTC (SEQ ID NO:29)

Amplification was done in duplicate to provide two independently-amplified promoter fragments for independent confirmation of the expression pattern; conditions were as follows:

```
2 µl N2 genomic DNA (50 ng/µl)
5 µl 10× Klentaq ™ buffer (Clontech, Palo Alto, CA)
1 µl 10 mM dNTPs
5 µl ceSREBPp1, 5 µM
5 µl ceSREBPp2, 5 µM
1 µl Klentaq ™ enzyme
31 µl H2O
94° C. 2 min
25 cycles of:           94° C. 15 sec
                        52° C. 1 min
                        72° C. 5 min
72° C. 10 min
4° C. hold
1 µl Amplitaq ™ added with an additional incubation
for 10 min at 72° C.
```

One half of each reaction was run on a 1% Seaplaque GTG, 1×TAE gel, and the major product at ~4.5 kb excised. The fragments were purified using Geneclean (Biol101) and subcloned into the pCRII vector essentially according to manufacturer's protocols (Invitrogen) for ligation and transformation. DNA from individual colonies from each transformation was prepared using Easy-Pure preps (super mini). DNA preps were checked using AscI+Asp718 and AscI+NotI restriction digests. Clones that appeared as expected by digest were end-sequenced with Big Dye™ dye-terminator sequencing kit using M13 forward and reverse primers to pCRII.

Sequences were analyzed using Sequencher. From each original PCR reaction, a single clone that contained the expected insert was identified.

To subclone the promoter fragment into the GFP reporter vector, this vector, and the promoter fragments in pCRII were digested with AscI+Asp718, gel-purified using Geneclean (Bio101), ligated together and transformed into E. coli using standard procedures. DNA from individual colonies from each transformation was prepared using Easy-Pure™ preps (super mini). DNA preps were checked using AscI+Asp718, HincII, ClaI, DrahIII, EcoRI, and HindIII restriction digests. Several clones from each original PCR reaction were checked by end-sequencing with primers that sequenced through the two cloning junctions. Colonies of clones that looked correct by sequence analysis were re-streaked. DNA from individual colonies was prepared by Qiagen midi preps and checked by restriction digest.

Expression Analysis—ceSREBP::GFP

By GFP expression analysis, ceSREBP is first expressed weakly in embryonic gut cells at the time of gut cell polarization, which marks the beginning of differentiation. There is strong fluorescence by the "bean stage" which persists in all intestinal cells throughout embryogenesis and at all larval and adult stages. There is also weak fluorescence in the pharynx. Because there is high specificity of expression of ceSREBP in intestinal cells, the ceSREBP promoter, contained within nucleotides 66,719–71,265 of Y47D3 (GI:3646936), has utility as a tissue specific promoter that can be operably linked to heterologous sequences, such as marker genes and/or genes of interest. Thus, the ceSREBP promoter can be used for studying biochemical pathways within the intestine of C. elegans.

Example 3

RNA Interference (RNAI) of C. Elegans SREBP, S2P and SCAP

Methods

PCR was carried out on C. elegans sequences for SREBP (SEQ ID NO:1) and S2P (Rawson et al., supra; GI1559384), and a Genbank sequence (GI3875380), that is annotated as having HMG-CoA reductase homology, and additionally has been determined to have homology to the human SCAP protein. Accordingly, GI3875380 is referred to herein as ceSCAP. Fragments of between 0.2kb to 2kb were produced in regions of interest. Primers used for each experiment are shown below. Each primer sequence had at either its 3' or 5' end (as indicated below) the T7 RNA polymerase binding site, ATCGATAATACGACTCACTATAGGG (SEQ ID NO:10), which is designated "T7-" below.

The remaining nucleotides in each primer sequence are from ceSREBP (SEQ ID NO:1), ceSCAP, or ceS2P, respectively.

SREBP5'A T7-CCAGCTCAAGGCCCATCAGG (SEQ ID No:52)

SREBP3'A T7-TCACTATCCTCATCATCCTC (SEQ ID NO:53)

SREBP5'B T7-GTACCCGCAACCAATCAATA (SEQ ID NO:54)

SREBP3'B T7-CTGATGAATTTCATGATAGA (SEQ ID NO:53)

ceSCAP:

SCAP5'A T7-CAGGACACTCCGCCTAACGA (SEQ ID NO:11)

SCAP3'A T7-ACTTACTCGTCAAATTACTC (SEQ ID NO:12)

SCAP5'B T7-GTGGCCTCCAGTTGCTCATG (SEQ ID NO:13)

SCAP3'B T7-CTTGTATTAGAAAAAAAGTG (SEQ ID NO:14)

D2013.8S T7-TGCCGCCCATCCAAAAGCCTGC (SEQ ID NO:15)

D2013.8A T7-TATACTTCGGAACCCCAAGTGG (SEQ ID NO:16)

ceS2P:

S2P5'T7-GCTCGGTCATGCGTGGGCGG (SEQ ID NO:17)

S2P3'T7-TAGCCGCCTCGACAGATTCC (SEQ ID NO:18)

S2P5'B T7-CACCGCACGGAAGCCGACGA (SEQ ID NO:19)

S2P3'B T7-CTCATTGAGCTGCCCCACAA (SEQ ID NO:20)

PCR was carried out with 0.5 µM each primer and 0.4 pg genomic DNA using the Expand™ PCR Kit (Roche) at the following conditions:

```
94° C. 1 min 15 sec
35 cycles of:           94° C. 15 sec
                        57° C. 45 sec
                        72° C. 1 min.
```

A small fraction of each reaction (2 to 5 µl) was run on a gel to assure that the PCR worked. The rest of each reaction was precipitated and then resuspended in RNase-free water, to serve as the template for production of sense and antisense RNAs. Sense and antisense RNA were transcribed separately from the DNA template using T7 and T3 RNA polymerases (Promega, Madison, Wis.; RNA production kit, Cat#1300) following the manufacturer's protocol. The resulting RNA samples were ethanol-precipitated and resuspended in 20 μl of RNAse- free TE (10 mM tris, 1 mM EDTA), followed by 10 μl of RNase free 3×IM annealing buffer (2 mM KPO4 pH7.5, 3 mM KCitrate pH 7.5, 2% PEG 6000). The reactions were mixed and incubated at 68° C. for 10 minutes and then at 37° C. for 30 minutes to anneal the sense and antisense strands. Alternatively, sense and antisense sequences were transcribed together with T7 sites on both strands following the same protocols.

Injection volumes were selected to deliver $0.5 \times 10^6$ to $1 \times 10^6$ molecules of RNA. Injections were delivered to the gonads or the intestinal cavity of *C. elegans*, and were carried out using the methods of Fire et al. (Development (1991) 113:503–514).

For germline RNAi, adult animals were microinjected with RNA into either the gonad or intestine using a glass needle mounted on a Medical Systems Corp. (Holliston, Mass.) PLI-90 injector. For RNAi of larvae, wild type L1 larvae were isolated by first collecting embryos from gravid adults by digestion in 1.25% sodium hypochlorite, 0.25M potassium hydroxide, and then allowing the embryos to hatch overnight in M9 buffer. Equal volumes of larvae in M9 buffer and RNA were mixed in wells of microtiter plates, incubated for 24 hours at 15 ° C., and then transferred to standard nematode growth plates.

For visualization of lipid, some of the worms were washed off a plate using M9 buffer (per liter: 30 gr $Na_2HPO_4$, 15 g $KH_2PO_4$, 2.5 g NaCl, 5 gr $NH_4Cl$), collected by centrifugation, and resuspended in a 2 ng/ml solution of BODIPY™.FL.C12; stock solution is 1 mg/ml in ethanol) prepared in M9 buffer. The worms were placed on a benchtop shaker is overnight at room temperature to absorb the dye. Images were captured using a fluorescence microscope (Axioplan™, Zeiss, Thomwood, N.Y.) the next day.

Results:

ceSREBP RNAi

Germline ceSREBP (pin-1) RNAi produces several visible phenotypes in the progeny of the microinjected animals. The gross phenotype is a fully penetrant larval arrest. Arrested larvae appear to be at the L2 stage based on gonad and cuticle morphology, although their length is more similar to that of L1 stage larvae. Arrested larvae remain motile and feeding for several days at 20° C. before dying. Their intestine appears paler, or less darkly pigmented, than wildtype, and this is referred to as the "pale intestine" or "Pin" phenotype.

Morphological defects in ceSREBP RNAi larvae (L1 and L2 stages) are confined to the intestine, where ceSREBP appears to be primarily expressed, and specifically affect three cytoplasmic structures in intestinal cells. First, there is a dramatic reduction in the number and average size of pigmented droplets in the intestine. This reduction of pigmented droplets seems to account for the Pin phenotype observed at low magnification. These droplets likely contain lipid since they stain with dye-labeled fatty acid (BODIPY™-dodecanoic acid) and their number in various developmental stages and mutants correlates with the level of staining with the dye Sudan black in fixed animals.

These observations indicate that ceSREBP is required for formation and/or maintenance of lipid droplets in the intestine, the main lipid storage organ of *C. elegans*. Second, the gut granules appear larger and more birefringent than in wildtype. Third, many variably sized vesicles appear in the intestine. These vesicles are spherical and transparent; similar vesicles are only rarely observed in wildtype larvae. The vesicles in ceSREBP RNAi larvae are usually each associated with a gut granule, and they show autofluorescence similar in color and intensity to that of gut granules. Since gut granules are thought to be lysosomal structures, the abnormal vesicles in ceSREBP RNAi larvae may also be lysosomal in origin. While many of the intestinal vesicles are immediately visible upon microscopic examination, the number and size of vesicles appears to increase over several minutes of observation, often as larvae begin to show signs of cellular degradation and death. Ultraviolet illumination accelerates this process in ceSREBP RNAi larvae and can also induce formation of similar vesicles in wildtype, although to a lesser extent. These observations may indicate that absorbance of visible or ultraviolet light by the birefringent, autofluorescent gut granules causes damage that induces swelling of lysosomes and synergizes with the effect of ceSREBP RNAi. The larval arrest and morphological defects in the intestine described above are also observed in mutant larvae homozygous for the pin-1 (ceSREBP) partial deletion allele ep79 (see Example 4), suggesting that germline RNAi phenocopies the zygotic null phenotype.

ceSREBP RNAi of larvae at the L1 stage results in apparently normal development through the L2 stage, with approximately normal accumulation of intestinal pigmented droplets. However, most larvae arrest at the L3 or L4 stage and fail to maintain their droplets. Arrested larvae, as well as many fully developed adults, show the Pin phenotype and have a thinner body than normal. The number and size of pigmented intestinal droplets is greatly reduced, as observed in earlier stages for germine RNAi. The finding that the Pin phenoptype can be induced by RNAi treatment after terminal differentiation of the intestine indicates that the phenotype is unlikely to be caused by a developmental defect in the intestinal cells. Rather, ceSREBP may be required continuously for proper functioning of the intestine. The pale, thin appearance of ceSREBP RNAi larvae and adults is similar to that of starved animals; however, the RNAi animals display foraging behavior and pump in bacteria through the pharynx into the intestine. These observations suggest that ceSREBP RNAi larvae are defective in digesting and/or metabolizing food. ceSREBP RNAi larvae show greater dispersal away from the food source than wildtype, possibly because they cannot derive nutrients from the bacteria. Transparent intestinal vesicles are observed less frequently with L1 ceSREBP RNAi than with germline ceSREBP RNAi, although most larvae and adults accumulate many vesicles within several minutes of microscope observation under visible or ultraviolet light. Gut granules of the arrested larvae and adults are ofter larger and more birefringent that normal. Adults that display the Pin phenotype have fewer embryos than normal in their uterus, suggesting reduced fecundity, and some of the embryos show variable developmental defects. Finally, Pin adults often contain large, transparent vacuoles in the anterior half of the intestine. These vacuoles are distinct from the abnormal vesicles observed in larvae, since the vacuoles are irregularly shaped and not autofluorescent, although their origin remains unidentified. ceSREBP RNAi of larvae at the L2 stage results in the same defects as L1 treatment, but mainly in later stages of development. Most animals arrest at the L4 stage or display the adult defects.

The daf-2 (e1370) temperature-sensitive mutation (described by Gems et al., Genetics (1998) 150:129–155) produces an opposite phenotype to that of ceSREBP RNAi, a dark intestine (Din) phenotype associated with increased accumulation of pigmented lipid droplets in the intestine. SREBP RNAI can suppress the Din phenotype of daf-2 (e1370), suggesting interaction between the pin-1/SREBP pathway and daf-2/insulin-like signaling pathway. Specifically, dcf-2 (e1370) larvae shifted to non-permissive temperature (25° C.) at the L1 stage constitutively form dauer larvae with dark intestines. ceSREBP RNAi of these larvae at the L1 stage results in Pin dauers with reduced intestinal lipid droplets. daf-2 (e1370) larvae shifted to non-permissive temperature at the L3 stage, after the critical period for commitment to dauer formation, form L4 larvae and adults with dark intestines. If the larvae are also treated with pin-1 RNAi at the L1 stage, then they can develop a less dark intestine at the L4 and adult stages. pin-1 does not appear to be strictly epistatic to daf-2-rather, double mutants show an intermediate phenotype. Some pin-1 (ep79) homozygotes escape larval arrest and can establish semi-viable strains of Pin animals with small, thin bodies and reduced brood size. Double mutants daf-2 (e1370) pin-1 (ep79) at 20° C. are partially suppressed for all these phenotypes and, in particular, show a less pale intestine. These results suggest that pin-1 and daf-2 interact to determine the level of lipid accumulation in the intestine.

ceS2P RNAi

Germline RNAi of the site 2 protease (S2P) homolog results in apparently normal development through the adult stage, however adults show a fully penetrant phenotype exhibiting all the defects observed for pin-1 larval RNAi (except larval arrest). Specifically, the adult phenotype includes a small, thin body, pale intestine associated with few lipid droplets, abnormally large and birefringent gut granules, large vacuoles in the anterior intestine, fewer embryos in the uterus, and variable developmental defects in some of the embryos. The gut granule defects seem more pronounced than observed for pin-1 RNAi. The striking similarity of the RNAi phenotypes for ceS2P and pin-1 strongly suggest that these two genes function in a common genetic pathway. The lack of effect of ceS2P RiNAi on larval development may indicate functional redundancy with an unidentified gene or reduced potency of RNAI for ceS2P compared to pin-1.

ceSCAP RNAi

Germline RNAi of the SCAP homologue generates a phenotype similar to ceS2P RNAi in less than 10% of adults. Defective adults display a pale intestine, small and thin body, few embryos in the uterus, and slightly more birefringent gut granules. Germline RNAi of both ceS2P and ceSCAP together produces a fully penetrant phenotype indistinguishable from pin-1 germline RNAi. This phenotype includes L2-L3 larval arrest, pale intestine associated with few or no intestinal lipid droplets, and abnormally large and birefringent gut granules. These results suggest that both the ceS2P and ceSCAP homologues function in the pin-1 genetic pathway at all larval and adult stages. If RNAi of ceS2P or ceSCAP produces the null phenotype for these genes, then there must exist other gene activities that can partially substitute for their functions, presumably in proteolytic cleavage at site 2 and 1 analogues, repectively, of PIN-1.

Example 4

Dominant Negative ceSREBP Phenotypes

A putative dominant negative form of ceSREBP (ccSREBP.DN) was constructed containing amino acids 90–480 of ceSREBP (SEQ ID NO:2). This form lacks the amino-terminal acidic transcriptional activation domain, as well as the C-terminal regulatory part which includes both transmembrane domains. This inactive version which, should not be subject to normal ceSREBP processing, is expected to dimerize with the wild type protein and thereby decrease overall transcriptional activity. ceSREBP.DN was amplified by PCR using sense primer CeSREBP5'DNSacI (CCCGAGCTCATGCGATTTTCCCCGCCAAACTTTG ATC (SEQ ID NO:56); contained within SEQ ID NO:1), and antisense primer CeSREBP3' CAMfeI (GGGCAA TTGCTAAAGGGTAACTTTCGAAGATCCATCTC (SEQ ID NO:57); contained within SEQ ID NO:1). The fragment was cloned into vector pPD99.52 (Fire Lab) behind the heat shock promoter hsp16/41, which allows temperature-induced activation of the downstreamn gene.

ceSREBP.DN was injected into N2 worms using standard protocols for *C. elegans* transformation (*Caenorhabditis elegans*: Modem Biological Analysis of an Organism, supra) at a concentration of 10 µg/ml plus 100 µg/ml pRF4 rol-6(d) transformation marker, and stable lines displaying the roller phenotype were established.

Misexpression of the ceSREBP.DN transgene was induced by incubating the worms carrying the transgene at 33–34° C. Worms were grown at 200° C. before and after the heat-shock. Embryos received a 30 minute heat-shock; larvae and adults received a 2–3 hr heat-shock. Worms were analyzed for several days after the heat shock under the dissecting microscope, to assess characteristics such as developmental stage, size, pigmentation, mobility (as an indicator of general health), and development of the germ line. Some worms were also analyzed using Nomarski optics on the Zeiss Axioplan™ to assess cellular defects, particularly in the intestine and germ line.

Results:

Results of heat-shock experiments are as follows and are characterized in terms of the phenotypes of the majority, and minority or variable phenotypes:

When embryos are heat-shocked, the majority of animals exhibit slow growth and become small adults with defective germlines and intestinal defects, including reduced lipid content and especially birefringent gut granules. A minority of the animals show embryonic arrest or larval lethality, or become adults with pale intestines.

When L1 larvae are heat-shocked, most animals exhibit slow growth and develop into small adults with defective germlines, a mottled appearance, and intestinal defects. A minority of animals have clear vesicles in their intestines.

When L2 larvae are heat-shocked, the majority of animals develop pale intestines as late larvae. A minority of animals exhibit slow growth, become adults with pale intestines, and/or small adults with defective germlines.

When L3 or L4 larvae are heat-shocked, the majority become adults with a mottled appearance and especially birefringent gut granules. A minority of animals exhibit slow growth, become adults with defective germlines, or become very pale and sickly adults.

The majority of heat-shocked adults display no consistent phenotypes, but have various instestinal and germline defects.

The pale intestine phenotype that results from misexpression of the dominant negative construct is consistent with the pale intestine phenotype that results from ceSREBP RNAi (described in Example 3 above). The construct may be used as a counterscreening reagent, in screens for modifiers of ceSREBP.

Example 5

TC1 Transposon Mutagenesis

The goal of this set of experiments was to produce loss-of-function mutations in genes of interest in order to understand the function of their wild-type counterparts.

Library Preparation

A Tc1 transposon insertion library comprising 3 sets of 960 cultures was constructed according to published protocols (Zwaal et al., supra, and Plasterk, supra). Very briefly, 35 5–10 non- synchronized mut-2(MT3126) animals were cultured on 100 mm peptone plates (2880 plates total) for 12 days. Each culture was then resuspended in M9 medium and aliquoted into 3 separate tubes, in identical positions, of 3 different racks (each rack holding 96 tubes). Two of the aliquots were frozen for long-term storage, and one lysed for DNA preparation. Lysates were pooled in a 3-dimensional matrix, and their DNA was purified. 10×to 50×dilutions of each DNA prep were used for library screenings by PCR.

Library Screening

The library was screened in individual tiers, each library having three tiers, with each tier composed of 1,000 lysates or ~200,000 haploid genomes. Lysates were pooled according to the published protocol. A first dimension screen involved PCR on 8 samples of pooled DNA from ten 96-well plates. A second dimension screen was used to determine which of the ten 96-well plates contained the desired mutant (involves screening of 10 DNA pools). A third dimension screen was used to determine the "address" of a particular mutant (i.e., in which column and row a particular mutant resided—via screening of 12 individual lysates from a single row). First dimension reactions were done in quadruplicate; second and third were done in triplicate.

Two rounds of PCR were performed the first with a pair of gene-specific primers and the second with a pair of Tc1-specific primers. Two different pairs of Te1 primers were used: one pair pointing outward from the left of the transposon, and the other pair pointing outward from the right (these primer pairs are described in the references cited above).

The first and second round PCR for each dimension was performed in 15 µl total volume using the following in each reaction:

1×PCR buffer provided by the manufacturer (Perkin-Elmer)
1.5 mM MgCl₂
0.2 mM dNTPs
0.5 FM each of the Te1 and the gene-specific primer
0.5 units of Taq Polymerase (Perkin-Elmer)
H₂O to 13 µl for the first round reactions, and to 15 µl for the second round First and Second dimension: 2 µl of 1:20 diluted DNA was added; 1:10 DNA diluted was added to the third dimension reactions. A small amount of first round reaction was transferred to the second round using a pin replicator. PCR cycling conditions were: 94° C. for 3 minutes; then 94 ° C. for 40 seconds, 58° C. for 1 minute, 72° C. for 2 35 cycles; then 72° C. for 2 minutes.

Insertion Screening

The primers used for Te1insertion analsysis were as follow:

Te1 Primers:

Tc1 L1 (round 1, left) CGTGGGTATTCCTTGTTC-GAAGCCAGCTAC (SEQ ID NO:21)

Tc1 L2(round 2, left) TCAAGTCAAATGGATGCT-TGAGA (SEQ ID NO:22)

Tc1 R1 (round 1, right) TCACAAGCTGATCGACTC-GATGCCACGTCG (SEQ ID NO:23)

Tc1 R2 (round 2, right) GATTTTGTGAACACTGTGGT-GAAGT (SEQ ID NO:24)

C. elegans SREBP genie-specific primers (each contained within SEQ ID NO:1):

Y47–1 (round 1) CCCACTCTGTCAAAATCTTCGG (SEQ ID NO:58)

Y47–2 (round 2) TCAGTGAATAGTGTTGCCGTGC (SEQ ID NO:59)

Y47–4 (round 1) AGCAATGGAACATATCAACGGG (SEQ ID NO:60)

Y47–3 (round 2) ACGACCAAGGTTTTCTTTTCCC (SEQ ID NO:61)

Y47–5 (round 1) TCATTGAGGTATGGTGTGGTGG (SEQ ID NO:62)

Y47–6 (round 2) GACCTCCACCCATTTTTGTGAG (SE ID NO:63)

Y47–8 (round 1) TGTTGTTTGTGCACAGCATGAG (SEQ ID NO:64)

Y47–7 (round 2) ACGAGCCCTCAGAACAAAACAG (SEQ ID NO:64)

Results:

Four confirmed Te1insertions were found in the ceSREBP gene: one insertion within intron 2 (found using Y47-5/6 and Te1R1/R2; address 1D10); one insertion within intron 5 (found using Y47-4/3 and Tc1 L1/L2; address 5D10); one insertion within intron 7 (found using Y47-1/2 and Te1 R1/R2; address 6D2); and one insertion within intron 8 (found using Y47-1/2 and Te1 L1/L2; address 1D2). All addresses are from Tier 1 of the Tc1 library described above.

Two of the insertion addresses were chosen for further analysis based on their relatively central location within the SREBP gene: 5D10, located just upstream of the predicted basic helix-loop-helix coding region, and 6D2, located downstream of the two predicted transmembrane domain coding regions.

Identification of Insertion Animals:

Nematodes from the 6D2 and 5D10 addresses were recovered from frozen stocks representing these addresses; these stocks were made from each culture upon preparation of the library. In order to identify a nematode carrying either a 6D2 or 5D10 insertion, individual surviving nematodes were cloned to individual plates, and after progeny from these nematodes were present on the plates, the parent nematodes were picked into individual wells of a 96-well plate containing 5 µl of nematode lysis buffer (100 mM KCl, 20 mM Tris-HCl pH 8.3, 5 mM MgCl₂, 0.9% Nonidet P-40, 0.9% Tween-20, 0.02% gelatin, and 400 µg/ml proteinase K). The nematodes were lysed in a PCR machine at 60° C. for one hour, followed by 95 ° C. for 15 minutes. 18 µl of a PCR master mix then was added to the crude lysates (to give ~20 µl total reaction volume, assuming evaporation of a portion of the lysate); this mix contained:

1×reaction buffer provided by the manufacturer (Perkin-Elmer)
1.5 mM MgCl₂
0.2 mM each dNTP
0.5 µM each gene-specific primer
0.5 units Taq polymerase to 18 µl per reaction with dH₂O The PCR reactions were cycled using a program identical to that used for screening the library for the insertions described above. Subsequently, a second round of PCR was performed using the same conditions and primers noted above for the insertion screen, after transferring a small amount of the first round reaction to the second round master mix using a pin replicator. Reactions were run on 1% agarose gels, and gels were analyzed for insertion products identical in size to those observed in the original screen for insertions.

Using this PCR-based screen, a population of nematodes was obtained that is homozygous for the 6D2 insertion. However, since the location of this Te1 insertion was confirmed to be within an intron, and Te1 elements are often completely removed along with the intron during splicing of the pre-mRNA, this insertion population was used to identify a deletion in the ceSREBP gene by imprecise excision of the Te1 element (as described above).

Identification of a Te1-mediated Deletion

In order to obtain a Te1-mediated deletion in the ceSREBP gene, a small library consisting of 244 cultures of 6D2 insertion nematodes was generated. To create the library, ~5–10 nematodes homozygous for the 6D2 insertion were seeded onto individual plates. After these nematodes had grown, reproduced, and consumed all of the bacteria on these plates, triplicate lysates representing these cultures were created by collecting a sample of nematodes from each plate by washing with a solution of distilled water, and placing the nematodes washed from each plate in one well of a 96-well plate (this was repeated two additional times to create a triplicate set of lysates). Nematodes were lysed by addition of an equal volume of lysis buffer (100 mM KCl, 20 mM Tris-HCl pH 8.3, 5 mM $MgCl_2$, 0.9% Nonidet P-40, 0.9% Tween-20, 0.02% gelatin, and 400 g/ml proteinase K) followed by incubation at −80° C. for 15 minutes, 60° C. for 3 hours, and 95° C. for 15–30 minutes Deletion screening was carried out using a PCR-based approach similar to that used for insertion screening, both of which have been described previously (Zwaal et al., supra; and Plasterk, supra). Two sets of gene-specific primer pairs were chosen for carrying out a nested PCR strategy such that an outside set was used for the first round of PCR and an inside set was used for the second round of PCR. The second round of PCR was performed to achieve greater specificity in the reaction. The primer sets listed below were chosen since they are ~3.2 kb apart in the ceSREBP genomic sequence (within the typical range for Tc1 deletion screening), and since they flank either side of the Te1 insertion in the 6D2 population.

Deletion Screening ceSREBP gene-specific primers used to identify candidate deletions in ceSREBP were: Y47-1 (round 1), Y47-2 (round 2), Y47-13 (round 1), and Y47-14 (round2). Primers used in a "specificity test", i.e. a secondary screen for confirming candidate deletions, were: Y47-1 (round 1), Y47-2 (round 2), Y47-4 (round 1), and Y47-3 (round 2). contained within SEQ ID NO:1:

Y47-1 CCCACTCTGTCAAATCTTCGG (SEQ ID NO:66 )

Y47-2 TCAGTGAATAGTGTTGCCGTGC (SEQ ID NO:67)

Y47-13 GCTTCTTCGGTTACTAGTTAAC (SEQ ID NO:68)

Y47-14 TCAGGAGCATGTTCAGCGACG (SEQ ID NO:69)

The first round PCR reactions were performed using 2 µl of lysate from two of the three sets of lysates, with reactions carried out in a 96-well plate. Each lysate was added to 18 µl of PCR reaction master mix aliquoted into each well:

1×reaction buffer provided by the manufacturer (Perkin-Elmer)

1.5 mM $MgC_2$ 0.2 m Meach dNTP 0.5 µM each gene-specific primer 0.5 units Taq polymerase to 18 ill per reaction with $dH_2O$ The reactions were carried out in duplicate using the following cycling parameters: 94° C. for 3 minutes, then 35 cycles of the following: 94° C. for 40 seconds, 55° C. for 1 minute, and 72° C. for 1 minute. The second round of PCR was performed essentially as above, except that 19.5 µl of the mixture as described for the first round reaction was aliquoted to each reaction. A small amount of first-round reaction products was transferred to the second-round reaction mixtures using a 96-pin replicator. The same temperature cycling sequence was used for the second round as described for the first round.

Products of the second round of PCR were analyzed by electrophoresis in 1% agarose gels. A potential deletion product was observed in both of the reactions, and the putative positive lysate was re-tested by performing duplicate reactions using the relevant lysate from all 3 sets of the library (for a total of six reactions) in two rounds of PCR as described above. The product was gel purified and sequenced directly to confirm the presence of the desired deletion. In addition, in order to confirm that the deletion product obtained was specific for the SREBP region (i.e. not an artifactual result of the PCR), an additional primer set was used in two rounds of PCR as above in a separate set of reactions with all three lysates along with one of the two original primer pairs. This primer set was chosen such that the PCR product generated would be ~100–300 base-pairs different in size from the original deletion product, resulting in a noticeable shift in size from the original product when analyzed on I% agarose gels. This part of the screening procedure is termed the "specificity test". Using this procedure to screen the 244 lysates from the 6D2 insertion library with the primers listed above, one deletion of ~2.2 kb within the ceSREBP genomic region was identified, and confirmed by the specificity test (primers used for this test are included in the table above) and by sequence analysis. This deletion begins within intron 6, and ends within exon 9 of the ceSREBP gene. After confirmation, this partial deletion allele was named pin-1 (ep79).

Identification of Deletion Animals

Following the identification and confirmation of this 2.2 kb deletion, 192 individual nematodes from the relevant plate were cloned onto separate, fresh plates. When F1 animals were present on the plate, the parent nematodes were placed into buffer present in 96-well plates and lysed as described above. The same primer pairs and cycling conditions used to identify the deletion were used to perform PCR on these animals. Of the 192 nematodes screened, one was found by PCR to carry the deletion.

Analysis of Mutant Phenotypes

Prior to analysis of the SREBP deletion animals, animals carrying the SREBP deletion were outcrossed ten times to a wild-type (N2/Bristol) strain in order to remove extraneous, unrelated mutations induced by the high number of Te1 elements present in the original, mutator strain from which the insertion and deletion in the ceSREBP gene were isolated. Throughout the outcrossing procedure, the SREBP deletion was followed and maintained by analyzing progeny of these crosses by PCR, using the same primers and conditions used for the deletion screen above.

Since reduction or elimination of function mutations often recapitulate phenotypes observed by RNA mediated interference, which in the case of ceSREBP included larval arrest, the deletion mutation was placed in trans to a balancer chromosome, and maintained as a heterozygous strain. This is based on the assumption that homozygous deletion mutants would not be able to be propagated themselves if the mutation results in a larval arrest phenotype.

The outcrossed and balanced strain was analyzed for any mutant phenotypes that might arise as a result of the SREBP deletion. It was found that 25% of the progeny derived from heterozygous SREBP deletion animals (which would correlate to presumptive deletion homozygotes) gave rise to phenotypes observed as the result of SREBP RNA-mediated interference described in Example 3 above. These phenotypes include: early larval arrest, reduced pigmentation as a result of reduced number of lipid droplets in the intestine, and accumulation of fluid-filled vesicles.

Example 6

Cloning of Drosophila S2P

Using BLAS, two EST clones from the Berkeley Drosophila Genome Project (BDGP), L) 11632 (AA391707) and LD 14421(AA439767) were found to have homology with hamster S2P (GI274573 1). The sequences were contained in two P1 clones D379 and D380 (AC005465). Primers were used for primer walking to get the full-1 length DNA sequence. Several more sequencing reactions were performed to produce a complete and unambiguous coverage of the gene which is referred to herein as Drosophila S2P (dS2P). The primer sequences below are contained within SEQ ID NO:3.

dS2P SEQUENCING PRIMERS:
(from primer walking)
507: GGTGAACAAGACAGCTCTTCG (SEQ ID NO:70)
852: AACGGTGGGAATCACTATGTCAG (SEQ ID NO:71)
1118: TGATGGTCAGCTACAGTGCTG (SEQ ID NO:72)
186: TTTCGTGAAGGTGAAATAGCAG (SEQ ID NO:73)
(to resolve ambiguities)
dS2P.s2: GGTCTTCAGCATAGGATTGG (SEQ ID NO:74)
dS2P.s3: CACAGTTCGAGTGACATCCC (SEQ ID NO:75)
dS2P.s4: GTGAGATGGCGCTGCTTTCG (SEQ ID NO:76)
dS2P.s5: GCACAAGGGTTGTGATGTAG (SEQ ID NO:77)
dS2P.s6: TACTCAGCCCGGTGTTCTTG (SEQ ID NO:78)

Results:

A full length clone (SEQ ID NO:3) was identified that contained a single open reading frame with an apparent translation start site at nucleotide position 219, and a stop signal at nucleotide position 1745. The predicted polypeptide precursor is 508 amino acids long (SEQ ID NO:4). A search of the PFam and PROSITE databases (Sonnhammer et al., Genomics (1997) 46:200–216; Bairoch et al. NAR (1991)19 Suppl:2241–2245; and Hofmann et al., NAR (1999) 27:215–219) revealed seven transmembrane domains and a PDZ domain. The transmembrane domains arc located at approximately amino acid residues 4 to 20 (TM1), 82–98 (TM2), 143–159 (TM3), 163–179 (TM4), 208–224 (TM5), 428–444 (TM6) and 478–494 (TM7). The putative PDZ domain is located at approximately amino acid residues 215–285.

The presence of other gene and protein sequences hearing significant homology to Drosophila S2P (SEQ ID NO:4) was investigated using the BLAST family of computer programs (Altschul et al., supra). The following amino acid sequences were the most similar: S2P *Homo sapiens* (GI2745733); S2P *Cricetulus griseus* (GI2745731); SP2 metalloprotease, *Homo sapiens* (GI4164134 and GI4164135); putative protein *Arabidopsis thaliana* (GI2982448); conserved protein *Methanobacterium* thermoautotrophicum (GI2622476); and Orf c04034 *Sulfolobus solfataricus* (GI1707806). The most homologous sequence was human S2P (GI2745733) which shared 9 contiguous amino acids at positions 201–207 of SEQ ID NO:4. Amino acid 127 to 501 of SEQ ID NO:4 shares 32% sequence identity with amino acids 148 to 515 of GI2745733.

Example 7

Cloning of Drosophila Scap

The Drosophila SCAP homologue (dSCAP) identified herein, was cloned by PCR based on sequence from a gene prediction and from 5' RACE. BLAST analysis of the hamster SCAP (GI1675220) revealed a genomic P1 clone, DS06954, with regions of high homology. GENSCAN genefinder analysis of this P1 predicted a cDNA that included these homologous regions and was partially covered by ESTs. dSCAP was cloned in overlapping N-terminal and C-terminal fragments with a common HindIII restriction enzyme site.

N-terminal sequence not represented within the gene prediction was obtained by RACE from embryo cDNA prepared with Marathon system (Clontech). A short N-terminal fragment was amplified using non-specific primer A P1 (CCATCCTAATACGACTCACTATAGGGC; SEQ ID NO:25) to the Marathon adator an antisense primer dSCAP6 (TCTGGTCCAGCTGCCCGT GTGTTC SEQ ID NO:79); contained within SEQ ID NO:5) contained within the gene prediction and the 5' EST. Amplification conditions were as follows:

---

1 μl Marathon cDNA
1 μl 10 mM dNTPs
5 μl Klentaq ™ buffer
2 μl AP1, 5 μM
2 μl dSCAP6, 5 μM
1 μl Klentaq ™ polymerase
38 μl H₂O
94° C. 2 min

| | |
|---|---|
| 5 cycles of: | 94° C. 15 sec |
| | 70° C. 4 min |
| 5 cycles of: | 94° C. 15 sec |
| | 68° C. 4 min |
| 25 cycles of: | 94° C. 15 sec |
| | 62° C. 30 sec |
| | 72° C. 3 min |

72° C. 4 min
12° C. hold
1 μl Amplitaq ™ added with an additional incubation for 10 min at 72° C.

---

The major PCR product as determined on a 1% agarose gel was an ~0.7 kb band. This fragment was cloned into the pCRII shuttle vector (Invitrogen) and completely sequenced using M13 forward and reverse primers, and the start codon was identified. Based on the N-terminal sequence identified, a longer N-terminal fragment was amplified from Marathon embryo cDNA using primers dSCA P11 (TTGGTATACGGATAGAAATTGG; SEQ ID NO:80) and dSCAP2 (GCGTTTGGGTATTCGTTGCTCC; SEQ ID NO:81). Conditions were as follows:

```
2 µl Marathon cDNA
5 µl 2 mM dNTPs
5 µl Expand High Fidelity 10x buffer with MgCl₂
3 µl dSCAP11, 5 µM
3 µl dSCAP2, 5 µM
0.75 µl Expand High Fidelity enzyme mix
31.25 µl H₂O
94° C. 3 min
35 cycles of:            94° C. 15 sec
                         50° C. 30 sec.
                         72° C. 4 min
72° C. 4 min
12° C. hold
    1 µl Amplitaq ™ added with an additional incubation
    for 10 min at 72° C.
```

The major PCR product as determined on a 1% agarose gel was an ~1.6 kb band. The C-terminal fragment was amplified from embryo 1$^{st}$ stand cDNA using sense primer dSCAP3 (CTCAGTCGCATCCAAAACTGTG; SEQ ID NO82) and ants,se primer dSCAP4 (TTA GGCGCGCCTAT-TCCTAGGTGCTAGCGAACC; SEQ ID NO:83) made to the predicted cDNA sequence. Amplifications conditions were as follows:

```
2 µl 1st strand cDNA
5 µl 2 mM dNTPs
5 µl Expand High Fidelity 10x buffer with MgCl₂
3 µl dSCAP3, 5 µM
3 µl dSCAP4, 5 µM
0.75 µl Expand High Fidelity enzyme mix
31.25 µl H₂O
94° C.  3 min
15 cycles of:            94° C. 15 sec
                         60° C. 30 sec
                         72° C. 2 min
20 cycles of:            94° C. 15 sec
                         60° C. 30 sec
                         72° C. 2 min +
                         20 sec/cycle
72° C. 5 min
 4° C. hold
    1 µl Amplitaq ™ added with an additional
    incubation for 10 min at 72° C.
```

The major PCR product as determined on a 1% agarose gel was an ~2.2 kb band. Both N-terminal and C-terminal fragments were cloned into PCRII and completely sequenced in both directions.

Results

A full-length clone was identified that contained a single open reading frame with an apparent translation al initiation site at nucleotide position 73 and a stop signal at nucleotide position 3786 (SEQ ID NO:5). The predicted polypeptide precursor is 1237 amino acids long (SEQ ID NO:6). Additional features include:

1) A Ribosomal RNA adenine dimethylase at nucleotides 667 to 703 (amino acid residues 198 to 210);
2) Four 6-beta (GB) repeat AID domains: GB1 at nucleotides 2509 to 2617, corresponding to amino acid residues 812 to 848; GB2 at nucleotides 3080 to 3196, corresponding to amino acid residues 1005 to 1041; GB3 at nucleotides 3208 to 3325, corresponding to amino acid residues 1045 to 1084; and GB4 at nucleotides 3337 to 3445, corresponding to amino acid residues 1088 to 1124;
3) Six predicted transmembrane (TM) domains. TM1 at nucleotides 991 to 1039, corresponding to amino acid residues 306 to 322; TM2 at nucleotides 1117 to 1165, corresponding to amino acid residues 348 to 364; TM3 at nucleotides 1180 to 1228, corresponding to amino acid residues 369–385; TM4 at nucleotides 1366 to 1414, corresponding to amino acid residues 431–447; TM5 at nucleotides 1753 to 1801, corresponding to amino acid residues 560 to 576; and TM6 at nucleotides 2353 to 2401, corresponding to amino acid residues 760 to 776.

The presence of other gene and protein sequences bearing significant homology to dSCAP (SEQ ID NO:5) was investigated using BLAST (Altschul et al., supra) against nucleotide databases. This revealed that dSCAP is covered by two genomic clones from BDGP: DS06954 (P1 D338), and DS05325 (P1 D340). The accession number for the two clones is AC007121. Other sequences bearing nucleotide homology with dSCAP are human mRNA for KIAA0199 gene (GI1228046), and Cricetulus griseus SCAP mRNA (GI 1228046). At the protein level, dSCAP shares homology with the following sequences: *C. elegans* predicted SCAP D2013.8 (GI642180), Homo sapiens KIAA0199 gene (GI 1228047), *Cricetulus griseus* SCAP (GI1675220), and is similar to the transmembrane domain of HMGCOA (GI3875380).

Example 8

Transgenic Drosophila Misexpressing Srebp

The wild-type Drosophila SREBP (dSREBP) (HLH106) gene was cloned by PCR. The coding sequence of the gene was amplified in overlapping N-terminal and C-terminal regions from a Drosophila adult cDNA library (Stratagene, cat #936603): Primers used to amplify the N-terminal region were sense prime HLH106.1 (AATGGA CACGACACT-GATGAAC; SEQ ID NO:84) and antisense primer HLH 106.2 (AGCCATGTTGCTTGCGAATAGT; SEQ ID NO:85) Primers used to amplify the C-terminal regions were sense primer HLH 106.3 (AAACAGGCGCTG GCATCT-GCAC; SEQ ID NO:86) and antisense primer HLH 106.4 (GGCGCCCCACGTTCGTGCCACTTATTATGTA; SEQ ID NO:87). The fragments were spliced together using the common restriction site SacII. In addition to the wild-type gene, one putative constitutively active form dSREBP (dSREBP.CA) and three putative dominant negative forms were engineered for misexpression in Drosophila. All were designed based on precedents in mammalian SREBP research (reviewed by Brown and Goldstein, supra). These constructs, as well as the wild-type gene may be used both as screening or counterscreening reagents, and as devices to further elucidate the function of SREBP in Drosophila.

Sequences of all fragments were verified. All constructs were cloned into pExPress-UAS. pExPress is a vector designed specifically for misexpression of genes in transgenic Drosophila. This vector was derived from pGMR (Hay et al., Development (1994) 120:2121–2129). The vector is 9Kb long, and contains: an origin of replication for *E. coli*; an ampicillin resistance gene; P element transposon 3' and 5' ends to mobilize the inserted sequences; a White marker gene; an expression unit comprising the TATA region of hsp70 enhancer and the 3' untranslated region of α-tubulin gene. The expression unit contains a first multiple cloning site (MCS) designed for insertion of an enhancer and a second MCS located 500 bases downstream, designed for the insertion of a gene of interest. DNA constructs are cloned into the EcoRI and/or EcoR1/AscI sites of the second MCS.

Fragments cloned into pExPress-UAS were injected into yw Drosophila embryos using standard protocols for Drosophila transformation (Rubin and Spradling, supra). A variety of GAL4 driver lines were used to drive mis-expression of the transgenes. Driver lines glass, sevenless, Kruppel, Rhomboid, 2677, and 1878 are available from the University of Indiana (http://flybase.bio.indiana.edu). Lines T93, T113, and T155 were kindly provided by Tian Xu (Yale University School of Medicine, New Haven, Conn., USA) Descriptions of the larval expression patterns of the GAL 4 are presented in Table III.

TABLE III

| GAL-4-Driver | Larval Expression Pattern |
|---|---|
| EYE | |
| 3× glass (GMR) | Photoreceptor cells, very strong expression |
| 2× sevenless | R7 photoreceptor cells |
| 2677 | Transiently, during eye development |
| FAT BODY | |
| T93 | Fat body, wing and eye discs, brain, salivary glands |
| T113 | Fat body, wing and eye discs, salivary glands |
| T155 | Fat body, wing and eye discs, brain, salivary glands |
| GUT/GENERAL | |
| 1878 | Ubiquitous (fat body, gut, discs, trachea, brain, etc.) |
| Kruppel | General gut, fat body, brain and segmental neurons, salivary glands |
| Rhomboid | Whole gut, segmental nerves, salivary glands, minor fat body and salivary gland staining |

The putative activated form, dSREBP.CA, contains amino acids 1–448 of dSREBP (SEQ ID NO:8) and lacks the C-terminal regulatory region, including the membrane-spanning domains, and thus should require no processing to activate transcriptional targets. dSREBP.CA was amplified by PCR from a clone of wild-type dSREBP using sense primer HLH 106.1 (AATGGACACGACACTGATGAAC; SEQ ID NO:88) and antisense primer HLH 106CA. (CTAGCGAGAGTGGGTGGCCATGC; SEQ ID NO:89) The observed phenotypes for this construct under various driver lines are presented in Table IV. The phenotypes exhibited by expression in the fat body is evidence that the dSREBP transgene exerts metabolic effects.

TABLE IV

| GAL4-Driver | Phenotype |
|---|---|
| Line #1 - No driver | Bristles (macrochaete) shortened, often missing |
| Line #2 - No driver | No phenotype |
| EYE | |
| 3× glass (GMR) | Line 1: Lethality, embryonic or larval |
| | Line 2: Strong rough eye |
| 2× sevenless | Lines 1 & 2: Lethality, early pupal |
| 2677 | Line 1: Lethality, embryonic or larval |
| | Line 2: Rough and reduced eye |
| FAT BODY | |
| T93 | Lines 1 & 2: Reduced male viability, reduced female fertility, adults with caved-in abdomens and starved appearance, persistence of the larval fat body in adults, short life spans (all w/variable penetrance) |

TABLE IV-continued

| GAL4-Driver | Phenotype |
|---|---|
| T113 | Line 1: Mostly pupal lethal, most survivors are female and have the abdomen phenotype of T93. |
| T155 | Lines 1 & 2: Larval lethal; a few escapers appear normal. |
| GUT/GENERAL | |
| 1878 | Lethal- embryo or larvae |
| Kruppel | Lethal- embryo or larvae |
| Rhomboid | Lethal- embryo or larvae |

Two putative dominant negative forms of dSREBP, "dSREBP.DNr (Dominant Negative regulated)" and "dSREBP.DNur (Dominant Negative unregulated)" lack the amino-terminal acidic domain and should be transcriptionally inactive. They are expected to act by competing with the wild-type protein in dimerization to make transcriptionally inactive dimers. They differ by the inclusion of the C-terminal regulatory region. dSREBP.DNr includes the fill regulatory region and should be active only in conditions in which dSREBP is cleaved from the ER membrane; it contains amino acids 75–1113 of dSREBP. dSREBP.DNr lacks the regulatory region and should not require processing; it may therefore be a more potent inhibitor of transcription. dSREBP.DNur contains amino acids 75–448 of dSREBP.

The 5' part of dSREBP.DNr was amplified by PCR from a clone containing the 5' of the dSREBPPugsing sense primer HLH106.DN (CGCAATGTCCGTCGAGCA ACAGCCGCAC; SEQ ID NO:90) and antisense primer HLH106.2 (AGCCATGTTGCTTGCGAATAGT; SEQ ID via NO:91). This fragment was spliced together with an overlapping clone containing the 3' part of dSREBP using the common restriction site SacII. dSREBPur was similarly amplified using sense primer HLH106.DN and antisense primer HLH106.CA.

The third putative dominant negative "p450/dSREBP" is expected to act through interaction with SCAP. p450/dSREBP contains the C-terminal regulatory region of dSREBP (amino acids 521–1113), fused to the mammalian cytochrome p450 transmembrane domain, which acts to anchor the protein in the ER. The p450 transmembrane, with a 5', in-frame ATG, was generated by annealing two complementary oligonucleotides. Sense-strand oligonucleotide was p450.1 (CTGGAATTCAACATGGATCCAGTGGTGG TGCTGGGACTCTGCCTCTCCTGCTTGCTTCTCCTTT CACTCTGGAAGCAGAGCTATGGAGGAG- GAAAGCTT; SEQ ID NO:26). Antisense-strand oligo was p450.2 (AAGCTTTCCTCCTCCATAGCTCTGCTTCCA GAGTGAAAGGAGAAGCAAGCAGGAGAG- GCAGAGT CCCAGCACCACCACTGGATCCATGT- TGAATTCCAGAGCT; SEQ ID NO:27). This transgene should act by titrating out dSCAP, leaving less available for the processing of wild-type dSREBP. Table V summarizes the observed phenotypes for the dominant negative constructs under various driver lines.

TABLE V

| Line | GAL4-Driver | Phenotype |
|---|---|---|
| | EYE | |
| Wild Type | 3x glass (GMR) | Rough eye; disorganization of ommatidia |
| | 2x sevenless | Some very mild roughness in posterior eye |
| | 2677 | Some very mild roughness in posterior eye |
| | EYE | |
| dSREBP.DNr | 3x glass (GMR) | Mild rough eye; disorganization of ommatidia |
| | 2x sevenless | No phenotype |
| | 2677 | Some very mild roughness in posterior eye |
| dSREBP.DNur | 3x glass (GMR) | Strong rough eye |
| | 2x sevenless | No phenotype |
| | 2677 | Some very mild roughness in posterior eye |

TABLE V-continued

| Line | GAL4-Driver | Phenotype |
|---|---|---|
| | GUT/GENERAL | |
| p450/dSREBP | Kruppel | Lethality, embryonic or larval |
| | EYE | |
| | 3x glass (GMR) | Strong rough eye, fused ommatidia |

The present invention is not to be limited in scope by the specific embodiments described herein. Indeed, various modifications of the invention in addition to those described herein will become apparent to those skilled in the art from the foregoing description and accompanying drawings. Such modifications are intended to fall within the scope of the appended claims. The disclosure of each reference cited herein, including patents and other references, is hereby incorporated herein by reference in its entirety.

What is claimed is:

1. A *C. elegans* that has been genetically engineering to mis-express an SREBP pathway protein comprising an amino acid sequence selected from the group consisting of SEQ ID NO:2 (SREBP), SEQ ID NO:94 (SCAP), and SEQ ID NO:95 (S2P), or the progeny of said *C. elegans* that has inherited said mis-expression, wherein said mis-expression results in a loss-of-function intestinal defect phenotype.

2. The *C. elegans* of claim 1 that has been genetically engineered by a method selected from the group consisting of transposon insertion mutagenesis, double-stranded RNA interference, and chemical mutagenesis.

3. A method for identifying a gene that modifies the function of a gene encoding an SREBP pathway protein comprising obtaining a first *C. elegans* defined by claim 1 and a second *C. elegans* that has the same genetic engineering as the first *C. elegans* and that additionally has a mutation in a gene of interest, and detecting a difference between the intestinal defect phenotype of the first *C. elegants* and the intestinal defect phenotype of the second *C. elegans*, wherein a difference in the phenotypes identifies the gene of interest as capable of modifying the function of the gene encoding said SREBP pathway protein.

4. The method of claim 3 wherein said gene of interest is implicated in cholesterol or fatty acid biosynthesis or metabolisms.

5. The method of claim 3 wherein said detecting step comprises staining the first and second *C. elegans* in vivo with a fluorescently-labelled fatty acid conjugate to measure lipid content within said first and second *C. elegans*.

6. The method of claim 5 wherein said fluorescently-labelled fatty acid conjugate comprises a fatty acid selected from the group consisting of 4,4 difluoro-5,7-dimethyl-4-bora-31,41-diaza-s-indacene-3-dodecanoic acid, and 4,4-difluoro-5-methyl-4-bora-3a,4a diaza-s-indacene-3-dodecanoic acid.

7. A method for studying lipid metabolism comprising administering one or more compound to a *C. elegans* defined by claim 1, and observing any changes in lipid content of said *C. elegans*.

8. The *C. elegans* of claim 1 wherein the SREBP pathway protein is SREBP (SEQ ID NO:2).

9. The *C. elegans* of claim 1 wherein the SREBP pathway protein is SCAP (SEQ ID NO:94).

10. The *C. elegans* of claim 1 wherein the SREBP pathway protein is S2P (SEQ ID NO:95).

11. An isolated nucleic acid molecule of less than 15 kb comprising a nucleic acid sequence that and (b) encodes an functionally SREBP identiry with amino acids comprising the amino acid sequence of SEQ ID NO:2.

12. The insolated nucleic acid molecule of claim 11 that comprise SEQ ID NO:1.

13. A vector comprising the nucleic acid molecule of claim 11.

14. A insolated host cell comprising the vector of claim 13.

15. The host cell of claim 14 wherein said cell is a yeast cell.

16. A process for producing an SREBP pathway protein comprising culturing the host cell of claim 14 under conditions suitable for expression of said SREBP pathway protein and recovering said protein.

* * * * *

SEQUENCE LISTING

<160> NUMBER OF SEQ ID NOS: 95

<210> SEQ ID NO 1
<211> LENGTH: 3419
<212> TYPE: DNA
<213> ORGANISM: Caenorhabditis elegans

<400> SEQUENCE: 1

```
ggtttaatta cccaagtttg agaatgaacg aagaattcga gggagacgtc cctatgtcgg      60
atccgttcct ctcattggtc acaaaattgg atgatattgc gccatttcca aataacgacc     120
cgctcgattt tgacatggag cacaactggc aagagcccgg accatcacaa caaccggatc     180
catcaattcc cggaaatcaa cacagtccgc cacaggaata ttatgatatt gatggtcaac     240
gagacgtaag caccttacac tccctgctca accacaacaa cgacgacttc ttctcaatgc     300
gattttcccc gccaaacttt gatctcggcg gaggccgtgg accttctcta gccgccaccc     360
aacaattatc tggagaaggt cctgcaagta tgcttaaccc cttacaaaca tctccaccaa     420
gtggaggtta ccccccggca gatgcctaca gacctctatc acttgctcaa caactcgccg     480
cgccagcgat gactccacat caggcagcgt cgcttttttgt taatactaat ggaattgatc     540
aaaagaattt cactcatgca atgctatctt caccacacca tacctcaatg acttctcaac     600
catatacaga agccatggga catatcaacg ggtacatgtc tccatacgac caagctcaag     660
gcccatcagg accatcatat tactcacaac accatcaatc tccaccacct catcaccacc     720
atcaccaccc gatgccaaaa atccatgaga accctgaaca agtggcatct ccatcgattg     780
aagatgctcc agagacgaaa ccaactcatt tggttgaacc acaaagtcca aaaagcccgc     840
agaatatgaa agaggagctt cttcggttac tagttaacat gtctccgagt gaagttgaac     900
ggttaaagaa taaaaaatca ggagcatgtt cagcgacgaa tgggccatcg aggagtaagg     960
agaaggcggc gaagattgtg attcaggaga cagcggaagg ggatgaagat gaggatgatg    1020
aggatagtga ttccggggag actatgtctc agggaactac tattattgtt cgaagaccaa    1080
aaaccgagcg tcgtacggca cacaatctca tcgaaaagaa gtatagatgc tcaataaatg    1140
atcgaattca acagctgaaa gtacttttgt gtggggatga agctaagctt tcaaaatcgg    1200
```

```
caacactacg acgggctatt gaacatatcg aggaggttga acacgagaat caggtgttga    1260
agcatcatgt tgaacaaatg agaaagacac tgcagaataa tcgattaccg tacccggaac    1320
caattcaata cactgaatac tctgcccgat cacccgtcga atcatctcct tctccaccta    1380
gaaatgagag aaaacgatca cgaatgagca aacgactcc tatgaagaat ggaactagag    1440
atggatcttc gaaagttacc cttttttgcga tgctcctagc agttctgatt tttaatccga    1500
ttggattgct cgctggaagt gcgatattct caaaagccgc tgcagaagct ccgattgcct    1560
ccccgttcga gcatggaaga gtgattgatg acccggatgg aactagcact cggacgcttt    1620
tctgggaagg gagtatcatc aatatgagct atgtctgggt gttcaacatc ttaatgatca    1680
tatatgtggt tgtcaaactg ctgatccatg gtgaccctgt tcaagacttc atgtccgttt    1740
catggcagac ttttgtgacg actcgagaga aggcgagagc cgagttgaac tctggaaatt    1800
tgaaagatgc tcagagaaag ttctgcgagt gtcttgcaac gttggatcga tcgcttccat    1860
caccggggt tgattcggtg ttttcggttg gctgggaatg cgttcgacat cttttgaatt    1920
ggttgtggat cgggagatac atcgcaagaa ggcgcaggtc caccacgaag cctgtctcag    1980
tcgtttgtag gagtcatgcg cagactgcag ttctctatca tgaaattcat cagctccatc    2040
taatgggtat cactgaaaac ttcgaagaca cctatgaacc atccgcccta acgggcctct    2100
tcatgtccct ctgtgcagta aaccttgctg aagctgccgg agcatcaaac gacggacttc    2160
cacgcgccgt catggctcag atctacattt ctgcatccat ccaatgccgt ttggctcttc    2220
cgaacctact cgcaccattc ttctcgggat acttttacg aagagctcga aggcacgtgc    2280
gtcgagctcc ggagcactcg gtgtcccatt tgttatggat cttccatcca gcgacaagaa    2340
agttcatgtc agatgcgaaa aggttggagc atgtgttgag ctcgaagcag aagcagttga    2400
gatttgggtc ttttgtggaa gatgagcaat tatccccact tgctcgaatc cgaacaacgc    2460
tgaaagtgta cctactctcc aaacttgtac aggaacttgt cggtggtgac gagatctta    2520
caaaaaatgt ggaacgcatc ctaaatgaca atgaccgtct cgatgatgaa gtagacgtgg    2580
ttgatgtttc aagacttttg gtgacaattt caacgcagtg cgctgccatt ttgactaatg    2640
agaaggatga gtcagcgaaa ttcggaacct ggatctctcg aaacggagat gcttgttgca    2700
catggtggac gcacgttctg acatgtggaa tctattggag gagtaacaag aatgagctgg    2760
cacggcaaca ctattcactg atcaggaact gtccgccgaa gattttgaca gacaatctgg    2820
gtttggcggt tggccacgcg ttgtgtgctc gcaagatttg catagatgac cgagattccc    2880
cgaaagtcag tcaatacgtg tgcattcaca caaagaagtc gctcgaatcc ctccgactat    2940
tctccacatc atcgcgagca tcaggtgtgg tgtctggaat tcaggaaggt acacgccgaa    3000
tggcctacga atggattatg aactcgctgc tcgacgcgtg gcgttccaat ctattcgcat    3060
cgaaacccta ctggacacaa agcttcaagg gacaatccac gtttagtacg ctttatcaag    3120
aggcgtataa tcattatgcg attattaatg ggacaagggg agattgttgg agactatttg    3180
tctacgagct cacgtgccga atgctcaacg gagccaaccc acaagccacg tggtcaggcg    3240
yccgacgcgt tcgatctaca aaaatggacg cggtccgagg aagagtgagc atgcgacgct    3300
cggctcaacc ggacgcattt catcttcata cactggttaa actacatact tctatggatc    3360
tttgaattga acaaaaaatg attttattca gaataatgat aaatacgatt atatataaa    3419
```

<210> SEQ ID NO 2
<211> LENGTH: 1113
<212> TYPE: PRT

-continued

```
<213> ORGANISM: Caenorhabditis elegans
<220> FEATURE:
<221> NAME/KEY: misc_feature
<222> LOCATION: (1073)..(1073)
<223> OTHER INFORMATION: "Xaa" is any amino acid

<400> SEQUENCE: 2
```

```
Met Asn Glu Glu Phe Glu Gly Asp Val Pro Met Ser Asp Pro Phe Leu
1               5                   10                  15

Ser Leu Val Thr Lys Leu Asp Asp Ile Ala Pro Phe Pro Asn Asn Asp
            20                  25                  30

Pro Leu Asp Phe Asp Met Glu His Asn Trp Gln Glu Pro Gly Pro Ser
        35                  40                  45

Gln Gln Pro Asp Pro Ser Ile Pro Gly Asn Gln His Ser Pro Pro Gln
50                  55                  60

Glu Tyr Tyr Asp Ile Asp Gly Gln Arg Asp Val Ser Thr Leu His Ser
65                  70                  75                  80

Leu Leu Asn His Asn Asn Asp Asp Phe Phe Ser Met Arg Phe Ser Pro
                85                  90                  95

Pro Asn Phe Asp Leu Gly Gly Gly Arg Gly Pro Ser Leu Ala Ala Thr
            100                 105                 110

Gln Gln Leu Ser Gly Glu Gly Pro Ala Ser Met Leu Asn Pro Leu Gln
        115                 120                 125

Thr Ser Pro Pro Ser Gly Gly Tyr Pro Pro Ala Asp Ala Tyr Arg Pro
130                 135                 140

Leu Ser Leu Ala Gln Gln Leu Ala Ala Pro Ala Met Thr Pro His Gln
145                 150                 155                 160

Ala Ala Ser Leu Phe Val Asn Thr Asn Gly Ile Asp Gln Lys Asn Phe
                165                 170                 175

Thr His Ala Met Leu Ser Ser Pro His His Thr Ser Met Thr Ser Gln
            180                 185                 190

Pro Tyr Thr Glu Ala Met Gly His Ile Asn Gly Tyr Met Ser Pro Tyr
        195                 200                 205

Asp Gln Ala Gln Gly Pro Ser Gly Pro Ser Tyr Tyr Ser Gln His His
210                 215                 220

Gln Ser Pro Pro Pro His His His His His Pro Met Pro Lys Ile
225                 230                 235                 240

His Glu Asn Pro Glu Gln Val Ala Ser Pro Ser Ile Glu Asp Ala Pro
                245                 250                 255

Glu Thr Lys Pro Thr His Leu Val Glu Pro Gln Ser Pro Lys Ser Pro
            260                 265                 270

Gln Asn Met Lys Glu Glu Leu Leu Arg Leu Leu Val Asn Met Ser Pro
        275                 280                 285

Ser Glu Val Glu Arg Leu Lys Asn Lys Lys Ser Gly Ala Cys Ser Ala
290                 295                 300

Thr Asn Gly Pro Ser Arg Ser Lys Glu Lys Ala Ala Lys Ile Val Ile
305                 310                 315                 320

Gln Glu Thr Ala Glu Gly Asp Glu Asp Glu Asp Glu Asp Ser Asp
                325                 330                 335

Ser Gly Glu Thr Met Ser Gln Gly Thr Thr Ile Ile Val Arg Arg Pro
            340                 345                 350

Lys Thr Glu Arg Arg Thr Ala His Asn Leu Ile Glu Lys Lys Tyr Arg
        355                 360                 365

Cys Ser Ile Asn Asp Arg Ile Gln Gln Leu Lys Val Leu Leu Cys Gly
370                 375                 380
```

-continued

```
Asp Glu Ala Lys Leu Ser Lys Ser Ala Thr Leu Arg Arg Ala Ile Glu
385                 390                 395                 400

His Ile Glu Glu Val Glu His Glu Asn Gln Val Leu Lys His His Val
            405                 410                 415

Glu Gln Met Arg Lys Thr Leu Gln Asn Asn Arg Leu Pro Tyr Pro Glu
            420                 425                 430

Pro Ile Gln Tyr Thr Glu Tyr Ser Ala Arg Ser Pro Val Glu Ser Ser
        435                 440                 445

Pro Ser Pro Pro Arg Asn Glu Arg Lys Arg Ser Arg Met Ser Thr Thr
    450                 455                 460

Thr Pro Met Lys Asn Gly Thr Arg Asp Gly Ser Ser Lys Val Thr Leu
465                 470                 475                 480

Phe Ala Met Leu Leu Ala Val Leu Ile Phe Asn Pro Ile Gly Leu Leu
                485                 490                 495

Ala Gly Ser Ala Ile Phe Ser Lys Ala Ala Glu Ala Pro Ile Ala
            500                 505                 510

Ser Pro Phe Glu His Gly Arg Val Ile Asp Asp Pro Asp Gly Thr Ser
        515                 520                 525

Thr Arg Thr Leu Phe Trp Glu Gly Ser Ile Ile Asn Met Ser Tyr Val
    530                 535                 540

Trp Val Phe Asn Ile Leu Met Ile Ile Tyr Val Val Lys Leu Leu
545                 550                 555                 560

Ile His Gly Asp Pro Val Gln Asp Phe Met Ser Val Ser Trp Gln Thr
                565                 570                 575

Phe Val Thr Thr Arg Glu Lys Ala Arg Ala Glu Leu Asn Ser Gly Asn
            580                 585                 590

Leu Lys Asp Ala Gln Arg Lys Phe Cys Glu Cys Leu Ala Thr Leu Asp
        595                 600                 605

Arg Ser Leu Pro Ser Pro Gly Val Asp Ser Val Phe Ser Val Gly Trp
    610                 615                 620

Glu Cys Val Arg His Leu Leu Asn Trp Leu Trp Ile Gly Arg Tyr Ile
625                 630                 635                 640

Ala Arg Arg Arg Arg Ser Thr Thr Lys Pro Val Ser Val Val Cys Arg
                645                 650                 655

Ser His Ala Gln Thr Ala Val Leu Tyr His Glu Ile His Gln Leu His
            660                 665                 670

Leu Met Gly Ile Thr Gly Asn Phe Glu Asp Thr Tyr Glu Pro Ser Ala
        675                 680                 685

Leu Thr Gly Leu Phe Met Ser Leu Cys Ala Val Asn Leu Ala Glu Ala
    690                 695                 700

Ala Gly Ala Ser Asn Asp Gly Leu Pro Arg Ala Val Met Ala Gln Ile
705                 710                 715                 720

Tyr Ile Ser Ala Ser Ile Gln Cys Arg Leu Ala Leu Pro Asn Leu Leu
                725                 730                 735

Ala Pro Phe Phe Ser Gly Tyr Phe Leu Arg Arg Ala Arg Arg His Val
            740                 745                 750

Arg Arg Ala Pro Glu His Ser Val Ser His Leu Leu Trp Ile Phe His
        755                 760                 765

Pro Ala Thr Arg Lys Phe Met Ser Asp Ala Lys Arg Leu Glu His Val
    770                 775                 780

Leu Ser Ser Lys Gln Lys Gln Leu Arg Phe Gly Ser Phe Val Glu Asp
785                 790                 795                 800
```

```
Glu Gln Leu Ser Pro Leu Ala Arg Ile Arg Thr Thr Leu Lys Val Tyr
            805                 810                 815
Leu Leu Ser Lys Leu Val Gln Glu Leu Val Gly Gly Asp Glu Ile Phe
            820                 825                 830
Thr Lys Asn Val Glu Arg Ile Leu Asn Asp Asn Asp Arg Leu Asp Asp
            835                 840                 845
Glu Val Asp Val Val Asp Val Ser Arg Leu Leu Val Thr Ile Ser Thr
        850                 855                 860
Gln Cys Ala Ala Ile Leu Thr Asn Glu Lys Asp Glu Ser Ala Lys Phe
865                 870                 875                 880
Gly Thr Trp Ile Ser Arg Asn Gly Asp Ala Cys Cys Thr Trp Trp Thr
                885                 890                 895
His Val Leu Thr Cys Gly Ile Tyr Trp Arg Ser Asn Lys Asn Glu Leu
                900                 905                 910
Ala Arg Gln His Tyr Ser Leu Ile Arg Asn Cys Pro Pro Lys Ile Leu
            915                 920                 925
Thr Asp Asn Leu Gly Leu Ala Val Gly His Ala Leu Cys Ala Arg Lys
        930                 935                 940
Ile Cys Ile Asp Asp Arg Asp Ser Pro Lys Val Ser Gln Tyr Val Cys
945                 950                 955                 960
Ile His Thr Lys Ser Leu Glu Ser Leu Arg Leu Phe Ser Thr Ser
                965                 970                 975
Ser Arg Ala Ser Gly Val Val Ser Gly Ile Gln Glu Gly Thr Arg Arg
            980                 985                 990
Met Ala Tyr Glu Trp Ile Met Asn  Ser Leu Leu Asp Ala  Trp Arg Ser
        995                 1000                1005
Asn Leu Phe Ala Ser Lys Pro Tyr Trp Thr Gln Ser  Phe Lys Gly
    1010                1015                1020
Gln Ser Thr Phe Ser Thr Leu Tyr Gln Glu Ala Tyr  Asn His Tyr
    1025                1030                1035
Ala Ile Ile Asn Gly Thr Arg  Gly Asp Cys Trp Arg  Leu Phe Val
    1040                1045                1050
Tyr Glu Leu Thr Cys Arg Met  Leu Asn Gly Ala Asn  Pro Gln Ala
    1055                1060                1065
Thr Trp Ser Gly Xaa Arg Arg  Val Arg Ser Thr Lys  Met Asp Ala
    1070                1075                1080
Val Arg Gly Arg Val Ser Met  Arg Arg Ser Ala Gln  Pro Asp Ala
    1085                1090                1095
Phe His Leu His Thr Leu Val  Lys Leu His Thr Ser  Met Asp Leu
    1100                1105                1110

<210> SEQ ID NO 3
<211> LENGTH: 1971
<212> TYPE: DNA
<213> ORGANISM: Drosophila melanogaster

<400> SEQUENCE: 3
cggcacgagg attaatgctg atttctggtc tggactacac agcattgctg gtataaggag      60
tcgggaccag aggagtaaga tttcgggaag gaatcccgtc cggtagggac tactagcatt     120
cgcaagtgac gtccagcaac cggaggaccc ccaactgtag aatccgcatc accatcctaa     180
tcccaacaaa ccaatgacat cttgagacct caccagccat ggatcccttc gtgttcttca     240
tagtactggc atcgctttat ggcgttcttt acttttcga ccgcttcttc aagagttgca     300
tgcactaccc gtacgatgcc ttcctcaaga acaccgggct gagtataaat ttcatgagcc     360
```

-continued

```
tccactggca cacgagtgcc tttaacagga ccctcctacg ctggggatct gccggtaaca    420
gctgcacccg gagagtaatg atcaccagct ttaatgtagg agtcctggtc accttttctc    480
tgctcccgat cggtctgatc ctgctcattg ccactatctt cagcagtggt gaacaagaca    540
gctcttcgtc tgtatcctcg cccgttggag tccctgtgca gctggaaatt ctactgcccg    600
gcgtcaactt gccgttggag gagatcggat actacatcac aaccettgtg ctctgcttgg    660
tggtgcacga gatgggacac gccctggccg ctgtgatgga ggatgtgcct gtcaccgggt    720
ttggaataaa gttcatcttc tgcctgccgt tagcatacac ggagctctcc cacgaccact    780
taaacagtct acgttggttc cgcaagctac gtgttctgtg cgctggaatc tggcataatt    840
ttgtgttcgc tggcgtgtgc tatctcttaa tctcaacggt gggaatcact atgtcaccttt    900
tgtacgctta caaccaacac gtagtggtca ctgaactaac aaggaaatcc ccgctgaggg    960
gagagcgcgg cttgcaagtg gacaatcaaa taacccaagt aaacggctgc cagtaaaaca   1020
gcgaggagag ttgggtgaca tgcctgcaga actctctgaa gctcaagccg ggctactgtg   1080
tgagtgcgga cttcgtgcag cttaacgacg aaagcagcgc catctcacat catagcattg   1140
atggtcagct acagtgctgt gatgaactaa atccgaacgt aagctgcttc gaggtggtgg   1200
aggacgcaaa tggagatgtg ccggtggagc tgccgcagca tgtatgtctc aatgtgcgcc   1260
gcactttgga ggaggtctcc gagcactgct cgtccggagt ttgcaacgag ggattctgcc   1320
tacgaccgct tatacgaaat atcactgcca taatgacgtt caagcgacag aattttcgcg   1380
gagagaagct gccgccggtg atctatgtgg gccatccatg ggatgtcact cgaactgtgg   1440
aggtatccgc ctttgtgccg agatatagct tattaaaggc agcctggccg gatgcctggc   1500
tgctgctcct caagtataac gtggtcttca gcataggatt ggcgttgatc aatgccattc   1560
cctgctttgg tttcgatggc gcccacatta ccagcaccgt gatacacagc ttcttggtgg   1620
gcagagtgga tcagcatgcc aagagagata tcatctcgtt gataatcacc agcgtgggtt   1680
cccttctctt tgcactggcc ctgcttaagg tggcctggtt gagttttctg cgaccctgc   1740
tttaagaact gaaatggaaa actgaaatgg atcctgggag ttcaactccc tgcaaagacg   1800
ctagactgct atttcacctt cacgaaacac acaaaaacac agcgaattgt agcacctcaa   1860
agattcgata gcttttttgtc atagtcctta gtcttaactc gtatttattt tcgtacggtt   1920
gtcgagctca aaaataaaat caaattaagc taaaaaaaaa aaaaaaaaa c              1971
```

<210> SEQ ID NO 4
<211> LENGTH: 508
<212> TYPE: PRT
<213> ORGANISM: Drosophila melanogaster

<400> SEQUENCE: 4

```
Met Asp Pro Phe Val Phe Phe Ile Val Leu Ala Ser Leu Tyr Gly Val
1               5                   10                  15

Leu Tyr Phe Phe Asp Arg Phe Phe Lys Ser Cys Met His Tyr Pro Tyr
                20                  25                  30

Asp Ala Phe Leu Lys Asn Thr Gly Leu Ser Ile Asn Phe Met Ser Leu
            35                  40                  45

His Trp His Thr Ser Ala Phe Asn Arg Thr Leu Arg Trp Gly Ser
        50                  55                  60

Ala Gly Asn Ser Cys Thr Arg Arg Val Met Ile Thr Ser Phe Asn Val
65                  70                  75                  80

Gly Val Leu Val Thr Phe Ser Leu Leu Pro Ile Gly Leu Ile Leu Leu
```

```
                85                  90                  95
Ile Ala Thr Ile Phe Ser Ser Gly Glu Gln Asp Ser Ser Ser Val
            100                 105                 110

Ser Ser Pro Val Gly Val Pro Val Gln Leu Glu Ile Leu Leu Pro Gly
            115                 120                 125

Val Asn Leu Pro Leu Glu Glu Ile Gly Tyr Tyr Ile Thr Thr Leu Val
            130                 135                 140

Leu Cys Leu Val Val His Glu Met Gly His Ala Leu Ala Ala Val Met
145                 150                 155                 160

Glu Asp Val Pro Val Thr Gly Phe Gly Ile Lys Phe Ile Phe Cys Leu
                165                 170                 175

Pro Leu Ala Tyr Thr Glu Leu Ser His Asp His Leu Asn Ser Leu Arg
            180                 185                 190

Trp Phe Arg Lys Leu Arg Val Leu Cys Ala Gly Ile Trp His Asn Phe
        195                 200                 205

Val Phe Ala Gly Val Cys Tyr Leu Leu Ile Ser Thr Val Gly Ile Thr
        210                 215                 220

Met Ser Pro Leu Tyr Ala Tyr Asn Gln His Val Val Val Thr Glu Leu
225                 230                 235                 240

Thr Arg Lys Ser Pro Leu Arg Gly Glu Arg Gly Leu Gln Val Asp Asn
                245                 250                 255

Gln Ile Thr Gln Val Asn Gly Cys Pro Val Asn Ser Glu Glu Ser Trp
            260                 265                 270

Val Thr Cys Leu Gln Asn Ser Leu Lys Leu Pro Gly Tyr Cys Val
        275                 280                 285

Ser Ala Asp Phe Val Gln Leu Asn Asp Glu Ser Ser Ala Ile Ser His
        290                 295                 300

His Ser Ile Asp Gly Gln Leu Gln Cys Cys Asp Glu Leu Asn Pro Asn
305                 310                 315                 320

Val Ser Cys Phe Glu Val Val Glu Asp Ala Asn Gly Asp Val Pro Val
                325                 330                 335

Glu Leu Pro Gln His Val Cys Leu Asn Val Arg Arg Thr Leu Glu Glu
            340                 345                 350

Val Ser Glu His Cys Ser Ser Gly Val Cys Asn Glu Gly Phe Cys Leu
        355                 360                 365

Arg Pro Leu Ile Arg Asn Ile Thr Ala Ile Met Thr Phe Lys Arg Gln
        370                 375                 380

Asn Phe Arg Gly Glu Lys Leu Pro Pro Val Ile Tyr Val Gly His Pro
385                 390                 395                 400

Trp Asp Val Thr Arg Thr Val Glu Val Ser Ala Phe Val Pro Arg Tyr
                405                 410                 415

Ser Leu Leu Lys Ala Ala Trp Pro Asp Ala Trp Leu Leu Leu Lys
            420                 425                 430

Tyr Asn Val Val Phe Ser Ile Gly Leu Ala Leu Ile Asn Ala Ile Pro
        435                 440                 445

Cys Phe Gly Phe Asp Gly Ala His Ile Thr Ser Thr Val Ile His Ser
450                 455                 460

Phe Leu Val Gly Arg Val Asp Gln His Ala Lys Arg Asp Ile Ile Ser
465                 470                 475                 480

Leu Ile Ile Thr Ser Val Gly Ser Leu Leu Phe Ala Leu Ala Leu Leu
            485                 490                 495

Lys Val Ala Trp Leu Ser Phe Leu Arg Pro Leu Leu
            500                 505
```

<210> SEQ ID NO 5
<211> LENGTH: 4128
<212> TYPE: DNA
<213> ORGANISM: Drosophila melanogaster

<400> SEQUENCE: 5

| | | | | | |
|---|---|---|---|---|---:|
| gtgtgcctga | ctgttttgta | ggtgtaagga | ggggcgtggc | caaatagttt | ttggtatacg | 60 |
| gatagaattt | ggatgaaaaa | taaaacgaaa | tcaaaacatt | tttcaaaagc | gtggaagttt | 120 |
| tggccggctt | gtgggcatgg | caaaacgttt | tttggctatc | cgttaatcaa | cataccgttg | 180 |
| cccgggacaa | tacccaccaa | gatcgttgta | ccctacgaaa | ctggatccgg | atcgctgtca | 240 |
| tggcactctc | ttaatacatc | ctcgactaca | ccgcaggaac | cgcacccttc | cggcgaaccc | 300 |
| tggcccccg | aaccacaggt | actcaatagc | agtaccacgg | accgcagccc | gcctcccctt | 360 |
| ctgccctggg | cgcagagcag | ccccgccttt | ttctacgtcc | agcagattac | tctgcgaacc | 420 |
| agtgttctcc | cgtggacgga | gggaatgcag | cttatggatg | cgtttcgtgc | gccgctacac | 480 |
| gaagttttta | aattgcttga | aattgtgcgc | aatcaccaga | gcagcgaaaa | caaacgtacc | 540 |
| ctggagcaca | actgcctaca | tgtagacaac | gtaaagcgcg | gaacacacgg | gcagctggac | 600 |
| cagatctttc | cggagtatgg | ctgcctgctg | ctctcgcccg | ccaacctgtg | gacgcagaac | 660 |
| tctcagaact | ttactcggga | cacaaacatc | ctgaacacga | tatttcagta | ccataaccta | 720 |
| cagaaatcaa | aagtttccgc | ggcgaaaatg | ctgtttggat | tacccatgca | ggacactgga | 780 |
| ttcaagcgct | atccattgcg | cgctcggtcg | cgtattatac | agtatgcctt | gacgttattc | 840 |
| ctcaagcaca | acgatatgga | gtatctggac | actctaaagg | aaaagctgct | gcgacactat | 900 |
| cccccactcc | cgttggctag | tgcgtcggct | gaagagccga | cgaccataac | ttacatcttt | 960 |
| tatccaggag | agtacaggat | gtgggagctg | gtgccttaca | cagtggcctt | tatgttggtg | 1020 |
| tttgcttatg | tgtacttctc | tgttcgaaaa | atcgatgtat | ttcgttcccg | cttttttgctg | 1080 |
| gccttatgta | gcgtaatcac | cacagccggg | agcttggcca | tgtcccttgg | cttgtgtttc | 1140 |
| ttctttggcc | tgacaatttc | gctgcagtca | aaggacattt | tccctacct | tgtaatcctt | 1200 |
| gtgggattgg | aaaatagctt | ggtgatcaca | aagagcgtag | tctcaatgga | cgagacattc | 1260 |
| gacgtgaaga | tccgcgtggc | gcaggctctt | agcaaggagg | gttggcatat | atccaagact | 1320 |
| cttttgacgg | agataacaat | tttgacaatt | ggtcttgcta | cttttcgtgcc | cgtcatccag | 1380 |
| gagttttgta | tctttgccat | agtcggcttg | ctttccgatt | ttatgctaca | gatgctgctc | 1440 |
| ttctcaacaa | tactggccat | gaacattaag | cggaccgagt | atacggcgga | ggccaagcac | 1500 |
| cttcctaaga | tgttgctgag | ctgcacccaa | ggggctggtc | gacaggattt | ccgattttc | 1560 |
| ggggccgccc | cagcactgcc | accgtttgtc | cctggcacat | tcagcgttc | tcagtcgcat | 1620 |
| ccaaaactgt | gtttttgctga | tcccgcatct | gttagcgatc | gtacaagctt | ggttaatgga | 1680 |
| cactcgtcgc | cggagcaacg | aatacccaaa | cgcataaaga | ttgtaaattt | ctgggcgcgg | 1740 |
| actcgctttt | ttcagcgtgc | cttcatgatc | tggatgattg | tgtggatatg | ctctatagtt | 1800 |
| tataattcgg | gatatctgga | gcagttgttt | agcatgcaga | gcaacggcac | aatgacggca | 1860 |
| acccttgaac | ttcaacggcg | actacaggcg | ggtcggggag | cagtcagcag | ttttttcgag | 1920 |
| ggatggcaag | cggacgggca | gcgtgccacg | agtgcgccaa | gcggaagcgg | cttttctacg | 1980 |
| ccaataaaag | ctcctctagc | gatcgatata | aacgaaacgg | ccgaggaaat | gatgagactt | 2040 |
| cgatatccca | gcttcgacct | aaactatttc | ctttcaaact | tccactggtc | cacgattatg | 2100 |

```
aaacagtaca acatctcact aagtgggcac tacgttaccc tgctaccgac cattcgcctt    2160
agtcatgcca tcgctccgga gctagccact ctgttgcgga atccgcagga gcagctgcaa    2220
caaaatttc aatggaaggc cctagccgct gcactcgatc cgctggactt aacgatgac      2280
gacgtgcgcc gtgagtctcc gatggtaatg gcagaggggt tgcctctggt tcccaagagc    2340
cccatggaaa tattttcgc catcctcttg tgctgcatca gcatcttcgt gctttgctac     2400
acgatggtgg ttttctaccg ctgcatatgt accaggaact atgccgagtg cgctccagt     2460
tggcacgaat ctgaggcacc gtacaagcag actgagcaaa tcctggaggg agttccaacg    2520
caaatcgccg gacacaaaca tcgcattgaa tgcctggtgt ctgacggcgc ctacataatc    2580
agctgctgcc ttaaaggcca aatccgagtg tgggatgcac gcagtggcga gcagctaacc    2640
agcatctccc gatccgatat tcagatctct cagcagcgga cggatgggca gacgctggta    2700
cgaaagctgg ccgtgtcacc ggtctggtgc cttgactact tcgataatct aatcgcagta    2760
ggctgcgcca acggccgcgt agaattgtgg gaatcccctg cgggattgct taagtgtgca    2820
taccaggaag acgcgaagag aaaccagggt ataacccaca tccacctgaa cggcgatcga    2880
gtgattgtgg cgcgtcttaa tggccgacta gatttttacc gcttagagac gtactacaag    2940
gggaagcaaa tcgactgggg ttttaccctcg gcttacagga gaactcatgt tcgaactgga    3000
tccactggaa gcctgggatt aatgttgcag cagcagcgct gtcagcaaga agcatcccag    3060
aagaccacca aggaggaaat gaaaatcaca ttggagggtg taagactagc ccatcagcag    3120
ccaatcacat gcatgcaggt cgttaacgac atggttttca ctggcagcca ggatcacacc    3180
ctcaaggtgt attgcctcaa taagtcggat gttgagtata cgctccacgg tcactgtggg    3240
cctgtaacct gtctctttgt ggatcgctgg caacctggca caggggggtc tgggtcccag    3300
gacggcctgc tctgcgtatg ggatctgttc acgggagcct gcatgtataa tatacaagct    3360
cacgacggag ccgtcagctg cctggcctgt gcgcccagtt acgtaatctc gctaggcacg    3420
gacgagagga tttgcgtatg ggaacgattt cagggaaacc tgttgactac catcaacatc    3480
tcaaacgcat actcgagcct actgatgcta acaccgtcac tattggttac gagcaaaatg    3540
ggtaaggcct cattcttgat tgccaatata agagggacag taaataataa atttaattcc    3600
aacacaggat ctcttattgt gtgggatgtg cgcactgggc agccggctcg cgaggtcaaa    3660
ctggactttg caaacctgca gctctgtccc aaaataatga tgcttgcctg cgattcggta    3720
gtttgcgact acggaaatga gatccgcgtc gtccgctttc ctatcgtggc agacaagtgc    3780
cattaaagcg caaaatttta atttagcgtg gttcgctagc acctaggaat aagttgactt    3840
aaggctttaa aacgcctgga agtcattgac gcattcacta ttttatataa atatatacac    3900
tattagggtc cgcagcaact tacggtttta acacaagctg tacgtatctc atctctagaa    3960
ttttgtgtta gtttgtggac actaagtgta acagctacgc tccggtaggt taaggaacta    4020
aactaaatga atcagatata tacacatata ttttcgcgta attatataaa ctacatagtg    4080
tcttaaagcg cctcagccta atataaaatg actaaatgtt aaaataaa                 4128
```

<210> SEQ ID NO 6
<211> LENGTH: 1237
<212> TYPE: PRT
<213> ORGANISM: Drosophila melanogaster

<400> SEQUENCE: 6

```
Met Lys Asn Lys Thr Lys Ser Lys His Phe Ser Lys Ala Trp Lys Phe
1               5                   10                  15
```

-continued

```
Trp Pro Ala Cys Gly His Gly Lys Thr Phe Phe Gly Tyr Pro Leu Ile
             20                  25                  30

Asn Ile Pro Leu Pro Gly Thr Ile Pro Thr Lys Ile Val Val Pro Tyr
         35                  40                  45

Glu Thr Gly Ser Gly Ser Leu Ser Trp His Ser Leu Asn Thr Ser Ser
     50                  55                  60

Thr Thr Pro Gln Glu Pro His Pro Ser Gly Glu Pro Trp Pro Pro Glu
 65              70                  75                      80

Pro Gln Val Leu Asn Ser Ser Thr Thr Asp Arg Ser Pro Pro Pro Leu
                 85                  90                  95

Leu Pro Trp Ala Gln Ser Ser Pro Ala Phe Phe Tyr Val Gln Gln Ile
             100                 105                 110

Thr Leu Arg Thr Ser Val Leu Pro Trp Thr Glu Gly Met Gln Leu Met
         115                 120                 125

Asp Ala Phe Arg Ala Pro Leu His Glu Val Phe Lys Leu Leu Glu Ile
130              135                 140

Val Arg Asn His Gln Ser Ser Glu Asn Lys Arg Thr Leu Glu His Asn
145              150                 155                 160

Cys Leu His Val Asp Asn Val Lys Arg Gly Thr His Gly Gln Leu Asp
             165                 170                 175

Gln Ile Phe Pro Glu Tyr Gly Cys Leu Leu Leu Ser Pro Ala Asn Leu
         180                 185                 190

Trp Thr Gln Asn Ser Gln Asn Phe Thr Arg Asp Thr Asn Ile Leu Asn
     195                 200                 205

Thr Ile Phe Gln Tyr His Asn Leu Gln Lys Ser Lys Val Ser Ala Ala
 210                 215                 220

Glu Met Leu Phe Gly Leu Pro Met Gln Asp Thr Gly Phe Lys Arg Tyr
225              230                 235                 240

Pro Leu Arg Ala Arg Ser Arg Ile Ile Gln Tyr Ala Leu Thr Leu Phe
             245                 250                 255

Leu Lys His Asn Asp Met Glu Tyr Leu Asp Thr Leu Lys Glu Lys Leu
         260                 265                 270

Leu Arg His Tyr Pro Pro Leu Pro Leu Ala Ser Ala Ser Ala Glu Glu
     275                 280                 285

Pro Thr Thr Ile Thr Tyr Ile Phe Tyr Pro Gly Glu Tyr Arg Met Trp
 290                 295                 300

Glu Leu Val Pro Tyr Thr Val Ala Phe Met Leu Val Phe Ala Tyr Val
305              310                 315                 320

Tyr Phe Ser Val Arg Lys Ile Asp Val Phe Arg Ser Arg Phe Leu Leu
             325                 330                 335

Ala Leu Cys Ser Val Ile Thr Thr Ala Gly Ser Leu Ala Met Ser Leu
         340                 345                 350

Gly Leu Cys Phe Phe Phe Gly Leu Thr Ile Ser Leu Gln Ser Lys Asp
     355                 360                 365

Ile Phe Pro Tyr Leu Val Ile Leu Val Gly Leu Glu Asn Ser Leu Val
 370                 375                 380

Ile Thr Lys Ser Val Val Ser Met Asp Glu Thr Phe Asp Val Lys Ile
385              390                 395                 400

Arg Val Ala Gln Ala Leu Ser Lys Glu Gly Trp His Ile Ser Lys Thr
             405                 410                 415

Leu Leu Thr Glu Ile Thr Ile Leu Thr Ile Gly Leu Ala Thr Phe Val
         420                 425                 430

Pro Val Ile Gln Glu Phe Cys Ile Phe Ala Ile Val Gly Leu Leu Ser
```

-continued

```
              435                 440                 445
Asp Phe Met Leu Gln Met Leu Leu Phe Ser Thr Ile Leu Ala Met Asn
450                 455                 460
Ile Lys Arg Thr Glu Tyr Thr Ala Glu Ala Lys His Leu Pro Lys Met
465                 470                 475                 480
Leu Leu Ser Cys Thr Gln Gly Ala Gly Arg Gln Asp Phe Arg Phe Phe
                    485                 490                 495
Gly Ala Ala Pro Ala Leu Pro Pro Phe Val Pro Gly Thr Phe Gln Arg
                    500                 505                 510
Ser Gln Ser His Pro Lys Leu Cys Phe Ala Asp Pro Ala Ser Val Ser
                    515                 520                 525
Asp Arg Thr Ser Leu Val Asn Gly His Ser Ser Pro Glu Gln Arg Ile
530                 535                 540
Pro Lys Arg Ile Lys Ile Val Asn Phe Trp Ala Arg Thr Arg Phe Phe
545                 550                 555                 560
Gln Arg Ala Phe Met Ile Trp Met Ile Val Trp Ile Cys Ser Ile Val
                    565                 570                 575
Tyr Asn Ser Gly Tyr Leu Glu Gln Leu Phe Ser Met Gln Ser Asn Gly
                    580                 585                 590
Thr Met Thr Ala Thr Leu Glu Leu Gln Arg Arg Leu Gln Ala Gly Arg
                    595                 600                 605
Gly Ala Val Ser Ser Phe Phe Glu Gly Trp Gln Ala Asp Gly Gln Arg
                    610                 615                 620
Ala Thr Ser Ala Pro Ser Gly Ser Gly Phe Ser Thr Pro Ile Lys Ala
625                 630                 635                 640
Pro Leu Ala Ile Asp Ile Asn Glu Thr Ala Glu Glu Met Met Arg Leu
                    645                 650                 655
Arg Tyr Pro Ser Phe Asp Leu Asn Tyr Phe Leu Ser Asn Phe His Trp
                    660                 665                 670
Ser Thr Ile Met Lys Gln Tyr Asn Ile Ser Leu Ser Gly His Tyr Val
                    675                 680                 685
Thr Leu Leu Pro Thr Ile Arg Leu Ser His Ala Ile Ala Pro Glu Leu
690                 695                 700
Ala Thr Leu Leu Arg Asn Pro Gln Glu Gln Leu Gln Gln Asn Phe Gln
705                 710                 715                 720
Trp Lys Ala Leu Ala Ala Leu Asp Pro Leu Asp Phe Asn Asp Asp
                    725                 730                 735
Asp Val Arg Arg Glu Ser Pro Met Val Met Ala Glu Gly Leu Pro Leu
                    740                 745                 750
Val Pro Lys Ser Pro Met Glu Ile Phe Phe Ala Ile Leu Leu Cys Cys
                    755                 760                 765
Ile Ser Ile Phe Val Leu Cys Tyr Thr Met Val Val Phe Tyr Arg Cys
770                 775                 780
Ile Cys Thr Arg Asn Tyr Ala Glu Trp Arg Ser Ser Trp His Glu Ser
785                 790                 795                 800
Glu Ala Pro Tyr Lys Gln Thr Glu Gln Ile Leu Glu Gly Val Pro Thr
                    805                 810                 815
Gln Ile Ala Gly His Lys His Arg Ile Glu Cys Leu Val Ser Asp Gly
                    820                 825                 830
Ala Tyr Ile Ile Ser Cys Cys Leu Lys Gly Gln Ile Arg Val Trp Asp
                    835                 840                 845
Ala Arg Ser Gly Glu Gln Leu Thr Ser Ile Ser Arg Ser Asp Ile Gln
850                 855                 860
```

```
Ile Ser Gln Gln Arg Thr Asp Gly Gln Thr Leu Val Arg Lys Leu Ala
865                 870                 875                 880

Val Ser Pro Val Trp Cys Leu Asp Tyr Phe Asp Asn Leu Ile Ala Val
                885                 890                 895

Gly Cys Ala Asn Gly Arg Val Glu Leu Trp Glu Ser Pro Ala Gly Leu
                900                 905                 910

Leu Lys Cys Ala Tyr Gln Glu Asp Ala Lys Arg Asn Gln Gly Ile Thr
                915                 920                 925

His Ile His Leu Asn Gly Asp Arg Val Ile Val Ala Arg Leu Asn Gly
                930                 935                 940

Arg Leu Asp Phe Tyr Arg Leu Glu Thr Tyr Tyr Lys Gly Lys Gln Ile
945                 950                 955                 960

Asp Trp Gly Phe Thr Ser Ala Tyr Arg Arg Thr His Val Arg Thr Gly
                965                 970                 975

Ser Thr Gly Ser Leu Gly Leu Met Leu Gln Gln Gln Arg Cys Gln Gln
                980                 985                 990

Glu Ala Ser Gln Lys Thr Thr Lys Glu Glu Met Lys Ile Thr Leu Glu
                995                 1000                1005

Gly Val Arg Leu Ala His Gln Gln Pro Ile Thr Cys Met Gln Val
    1010                1015                1020

Val Asn Asp Met Val Phe Thr Gly Ser Gln Asp His Thr Leu Lys
    1025                1030                1035

Val Tyr Cys Leu Asn Lys Ser Asp Val Glu Tyr Thr Leu His Gly
    1040                1045                1050

His Cys Gly Pro Val Thr Cys Leu Phe Val Asp Arg Trp Gln Pro
    1055                1060                1065

Gly Thr Gly Gly Ser Gly Ser Gln Asp Gly Leu Leu Cys Val Trp
    1070                1075                1080

Asp Leu Phe Thr Gly Ala Cys Met Tyr Asn Ile Gln Ala His Asp
    1085                1090                1095

Gly Ala Val Ser Cys Leu Ala Cys Ala Pro Ser Tyr Val Ile Ser
    1100                1105                1110

Leu Gly Thr Asp Glu Arg Ile Cys Val Trp Glu Arg Phe Gln Gly
    1115                1120                1125

Asn Leu Leu Thr Thr Ile Asn Ile Ser Asn Ala Tyr Ser Ser Leu
    1130                1135                1140

Leu Met Leu Thr Pro Ser Leu Leu Val Thr Ser Lys Met Gly Lys
    1145                1150                1155

Ala Ser Phe Leu Ile Ala Asn Ile Arg Gly Thr Val Asn Asn Lys
    1160                1165                1170

Phe Asn Ser Asn Thr Gly Ser Leu Ile Val Trp Asp Val Arg Thr
    1175                1180                1185

Gly Gln Pro Ala Arg Glu Val Lys Leu Asp Phe Ala Asn Leu Gln
    1190                1195                1200

Leu Cys Pro Lys Ile Met Met Leu Ala Cys Asp Ser Val Val Cys
    1205                1210                1215

Asp Tyr Gly Asn Glu Ile Arg Val Val Arg Phe Pro Ile Val Ala
    1220                1225                1230

Asp Lys Cys His
    1235

<210> SEQ ID NO 7
<211> LENGTH: 3768
```

<212> TYPE: DNA
<213> ORGANISM: Drosophila melanogaster

<400> SEQUENCE: 7

| | | | | | |
|---|---|---|---|---|---|
| gtttattaag | ctgcaaatat | actcgtgaaa | aaaatcaaaa | caaccatgaa | caacaagtgt | 60 |
| tgcaactatt | actaactagt | cgctagttta | aagcaaagtg | cgttgacatt | aaccagttat | 120 |
| ggaaaaacaa | aagcacacgt | gaactaagaa | aacagataga | aggtggtaaa | gcattcgcaa | 180 |
| tggacacgac | actgatgaac | ttaatagacg | ctccgctgga | cgagtccatg | gatttgttca | 240 |
| aagcggagga | tgtcttcgaa | ccgttcgacg | ccgacctgca | ctcggacatg | ctggacatca | 300 |
| tcctcaacga | catggacctg | gcgccgacgc | agatgtacaa | catgctgctg | gacgagcctc | 360 |
| gaacgcatac | ccagcagacg | cagtccgtgg | atcagcagcc | gcaatccgtc | gagcaacagc | 420 |
| cgcacgtgaa | aagcgagcac | tcttcgccag | tgcacatcaa | ggaggaactg | catcagcagc | 480 |
| aacaacagtc | gccgcttctc | gtctacaaac | cagatcccct | catagccaca | agctacaatt | 540 |
| gtccccagca | acagccgacg | ggccttttga | aggccgccca | accaacagcc | accatacatc | 600 |
| acatggacgc | ccagcggatg | ccgccgaaca | cggcggtgta | tccccatct | ctgggcagta | 660 |
| gctttgtcta | ccagtccatg | tccccgccca | cgtcgccggt | ggagtctgcg | aaccagaatg | 720 |
| tcaatgtcat | gcagcccgtt | gctgcaactc | ctgctcccgc | ttctgctcct | ttgccccagc | 780 |
| agtcgtatcc | gcaacccttc | attacgtaca | actctaaggc | cggaatgact | tccgatgaag | 840 |
| ccatgtactt | gctcttgcag | cccacggtag | ccagtccaac | cccatctcca | cctgtggctc | 900 |
| caccaccgac | aagcacaggt | agtcgggcca | gcaaggtgcg | agtggcacca | ctggctccgt | 960 |
| cacctgccgc | tatggaagtc | cagggcaagg | tacctatcaa | ccgggttcaa | cccaaggtga | 1020 |
| aggaagtaaa | gcgctcggcc | cacaacgcca | tcgagcggcg | ctatcgcacc | tcaatcaacg | 1080 |
| acaagattaa | cgagttgaag | aacttggtag | tgggagagca | ggccaagctg | aacaagtccg | 1140 |
| cagtgttgcg | gaaatccata | gacaagattc | gggatctgca | acgccagaat | cacgatctga | 1200 |
| aggcagagtt | gcagcgcctg | cagagggagc | taatggcacg | cgacggctcc | aaggtgaagg | 1260 |
| atttacttca | gctgggcact | cggcctggta | gagcatccaa | gaagcgccgc | gagagctcgc | 1320 |
| agacctttac | cacggatgcc | ggactgacgc | cgccacgcag | cgatgaatcg | gatccttcgc | 1380 |
| tctcgcccat | gcactcggac | atctcgttgc | cgccatcacc | ctatggtgga | tccaccgcca | 1440 |
| gctgtagcag | tggcagcagc | agcagcaatg | aagaaccact | ggtggtgccc | agctctatgc | 1500 |
| gcggcatggc | cacccactct | cgcctcggac | tctgcatgtt | tatgttcgcc | atcctggccg | 1560 |
| tcaatccctt | caagaccttt | ctccagcgcg | gccactatga | cagtaatgac | gatcttggcg | 1620 |
| acatgagcgg | tcaaagacgc | attctctctt | acgacgtgga | aggtgaaggt | tttgctgtct | 1680 |
| ggcagcagag | ttcctggata | tggctattga | acttcacact | gatgcttgga | tgcttggtga | 1740 |
| aattgctggt | ttacggtgat | ccgcagctgg | acgcgcaaac | ggacgcctac | tgccagcaca | 1800 |
| ggcagcgggc | tgacttctat | tttagccaag | acagtcgtc | tcaggcctac | gccggttacc | 1860 |
| tcaactgtct | gcatatgttt | ggattaagtc | taccggcgtc | gcgcttggag | tgttacttgc | 1920 |
| agaccacgtg | gcagttcctt | cgtttctttt | tccatcgcct | ctggctgggt | cgggtgctgt | 1980 |
| cacggcggtc | cggtgggctg | tttagcaacg | ccgccagcag | gaaacaggcg | ctggcatctg | 2040 |
| cacgcgaact | ggccctgctc | ttcaaccgac | tgaatcaatt | gcaactgact | ggaaatggaa | 2100 |
| gccgcggtga | catgaacggc | attatgatgg | cactattcgc | aagcaacatg | gctgaagtgg | 2160 |
| cgcacaatct | actgacaccg | cgcgagacca | tctgcatcca | cgtaatgaca | gcgttgcgaa | 2220 |

-continued

```
tgaagcgcag tgccccaaaa tggttgcaac agttcttcgc ccgatactac atgagccggg    2280
ctcgtcaaga gtgcggtcgc actagggcca ccgagcaaac gcaggagcta cgttgggcat    2340
tcacagccta tggatatcgc tactgcgcca cgcacgtctt cacgtacgat ctgagcgact    2400
ccggcgagca ggatggattc ttcacacgtc ttaggaatcc atgtgatccc gctgcccacg    2460
tcattaagca atatcgagag catttgctgt ttaaatccat tcagtgtctg gtaggagcgg    2520
gccacaaatc ggggaggcctg cccacatctt ctgtcagcgg agaggcggaa cagttgcagc    2580
aacagcagca cagcggcacc attgtcagca atgttcttaa gtacacgtcc ctccttaagg    2640
acactctctg ggctgatgag gatgagcggg atacaaacgt ggtgtggtgg gccgatgttt    2700
tggagaccgc agtgcactgg ctccttggtg aagacacgct ggccgagcaa ttgtacggca    2760
ggatcaagca aatgcccacg cagctgcaac agtgcggcga aaacgatcat ctgcccaagg    2820
cgctgcatgc tgtgctgcga gctaagatga tcttactaaa aaacaatggc aacgcactgg    2880
acaaaagtct caagcaattg gtaaacatcc tctgcgatga gtcgagtgtg gagctccaag    2940
agtgcttgac tgtcaaccgg atcaccgacg ccaagggtat aaagctgctt ttccagttgc    3000
ttacctgcga ttggctgctc gaaactagga ctgctctgtg ggaactggaa cacatgaata    3060
tggaggacga tggcttctac caagtgccag gtgaagtgct cgagaagttc cagaccgatt    3120
tgaactcgtt gcgcaacatt gtggagaata taccgaacgc ccaatcgcgc atatatttgt    3180
acgaggcagt ttgtcgcctg atggctggag cctcaccgtg tccaacgcaa cagctcttgg    3240
acaggagtct gcgatcacgc aacgcccact cgtccatctt ctgcggcagc aaggatcggc    3300
ggcagcagaa cttcgtgggc ggagagcggg aacgggcttc ggccatgtac gtggcctgca    3360
agtatctccc gcctgcgctg ctcagctccc cgggtgaacg tgctggcatg ttagccgagg    3420
cggccaagac cctggagaag gtgggcgaca agcgaaagct caaggagtgc taccagctga    3480
tgaagtcgct gggcaacggc attggcagcg tgaaggctta ggatagtagt gaagtacata    3540
ataagtggca cgaacgtggt gtggattttc agcaaatgaa tacccgtttg ctattcaaaa    3600
gaattacaaa tgcctaggtc tttataatta cgctattcct ctgttttcca cgcccggtta    3660
tgcttagatt gtaattttaa aattatttaa tatggacatt ttatttgttt attatttacc    3720
gtacttgtta aacgtattta taacaataaa tattttaaca gatttaaa                 3768
```

<210> SEQ ID NO 8
<211> LENGTH: 1113
<212> TYPE: PRT
<213> ORGANISM: Drosophila melanogaster

<400> SEQUENCE: 8

```
Met Asp Thr Thr Leu Met Asn Leu Ile Asp Ala Pro Leu Asp Glu Ser
 1               5                   10                  15

Met Asp Leu Phe Lys Ala Glu Asp Val Phe Glu Pro Phe Asp Ala Asp
                20                  25                  30

Leu His Ser Asp Met Leu Asp Ile Ile Leu Asn Asp Met Asp Leu Ala
            35                  40                  45

Pro Thr Gln Met Tyr Asn Met Leu Leu Asp Glu Pro Arg Thr His Thr
        50                  55                  60

Gln Gln Thr Gln Ser Val Asp Gln Gln Pro Ser Val Glu Gln Gln
 65                 70                  75                  80

Pro His Val Lys Ser Glu His Ser Ser Pro Val His Ile Lys Glu Glu
                85                  90                  95

Leu His Gln Gln Gln Gln Gln Ser Pro Leu Leu Val Tyr Lys Pro Asp
```

-continued

```
                100                 105                 110
Pro Leu Ile Ala Thr Ser Tyr Asn Cys Pro Gln Gln Gln Pro Thr Gly
            115                 120                 125
Leu Leu Lys Ala Ala Gln Pro Thr Ala Thr Ile His His Met Asp Ala
        130                 135                 140
Gln Arg Met Pro Pro Asn Thr Ala Val Tyr Pro Pro Ser Leu Gly Ser
145                 150                 155                 160
Ser Phe Val Tyr Gln Ser Met Ser Pro Pro Thr Ser Pro Val Glu Ser
                165                 170                 175
Ala Asn Gln Asn Val Asn Val Met Gln Pro Val Ala Ala Thr Pro Ala
            180                 185                 190
Pro Ala Ser Ala Pro Leu Pro Gln Gln Ser Tyr Pro Gln Pro Phe Ile
        195                 200                 205
Thr Tyr Asn Ser Lys Ala Gly Met Thr Ser Asp Glu Ala Met Tyr Leu
    210                 215                 220
Leu Leu Gln Pro Thr Val Ala Ser Pro Thr Pro Ser Pro Pro Val Ala
225                 230                 235                 240
Pro Pro Pro Thr Ser Thr Gly Ser Arg Ala Ser Lys Val Arg Val Ala
                245                 250                 255
Pro Leu Ala Pro Ser Pro Ala Ala Met Glu Val Gln Gly Lys Val Pro
            260                 265                 270
Ile Asn Arg Val Gln Pro Lys Val Lys Glu Val Lys Arg Ser Ala His
        275                 280                 285
Asn Ala Ile Glu Arg Arg Tyr Arg Thr Ser Ile Asn Asp Lys Ile Asn
        290                 295                 300
Glu Leu Lys Asn Leu Val Val Gly Glu Gln Ala Lys Leu Asn Lys Ser
305                 310                 315                 320
Ala Val Leu Arg Lys Ser Ile Asp Lys Ile Arg Asp Leu Gln Arg Gln
                325                 330                 335
Asn His Asp Leu Lys Ala Glu Leu Gln Arg Leu Gln Arg Glu Leu Met
            340                 345                 350
Ala Arg Asp Gly Ser Lys Val Lys Asp Leu Leu Gln Leu Gly Thr Arg
        355                 360                 365
Pro Gly Arg Ala Ser Lys Lys Arg Arg Glu Ser Ser Gln Thr Phe Thr
    370                 375                 380
Thr Asp Ala Gly Leu Thr Pro Pro Arg Ser Asp Glu Ser Asp Pro Ser
385                 390                 395                 400
Leu Ser Pro Met His Ser Asp Ile Ser Leu Pro Pro Ser Pro Tyr Gly
                405                 410                 415
Gly Ser Thr Ala Ser Cys Ser Ser Gly Ser Ser Ser Ser Asn Glu Glu
            420                 425                 430
Pro Leu Val Val Pro Ser Ser Met Arg Gly Met Ala Thr His Ser Arg
        435                 440                 445
Leu Gly Leu Cys Met Phe Met Phe Ala Ile Leu Ala Val Asn Pro Phe
    450                 455                 460
Lys Thr Phe Leu Gln Arg Gly His Tyr Asp Ser Asn Asp Asp Leu Gly
465                 470                 475                 480
Asp Met Ser Gly Gln Arg Arg Ile Leu Ser Tyr Asp Val Glu Gly Glu
                485                 490                 495
Gly Phe Ala Val Trp Gln Gln Ser Ser Trp Ile Trp Leu Leu Asn Phe
            500                 505                 510
Thr Leu Met Leu Gly Cys Leu Val Lys Leu Leu Val Tyr Gly Asp Pro
        515                 520                 525
```

```
Gln Leu Asp Ala Gln Thr Asp Ala Tyr Cys Gln His Arg Gln Arg Ala
    530                 535                 540
Asp Phe Tyr Phe Ser Gln Gly Gln Ser Ser Gln Ala Tyr Ala Gly Tyr
545                 550                 555                 560
Leu Asn Cys Leu His Met Phe Gly Leu Ser Leu Pro Ala Ser Arg Leu
                565                 570                 575
Glu Cys Tyr Leu Gln Thr Thr Trp Gln Phe Leu Arg Phe Leu Phe His
                580                 585                 590
Arg Leu Trp Leu Gly Arg Val Leu Ser Arg Arg Ser Gly Gly Leu Phe
        595                 600                 605
Ser Asn Ala Ala Ser Arg Lys Gln Ala Leu Ala Ser Ala Arg Glu Leu
    610                 615                 620
Ala Leu Leu Phe Asn Arg Leu Asn Gln Leu Gln Leu Thr Gly Asn Gly
625                 630                 635                 640
Ser Arg Gly Asp Met Asn Gly Ile Met Met Ala Leu Phe Ala Ser Asn
                645                 650                 655
Met Ala Glu Val Ala His Asn Leu Leu Thr Pro Arg Glu Thr Ile Cys
                660                 665                 670
Ile His Val Met Thr Ala Leu Arg Met Lys Arg Ser Ala Pro Lys Trp
        675                 680                 685
Leu Gln Gln Phe Phe Ala Arg Tyr Tyr Met Ser Arg Ala Arg Gln Glu
    690                 695                 700
Cys Gly Arg Thr Arg Ala Thr Glu Gln Thr Gln Glu Leu Arg Trp Ala
705                 710                 715                 720
Phe Thr Ala Tyr Gly Tyr Arg Tyr Cys Ala Thr His Val Phe Thr Tyr
                725                 730                 735
Asp Leu Ser Asp Ser Gly Glu Gln Asp Gly Phe Phe Thr Arg Leu Arg
                740                 745                 750
Asn Pro Cys Asp Pro Ala Ala His Val Ile Lys Gln Tyr Arg Glu His
        755                 760                 765
Leu Leu Phe Lys Ser Ile Gln Cys Leu Val Gly Ala Gly His Lys Ser
    770                 775                 780
Gly Gly Leu Pro Thr Ser Ser Val Ser Gly Glu Ala Glu Gln Leu Gln
785                 790                 795                 800
Gln Gln Gln His Ser Gly Thr Ile Val Ser Asn Val Leu Lys Tyr Thr
                805                 810                 815
Ser Leu Leu Lys Asp Thr Leu Trp Ala Asp Glu Asp Glu Arg Asp Thr
                820                 825                 830
Asn Val Val Trp Trp Ala Asp Val Leu Glu Thr Ala Val His Trp Leu
        835                 840                 845
Leu Gly Glu Asp Thr Leu Ala Glu Gln Leu Tyr Gly Arg Ile Lys Gln
    850                 855                 860
Met Pro Thr Gln Leu Gln Gln Cys Gly Glu Asn Asp His Leu Pro Lys
865                 870                 875                 880
Ala Leu His Ala Val Leu Arg Ala Lys Met Ile Leu Leu Lys Asn Asn
                885                 890                 895
Gly Asn Ala Leu Asp Lys Ser Leu Lys Gln Leu Val Asn Ile Leu Cys
                900                 905                 910
Asp Glu Ser Ser Val Glu Leu Gln Glu Cys Leu Thr Val Asn Arg Ile
        915                 920                 925
Thr Asp Ala Lys Gly Ile Lys Leu Leu Phe Gln Leu Leu Thr Cys Asp
    930                 935                 940
```

-continued

Trp Leu Leu Glu Thr Arg Thr Ala Leu Trp Glu Leu Glu His Met Asn
945                 950                 955                 960

Met Glu Asp Asp Gly Phe Tyr Gln Val Pro Gly Val Leu Glu Lys
            965                 970                 975

Phe Gln Thr Asp Leu Asn Ser Leu Arg Asn Ile Val Glu Asn Ile Pro
        980                 985                 990

Asn Ala Gln Ser Arg Ile Tyr Leu Tyr Glu Ala Val Cys Arg Leu Met
        995                 1000                1005

Ala Gly Ala Ser Pro Cys Pro Thr Gln Gln Leu Leu Asp Arg Ser
    1010                1015                1020

Leu Arg Ser Arg Asn Ala His Ser Ser Ile Phe Cys Gly Ser Lys
    1025                1030                1035

Asp Arg Arg Gln Gln Asn Phe Val Gly Gly Glu Arg Glu Arg Ala
    1040                1045                1050

Ser Ala Met Tyr Val Ala Cys Lys Tyr Leu Pro Pro Ala Leu Leu
    1055                1060                1065

Ser Ser Pro Gly Glu Arg Ala Gly Met Leu Ala Glu Ala Ala Lys
    1070                1075                1080

Thr Leu Glu Lys Val Gly Asp Lys Arg Lys Leu Lys Glu Cys Tyr
    1085                1090                1095

Gln Leu Met Lys Ser Leu Gly Asn Gly Ile Gly Ser Val Lys Ala
    1100                1105                1110

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide

<400> SEQUENCE: 9
gactacttct agatggcgag c                                            21

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide

<400> SEQUENCE: 10
atcgataata cgactcacta taggg                                        25

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide

<400> SEQUENCE: 11
caggacactc cgcctaacga                                              20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide

<400> SEQUENCE: 12
acttactcgt caaattactc                                                   20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide

<400> SEQUENCE: 13
gtggcctcca gttgctcatg                                                   20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide

<400> SEQUENCE: 14
cttgtattag aaaaaaagtg                                                   20

<210> SEQ ID NO 15
<211> LENGTH: 22
<212> TYPE: DNA
<213> ORGANISM: Artificial Sequence
<220> FEATURE:
<223> OTHER INFORMATION: Oligonucleotide

<400> SEQUENCE: 15
tgccgcccat ccaaaagcct gc                                                22

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide

<400> SEQUENCE: 16
tatacttcgg aaccccaagt gg                                                22

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide

<400> SEQUENCE: 17
gctcggtcat gcgtgggcgg                                                   20

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide

<400> SEQUENCE: 18
tagccgcctc gacagattcc                                                   20

<210> SEQ ID NO 19
<211> LENGTH: 20
<212> TYPE: DNA
<213> ORGANISM: Artificial Sequence

```
<220> FEATURE:
<223> OTHER INFORMATION: Oligonucleotide

<400> SEQUENCE: 19
caccgcacgg aagccgacga                                              20

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide

<400> SEQUENCE: 20
ctcattgagc tgccccacaa                                              20

<210> SEQ ID NO 21
<211> LENGTH: 30
<212> TYPE: DNA
<213> ORGANISM: Artificial Sequence
<220> FEATURE:
<223> OTHER INFORMATION: Oligonucleotide

<400> SEQUENCE: 21
cgtgggtatt ccttgttcga agccagctac                                   30

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide

<400> SEQUENCE: 22
tcaagtcaaa tggatgcttg aga                                          23

<210> SEQ ID NO 23
<211> LENGTH: 30
<212> TYPE: DNA
<213> ORGANISM: Artificial Sequence
<220> FEATURE:
<223> OTHER INFORMATION: Oligonucleotide

<400> SEQUENCE: 23
tcacaagctg atcgactcga tgccacgtcg                                   30

<210> SEQ ID NO 24
<211> LENGTH: 25
<212> TYPE: DNA
<213> ORGANISM: Artificial Sequence
<220> FEATURE:
<223> OTHER INFORMATION: Oligonucleotide

<400> SEQUENCE: 24
gattttgtga acactgtggt gaagt                                        25

<210> SEQ ID NO 25
<211> LENGTH: 27
<212> TYPE: DNA
<213> ORGANISM: Artificial Sequence
<220> FEATURE:
<223> OTHER INFORMATION: Oligonucleotide

<400> SEQUENCE: 25
ccatcctaat acgactcact atagggc                                      27
```

```
<210> SEQ ID NO 26
<211> LENGTH: 99
<212> TYPE: DNA
<213> ORGANISM: Artificial Sequence
<220> FEATURE:
<223> OTHER INFORMATION: Oligonucleotide

<400> SEQUENCE: 26
ctggaattca acatggatcc agtggtggtg ctgggactct gcctctcctg cttgcttctc      60
ctttcactct ggaagcagag ctatggagga ggaaagctt                            99

<210> SEQ ID NO 27
<211> LENGTH: 103
<212> TYPE: DNA
<213> ORGANISM: Artificial Sequence
<220> FEATURE:
<223> OTHER INFORMATION: Oligonucleotide

<400> SEQUENCE: 27
aagctttcct cctccatagc tctgcttcca gagtgaaagg agaagcaagc aggagaggca      60
gagtcccagc accaccactg gatccatgtt gaattccaga gct                      103

<210> SEQ ID NO 28
<211> LENGTH: 32
<212> TYPE: DNA
<213> ORGANISM: Artificial Sequence
<220> FEATURE:
<223> OTHER INFORMATION: Oligonucleotide

<400> SEQUENCE: 28
atgggcgcgc caaccaaagt gtgatgcaac ag                                   32

<210> SEQ ID NO 29
<211> LENGTH: 34
<212> TYPE: DNA
<213> ORGANISM: Artificial Sequence
<220> FEATURE:
<223> OTHER INFORMATION: Oligonucleotide

<400> SEQUENCE: 29
gagggtacct cgttcattct gaaaaaaaaa agtc                                 34

<210> SEQ ID NO 30
<211> LENGTH: 10
<212> TYPE: DNA
<213> ORGANISM: Mammalian Sterol Regulatory Element 1 (SRE1)

<400> SEQUENCE: 30
atcaccccac                                                            10

<210> SEQ ID NO 31
<211> LENGTH: 22
<212> TYPE: DNA
<213> ORGANISM: Artificial Sequence
<220> FEATURE:
<223> OTHER INFORMATION: Oligonucleotide

<400> SEQUENCE: 31
gtacgacgct cggttttggg tc                                              22

<210> SEQ ID NO 32
<211> LENGTH: 22
<212> TYPE: DNA
<213> ORGANISM: Artificial Sequence
```

```
<220> FEATURE:
<223> OTHER INFORMATION: Oligonucleotide

<400> SEQUENCE: 32
ggtttaatta cccaagtttg ag                                              22

<210> SEQ ID NO 33
<211> LENGTH: 22
<212> TYPE: DNA
<213> ORGANISM: Artificial Sequence
<220> FEATURE:
<223> OTHER INFORMATION: Oligonucleotide

<400> SEQUENCE: 33
agcaatggaa catatcaacg gg                                              22

<210> SEQ ID NO 34
<211> LENGTH: 25
<212> TYPE: DNA
<213> ORGANISM: Artificial Sequence
<220> FEATURE:
<223> OTHER INFORMATION: Oligonucleotide

<400> SEQUENCE: 34
caattcaaag atccatagaa gtatg                                           25

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide

<400> SEQUENCE: 35
gcatgttcag cgacgaatgg                                                 20

<210> SEQ ID NO 36
<211> LENGTH: 20
<212> TYPE: DNA
<213> ORGANISM: Artificial Sequence
<220> FEATURE:
<223> OTHER INFORMATION: Oligonucleotide

<400> SEQUENCE: 36
gcaacactac gacgggctat                                                 20

<210> SEQ ID NO 37
<211> LENGTH: 20
<212> TYPE: DNA
<213> ORGANISM: Artificial Sequence
<220> FEATURE:
<223> OTHER INFORMATION: Oligonucleotide

<400> SEQUENCE: 37
tggattgctc gctggaagtg                                                 20

<210> SEQ ID NO 38
<211> LENGTH: 20
<212> TYPE: DNA
<213> ORGANISM: Artificial Sequence
<220> FEATURE:
<223> OTHER INFORMATION: Oligonucleotide

<400> SEQUENCE: 38
ggaacttgtc ggtggtgacg                                                 20
```

<210> SEQ ID NO 39
<211> LENGTH: 20
<212> TYPE: DNA
<213> ORGANISM: Artificial Sequence
<220> FEATURE:
<223> OTHER INFORMATION: Oligonucleotide

<400> SEQUENCE: 39
cccttgaagc tttgtgtcca                    20

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide

<400> SEQUENCE: 40
cgtggaagtc cgtcgtttga                    20

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide

<400> SEQUENCE: 41
ggtcaccatg gatcagcagt                    20

<210> SEQ ID NO 42
<211> LENGTH: 20
<212> TYPE: DNA
<213> ORGANISM: Artificial Sequence
<220> FEATURE:
<223> OTHER INFORMATION: Oligonucleotide

<400> SEQUENCE: 42
cgttggatcg atcgcttcca                    20

<210> SEQ ID NO 43
<211> LENGTH: 20
<212> TYPE: DNA
<213> ORGANISM: Artificial Sequence
<220> FEATURE:
<223> OTHER INFORMATION: Oligonucleotide

<400> SEQUENCE: 43
ccgccgaaga ttttgacaga                    20

<210> SEQ ID NO 44
<211> LENGTH: 20
<212> TYPE: DNA
<213> ORGANISM: Artificial Sequence
<220> FEATURE:
<223> OTHER INFORMATION: Oligonucleotide

<400> SEQUENCE: 44
tgggacaagg ggagattgtt                    20

<210> SEQ ID NO 45
<211> LENGTH: 20
<212> TYPE: DNA
<213> ORGANISM: Artificial Sequence
<220> FEATURE:
<223> OTHER INFORMATION: Oligonucleotide

```
<400> SEQUENCE: 45
gaacgtgcgt ccaccatgtg                                               20

<210> SEQ ID NO 46
<211> LENGTH: 20
<212> TYPE: DNA
<213> ORGANISM: Artificial Sequence
<220> FEATURE:
<223> OTHER INFORMATION: Oligonucleotide

<400> SEQUENCE: 46
gctccaacct tttcgcatct                                               20

<210> SEQ ID NO 47
<211> LENGTH: 20
<212> TYPE: DNA
<213> ORGANISM: Artificial Sequence
<220> FEATURE:
<223> OTHER INFORMATION: Oligonucleotide

<400> SEQUENCE: 47
ggagatgatt cgacgggtga                                               20

<210> SEQ ID NO 48
<211> LENGTH: 20
<212> TYPE: DNA
<213> ORGANISM: Artificial Sequence
<220> FEATURE:
<223> OTHER INFORMATION: Oligonucleotide

<400> SEQUENCE: 48
tccccggaat cactatcctc                                               20

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide

<400> SEQUENCE: 49
gcagcgtcgc ttttgttaa                                                20

<210> SEQ ID NO 50
<211> LENGTH: 20
<212> TYPE: DNA
<213> ORGANISM: Artificial Sequence
<220> FEATURE:
<223> OTHER INFORMATION: Oligonucleotide

<400> SEQUENCE: 50
tgatggtggt gatgaggtgg                                               20

<210> SEQ ID NO 51
<211> LENGTH: 20
<212> TYPE: DNA
<213> ORGANISM: Artificial Sequence
<220> FEATURE:
<223> OTHER INFORMATION: Oligonucleotide

<400> SEQUENCE: 51
aattgttggg tggcggctag                                               20

<210> SEQ ID NO 52
```

```
<211> LENGTH: 20
<212> TYPE: DNA
<213> ORGANISM: Artificial Sequence
<220> FEATURE:
<223> OTHER INFORMATION: Oligonucleotide

<400> SEQUENCE: 52
ccagctcaag gcccatcagg                                                 20

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide

<400> SEQUENCE: 53
tcactatcct catcatcctc                                                 20

<210> SEQ ID NO 54
<211> LENGTH: 20
<212> TYPE: DNA
<213> ORGANISM: Artificial Sequence
<220> FEATURE:
<223> OTHER INFORMATION: Oligonucleotide

<400> SEQUENCE: 54
gtacccggaa ccaatcaata                                                 20

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide

<400> SEQUENCE: 55
ctgatgaatt tcatgataga                                                 20

<210> SEQ ID NO 56
<211> LENGTH: 37
<212> TYPE: DNA
<213> ORGANISM: Artificial Sequence
<220> FEATURE:
<223> OTHER INFORMATION: Oligonucleotide

<400> SEQUENCE: 56
cccgagctca tgcgattttc cccgccaaac tttgatc                              37

<210> SEQ ID NO 57
<211> LENGTH: 38
<212> TYPE: DNA
<213> ORGANISM: Artificial Sequence
<220> FEATURE:
<223> OTHER INFORMATION: Oligonucleotide

<400> SEQUENCE: 57
gggcaattgc taaagggtaa ctttcgaaga tccatctc                             38

<210> SEQ ID NO 58
<211> LENGTH: 22
<212> TYPE: DNA
<213> ORGANISM: Artificial Sequence
<220> FEATURE:
<223> OTHER INFORMATION: Oligonucleotide

<400> SEQUENCE: 58
```
cccactctgt caaaatcttc gg                22

<210> SEQ ID NO 59
<211> LENGTH: 22
<212> TYPE: DNA
<213> ORGANISM: Artificial Sequence
<220> FEATURE:
<223> OTHER INFORMATION: Oligonucleotide

<400> SEQUENCE: 59
tcagtgaata gtgttgccgt gc                22

<210> SEQ ID NO 60
<211> LENGTH: 22
<212> TYPE: DNA
<213> ORGANISM: Artificial Sequence
<220> FEATURE:
<223> OTHER INFORMATION: Oligonucleotide

<400> SEQUENCE: 60
agcaatggaa catatcaacg gg                22

<210> SEQ ID NO 61
<211> LENGTH: 22
<212> TYPE: DNA
<213> ORGANISM: Artificial Sequence
<220> FEATURE:
<223> OTHER INFORMATION: Oligonucleotide

<400> SEQUENCE: 61
acgaccaagg ttttcttttc cc                22

<210> SEQ ID NO 62
<211> LENGTH: 22
<212> TYPE: DNA
<213> ORGANISM: Artificial Sequence
<220> FEATURE:
<223> OTHER INFORMATION: Oligonucleotide

<400> SEQUENCE: 62
tcattgaggt atggtgtggt gg                22

<210> SEQ ID NO 63
<211> LENGTH: 22
<212> TYPE: DNA
<213> ORGANISM: Artificial Sequence
<220> FEATURE:
<223> OTHER INFORMATION: Oligonucleotide

<400> SEQUENCE: 63
gacctccacc catttttgtg ag                22

<210> SEQ ID NO 64
<211> LENGTH: 22
<212> TYPE: DNA
<213> ORGANISM: Artificial Sequence
<220> FEATURE:
<223> OTHER INFORMATION: Oligonucleotide

<400> SEQUENCE: 64
tgttgtttgt gcacagcatg ag                22

<210> SEQ ID NO 65
<211> LENGTH: 22
<212> TYPE: DNA

```
<213> ORGANISM: Artificial Sequence
<220> FEATURE:
<223> OTHER INFORMATION: Oligonucleotide

<400> SEQUENCE: 65
acgagccctc agaacaaaac ag                                              22

<210> SEQ ID NO 66
<211> LENGTH: 21
<212> TYPE: DNA
<213> ORGANISM: Artificial Sequence
<220> FEATURE:
<223> OTHER INFORMATION: Oligonucleotide

<400> SEQUENCE: 66
ccactctgtc aaaatcttcg g                                               21

<210> SEQ ID NO 67
<211> LENGTH: 22
<212> TYPE: DNA
<213> ORGANISM: Artificial Sequence
<220> FEATURE:
<223> OTHER INFORMATION: Oligonucleotide

<400> SEQUENCE: 67
tcagtgaata gtgttgccgt gc                                              22

<210> SEQ ID NO 68
<211> LENGTH: 22
<212> TYPE: DNA
<213> ORGANISM: Artificial Sequence
<220> FEATURE:
<223> OTHER INFORMATION: Oligonucleotide

<400> SEQUENCE: 68
gcttcttcgg ttactagtta ac                                              22

<210> SEQ ID NO 69
<211> LENGTH: 21
<212> TYPE: DNA
<213> ORGANISM: Artificial Sequence
<220> FEATURE:
<223> OTHER INFORMATION: Oligonucleotide

<400> SEQUENCE: 69
tcaggagcat gttcagcgac g                                               21

<210> SEQ ID NO 70
<211> LENGTH: 21
<212> TYPE: DNA
<213> ORGANISM: Artificial Sequence
<220> FEATURE:
<223> OTHER INFORMATION: Oligonucleotide

<400> SEQUENCE: 70
ggtgaacaag acagctcttc g                                               21

<210> SEQ ID NO 71
<211> LENGTH: 23
<212> TYPE: DNA
<213> ORGANISM: Artificial Sequence
<220> FEATURE:
<223> OTHER INFORMATION: Oligonucleotide

<400> SEQUENCE: 71
aacggtggga atcactatgt cag                                             23
```

<210> SEQ ID NO 72
<211> LENGTH: 21
<212> TYPE: DNA
<213> ORGANISM: Artificial Sequence
<220> FEATURE:
<223> OTHER INFORMATION: Oligonucleotide

<400> SEQUENCE: 72
tgatggtcag ctacagtgct g                                              21

<210> SEQ ID NO 73
<211> LENGTH: 22
<212> TYPE: DNA
<213> ORGANISM: Artificial Sequence
<220> FEATURE:
<223> OTHER INFORMATION: Oligonucleotide

<400> SEQUENCE: 73
tttcgtgaag gtgaaatagc ag                                             22

<210> SEQ ID NO 74
<211> LENGTH: 20
<212> TYPE: DNA
<213> ORGANISM: Artificial Sequence
<220> FEATURE:
<223> OTHER INFORMATION: Oligonucleotide

<400> SEQUENCE: 74
ggtcttcagc ataggattgg                                                20

<210> SEQ ID NO 75
<211> LENGTH: 20
<212> TYPE: DNA
<213> ORGANISM: Artificial Sequence
<220> FEATURE:
<223> OTHER INFORMATION: Oligonucleotide

<400> SEQUENCE: 75
cacagttcga gtgacatccc                                                20

<210> SEQ ID NO 76
<211> LENGTH: 20
<212> TYPE: DNA
<213> ORGANISM: Artificial Sequence
<220> FEATURE:
<223> OTHER INFORMATION: Oligonucleotide

<400> SEQUENCE: 76
gtgagatggc gctgctttcg                                                20

<210> SEQ ID NO 77
<211> LENGTH: 20
<212> TYPE: DNA
<213> ORGANISM: Artificial Sequence
<220> FEATURE:
<223> OTHER INFORMATION: Oligonucleotide

<400> SEQUENCE: 77
gcacaagggt tgtgatgtag                                                20

<210> SEQ ID NO 78
<211> LENGTH: 20
<212> TYPE: DNA
<213> ORGANISM: Artificial Sequence
<220> FEATURE:

<223> OTHER INFORMATION: Oligonucleotide

<400> SEQUENCE: 78
tactcagccc ggtgttcttg            20

<210> SEQ ID NO 79
<211> LENGTH: 25
<212> TYPE: DNA
<213> ORGANISM: Artificial Sequence
<220> FEATURE:
<223> OTHER INFORMATION: Oligonucleotide

<400> SEQUENCE: 79
tctggtccag ctgcccgtgt gttcc            25

<210> SEQ ID NO 80
<211> LENGTH: 22
<212> TYPE: DNA
<213> ORGANISM: Artificial Sequence
<220> FEATURE:
<223> OTHER INFORMATION: Oligonucleotide

<400> SEQUENCE: 80
ttggtatacg gatagaaatt gg            22

<210> SEQ ID NO 81
<211> LENGTH: 22
<212> TYPE: DNA
<213> ORGANISM: Artificial Sequence
<220> FEATURE:
<223> OTHER INFORMATION: Oligonucleotide

<400> SEQUENCE: 81
gcgtttgggt attcgttgct cc            22

<210> SEQ ID NO 82
<211> LENGTH: 22
<212> TYPE: DNA
<213> ORGANISM: Artificial Sequence
<220> FEATURE:
<223> OTHER INFORMATION: Oligonucleotide

<400> SEQUENCE: 82
ctcagtcgca tccaaaactg tg            22

<210> SEQ ID NO 83
<211> LENGTH: 33
<212> TYPE: DNA
<213> ORGANISM: Artificial Sequence
<220> FEATURE:
<223> OTHER INFORMATION: Oligonucleotide

<400> SEQUENCE: 83
ttaggcgcgc ctattcctag gtgctagcga acc            33

<210> SEQ ID NO 84
<211> LENGTH: 22
<212> TYPE: DNA
<213> ORGANISM: Artificial Sequence
<220> FEATURE:
<223> OTHER INFORMATION: Oligonucleotide

<400> SEQUENCE: 84
aatggacacg acactgatga ac            22

```
<210> SEQ ID NO 85
<211> LENGTH: 22
<212> TYPE: DNA
<213> ORGANISM: Artificial Sequence
<220> FEATURE:
<223> OTHER INFORMATION: Oligonucleotide

<400> SEQUENCE: 85
agccatgttg cttgcgaata gt                                              22

<210> SEQ ID NO 86
<211> LENGTH: 22
<212> TYPE: DNA
<213> ORGANISM: Artificial Sequence
<220> FEATURE:
<223> OTHER INFORMATION: Oligonucleotide

<400> SEQUENCE: 86
aaacaggcgc tggcatctgc ac                                              22

<210> SEQ ID NO 87
<211> LENGTH: 32
<212> TYPE: DNA
<213> ORGANISM: Artificial Sequence
<220> FEATURE:
<223> OTHER INFORMATION: Oligonucleotide

<400> SEQUENCE: 87
ggcgcgccca cgttcgtgcc acttattatg ta                                   32

<210> SEQ ID NO 88
<211> LENGTH: 22
<212> TYPE: DNA
<213> ORGANISM: Artificial Sequence
<220> FEATURE:
<223> OTHER INFORMATION: Oligonucleotide

<400> SEQUENCE: 88
aatggacacg acactgatga ac                                              22

<210> SEQ ID NO 89
<211> LENGTH: 23
<212> TYPE: DNA
<213> ORGANISM: Artificial Sequence
<220> FEATURE:
<223> OTHER INFORMATION: Oligonucleotide

<400> SEQUENCE: 89
ctagcgagag tgggtggcca tgc                                             23

<210> SEQ ID NO 90
<211> LENGTH: 28
<212> TYPE: DNA
<213> ORGANISM: Artificial Sequence
<220> FEATURE:
<223> OTHER INFORMATION: Oligonucleotide

<400> SEQUENCE: 90
cgcaatgtcc gtcgagcaac agccgcac                                        28

<210> SEQ ID NO 91
<211> LENGTH: 22
<212> TYPE: DNA
<213> ORGANISM: Artificial Sequence
<220> FEATURE:
<223> OTHER INFORMATION: Oligonucleotide
```

-continued

```
<400> SEQUENCE: 91
agccatgttg cttgcgaata gt                                              22

<210> SEQ ID NO 92
<211> LENGTH: 8
<212> TYPE: PRT
<213> ORGANISM: Artificial Sequence
<220> FEATURE:
<223> OTHER INFORMATION: Oligonucleotide

<400> SEQUENCE: 92

Leu Cys Ala Val Asn Leu Ala Glu
1               5

<210> SEQ ID NO 93
<211> LENGTH: 23
<212> TYPE: DNA
<213> ORGANISM: Artificial Sequence
<220> FEATURE:
<223> OTHER INFORMATION: Oligonucleotide

<400> SEQUENCE: 93
cctctgtgca gtaaaccttg ctg                                             23

<210> SEQ ID NO 94
<211> LENGTH: 1032
<212> TYPE: PRT
<213> ORGANISM: Caenorhabditis elegans

<400> SEQUENCE: 94

Met Asn Asp Arg Val Lys Ile Arg Trp Lys Glu Ala Lys Glu Arg Ile
1               5                   10                  15

Gly Asn Ala Tyr His Asp Tyr Gly Arg Leu Cys Ala Ala His Pro Lys
            20                  25                  30

Ala Cys Leu Ser Met Ser Leu Leu Thr Met Ile Val Leu Ser Tyr Pro
        35                  40                  45

Thr Ile Thr Arg Leu Arg Leu Pro Val Ser Thr Pro Ile Asp Val Phe
    50                  55                  60

Trp Ser Glu His Leu His Val Asn Asp Lys Ile Ala Pro Phe Trp Ile
65                  70                  75                  80

Asn Glu Asn Pro Ala Ser Tyr Ile Gln Gln Phe Ile Val Ser Thr Thr
                85                  90                  95

Ile Ser Pro Trp Asn Ala Thr Glu Met Gly Pro Glu His Ala Val Arg
            100                 105                 110

Ala Ala Ile Ala Thr Ala Phe Arg Ile Arg Gln Ile Leu Leu Ala Glu
        115                 120                 125

Pro Ala Val Glu Glu Leu Cys Leu Arg Leu Ala Asn Gln Arg Gln Asp
    130                 135                 140

Ser Ser Trp Pro Phe Arg Ser Lys Ser Leu Cys Val Val Leu Ser Pro
145                 150                 155                 160

Ala Ser Ile Trp Tyr Asn Asn Leu Gln Lys Phe Arg Glu Asp Asp Asp
                165                 170                 175

Thr Ile Thr Thr Val Phe Asn Glu His Cys Lys Ser Thr Phe Cys Met
            180                 185                 190

Arg Asp Leu Leu Leu Gly Ala Pro Ile Ala Ala Thr Gly Ile Lys Gln
        195                 200                 205

Lys Tyr Gln Thr Asn Arg Lys Arg Lys Ile Glu Phe Ala Val Thr Met
    210                 215                 220
```

-continued

```
Phe Phe Ala Arg Tyr Ser Lys Lys Val Ile Gln Gly Ile Arg Glu Lys
225                 230                 235                 240

Leu Gln Lys Glu Phe Glu Leu Val Asp Thr Pro Asn Asp Gln Arg
            245                 250                 255

Thr Phe Val Gln Val Tyr Phe His Pro Leu Lys Thr Phe Ser Asp Tyr
                260                 265                 270

Ile Pro Leu Ile Ser Thr Tyr Phe Val Cys Met Ile Tyr Val Tyr Tyr
        275                 280                 285

Ser Ser Arg Lys Ile Gln Met Val Ala Ser Arg Trp Gly Leu Ala Phe
    290                 295                 300

Ala Ser Ser Phe Thr Val Ala Ser Thr Leu Leu Met Thr Thr Gly Ile
305                 310                 315                 320

Cys Ala His Leu Asp Leu Ser Thr Thr Thr Trp Gly Ser Glu Val Tyr
                325                 330                 335

Pro Tyr Ile Ala Leu Ile Met Gly Leu Glu Asn Thr Leu Cys Ile Thr
                340                 345                 350

Arg Ser Val Val Tyr Thr Ser Pro Ser Leu Asp Val Ser Ser Arg Ile
            355                 360                 365

Ala His Gly Leu Ser Gln Glu Gly Tyr Lys Leu Thr Lys Tyr Tyr Ile
    370                 375                 380

Leu Glu Leu Leu Ala Leu Leu Ile Gly Phe Leu Thr Arg Ile Ser Asp
385                 390                 395                 400

Ile Gln Glu Phe Cys Gln Phe Ser Val Ile Cys Val Thr Val Asp Phe
                405                 410                 415

Tyr Met Gln Leu Phe Phe Tyr Ala Pro Cys Leu Thr Phe Asp Leu Gln
                420                 425                 430

Arg Leu Gly Leu Glu Glu Lys Arg Lys Phe Ala Glu Ile Leu Leu Tyr
            435                 440                 445

Glu Glu Ile Pro Arg Leu Lys Asn Tyr Ala Pro Val Ser Cys Pro Met
450                 455                 460

Arg Lys Ile Trp Pro Lys Leu Phe Val Met Lys Lys Met Gln Lys Arg
465                 470                 475                 480

Arg Val Ser Asp Ser Gly Ile Glu Asp Val Met Lys Asn Asp Glu Gln
                485                 490                 495

Arg Arg Leu Leu Ile Ser Ser Glu Phe Asp Ser Lys Asp Asp Gly Asp
            500                 505                 510

Val Gln Glu Pro Arg Pro Glu Asp Ser Val Arg Met Lys Ile Met Tyr
            515                 520                 525

Phe Ile Thr Arg Thr Arg Ile Val Gln Arg Thr Ile Leu Val Val Phe
        530                 535                 540

Ala Ile Trp Thr Val Phe Leu Val Phe Val Gly Ser Arg Gln Leu
545                 550                 555                 560

Gly Met Glu Ser Asn Leu Thr Ser Lys Leu Trp Pro Pro Val Ala His
                565                 570                 575

Glu Tyr Asn Ile Ser Leu Asn Ser Arg Tyr Val Thr Phe Leu Pro Pro
            580                 585                 590

Ile Val Ile Asn Ala Ile His Pro Thr Asp Ile Leu Leu Gln Asn
        595                 600                 605

Val Glu Lys Thr His Val Asn Val Pro Asn Glu Glu Asp Ala Pro
    610                 615                 620

Ile Leu Arg Ser Arg Ile Asp Trp Leu Glu Met Gln Leu Lys Met Tyr
625                 630                 635                 640

Leu Ala Ala Phe Trp Leu Leu Leu Ile Thr Thr Val Ile Ser Phe Phe
```

```
                   645                 650                 655
Ala Tyr Val Phe Leu Ile Asp Arg Trp Lys Leu Arg Gly Val Lys Gln
                660                 665                 670
Ile Gln Glu Gln Gln Met Ser Glu Thr Thr Thr Asp Ser Ser Glu Thr
                675                 680                 685
Val Lys Asn Phe Val Asp Thr Leu Pro Ile Val Tyr Gln Gly His Arg
                690                 695                 700
Phe Pro Ile Glu Ser Val Ala Ile Asp Pro Glu Asp Thr Ser Thr Phe
705                 710                 715                 720
Val Ser Cys Cys Gln Glu Gly Val Val Tyr Val Trp Asn Thr Gln Thr
                725                 730                 735
Gly Gln Arg Thr Leu Arg Ile Asn Arg Leu Arg Ala Val Pro Glu Lys
                740                 745                 750
Gly Lys Glu Ile Pro Ser Ala Pro Lys Ile Trp Ala Ile Ala Lys Arg
                755                 760                 765
His Phe Phe Ser Asn Thr Thr Ser His Val Val Cys Arg Glu Asp Asp
                770                 775                 780
Val Ala Val Val Arg Leu Asp Gly Ser Ile Glu Phe Leu Arg Ile Asp
785                 790                 795                 800
Tyr Asp Arg Thr Asp Gly Thr Ile Arg Val Arg Lys Ile Glu Leu Leu
                805                 810                 815
Lys Ser Val Arg Ala His Gln Lys Pro Val Cys Arg Ile Ala Ile Trp
                820                 825                 830
Lys Ser Gln Leu Ile Thr Ser Ser Phe Asp Arg Ser Ile Lys Met Trp
                835                 840                 845
Asn Trp Ala Glu Asn Pro Glu Gln Ile Asp Ile Ser Asn Val Phe Leu
                850                 855                 860
Ala His Asn Ser Pro Val Val Asn Leu Ala Val Asp Glu Ala Thr Ser
865                 870                 875                 880
Ile Met Tyr Ser Ser Cys Glu Glu Gly Val Ile Cys Trp Trp Asn Leu
                885                 890                 895
Asn Thr Gly Glu Leu Ile Arg Thr Asn Asp Asn Asn Tyr Thr Trp Ala
                900                 905                 910
Phe Gln Leu Ala Thr Ser Ser Asp Tyr Leu Leu Gly Phe Tyr Gly Ser
                915                 920                 925
Ser Gln Leu Tyr Met Trp Asn Val Glu Asn Gly Gln Leu Ala Cys Arg
                930                 935                 940
Val Ser Asp Ala Leu Gly Asp Gly Thr Ser Glu Asp Thr Leu Tyr Thr
945                 950                 955                 960
Val Gly Ser Ser Gly Val Val Ser Phe Asp Asp Gln Val Ala Ala Thr
                965                 970                 975
Thr Ser Ser Asp Ser Val Thr Phe Trp Asp Leu Lys His Arg Ala Ile
                980                 985                 990
Ile Gly Lys Val Lys Leu Asn Gly Lys Ile Ser Ser Met Arg Lys Asn
                995                 1000                1005
Thr Ser His Ser Val Leu Cys Gly Val Asp Asn Ser Met Tyr Ser
                1010                1015                1020
Val Thr Val Pro Leu Val Arg Phe Lys
                1025                1030

<210> SEQ ID NO 95
<211> LENGTH: 119
<212> TYPE: PRT
<213> ORGANISM: Caenorhabditis elegans
```

```
<220> FEATURE:
<221> NAME/KEY: misc_feature
<222> LOCATION: (1)..(119)
<223> OTHER INFORMATION: "Xaa" is any amino acid

<400> SEQUENCE: 95

Ser Gly Phe His Glu Leu Gly His Ala Trp Ala Ala Thr Ser Asn Gly
1               5                   10                  15

Val Thr Val Asn Gly Phe Gly Ile Phe Ile Leu Ala Val Tyr Pro Gly
            20                  25                  30

Ala Phe Thr Asp Ile Glu Ala Val Thr Leu Lys Arg Ala Thr Thr Phe
            35                  40                  45

Arg Arg Leu Gln Ile Phe Gly Ala Gly Ile Trp His Asn Leu Leu Leu
        50                  55                  60

Ala Leu Leu Ala Met Xaa Met Phe His Ala Ser Pro Val Ile Leu Ser
65                  70                  75                  80

Pro Val Leu Ala Asn Gly Tyr Xaa Val Ser Val Arg Gly Val Asp Val
                85                  90                  95

Arg Ser Xaa Leu Ser Asn Pro Arg Thr Gly Leu Val Ala Gly Asp Val
            100                 105                 110

Val Lys Ser Val Asp Glu Cys
            115
```